United States Patent
Miller et al.

(10) Patent No.: US 10,194,911 B2
(45) Date of Patent: Feb. 5, 2019

(54) SURGICAL STAPLER WITH READY STATE INDICATOR

(71) Applicant: Ethicon Endo-Surgery, LLC, Guaynabo, PR (US)

(72) Inventors: Christopher C. Miller, Loveland, OH (US); John P. Measamer, Cincinnati, OH (US); Frederick E. Shelton, IV, Hillsboro, OH (US); Charles J. Scheib, Loveland, OH (US); Brian F. DiNardo, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 505 days.

(21) Appl. No.: 14/751,306

(22) Filed: Jun. 26, 2015

(65) Prior Publication Data
US 2016/0374681 A1    Dec. 29, 2016

(51) Int. Cl.
*A61B 17/068* (2006.01)
*A61B 17/10* (2006.01)
(Continued)

(52) U.S. Cl.
CPC .......... *A61B 17/105* (2013.01); *A61B 17/068* (2013.01); *A61B 17/1155* (2013.01);
(Continued)

(58) Field of Classification Search
CPC .............. A61B 17/068; A61B 17/1155; A61B 2017/00473; A61B 2017/00734; A61B 2017/2946
(Continued)

(56) References Cited

U.S. PATENT DOCUMENTS

| 5,205,459 A | 4/1993 | Brinkerhoff et al. |
| 5,271,544 A | 12/1993 | Fox et al. |

(Continued)

FOREIGN PATENT DOCUMENTS

| EP | 2510891 | 10/2012 |
| EP | 2839787 | 2/2015 |
| WO | WO 2010/045533 | 4/2010 |

OTHER PUBLICATIONS

International Search Report and Written Opinion dated Jan. 30, 2017 re Application No. PCT/US16/38931.
(Continued)

*Primary Examiner* — Andrew M Tecco
*Assistant Examiner* — Praachi M Pathak
(74) *Attorney, Agent, or Firm* — Frost Brown Todd LLC

(57) ABSTRACT

A surgical circular stapler has a handle assembly, a shaft, a stapling assembly, and a firing assembly. The shaft extends distally from the handle assembly. The stapling assembly is secured to a distal end of the shaft. Longitudinal translation of the firing assembly causes the stapling assembly to drive a plurality of staples in a circular array to secure two lumens of tissue together. The stapling assembly may further drive a blade to sever any excess tissue interior of the circular array of staples. The stapler further includes an indicator configured to indicate "readiness" of the stapler and/or to control firing of the stapling assembly. The indicator may indicate a position of an anvil relative to the stapling assembly and/or coupling of the anvil to the stapling assembly among other things. In addition, the stapler may include a self-draining battery pack configured to drain power upon removal from the stapler.

18 Claims, 61 Drawing Sheets

(51) Int. Cl.
  *A61B 17/115* (2006.01)
  *A61B 17/00* (2006.01)
  *A61B 90/00* (2016.01)

(52) U.S. Cl.
  CPC ............... *A61B 2017/00115* (2013.01); *A61B 2017/00734* (2013.01); *A61B 2090/0808* (2016.02); *A61B 2090/0811* (2016.02); *A61B 2090/0812* (2016.02)

(58) Field of Classification Search
  USPC ............................................ 227/179.1, 175.2
  See application file for complete search history.

(56) References Cited

U.S. PATENT DOCUMENTS

| | | |
|---|---|---|
| 5,275,322 A | 1/1994 | Wolf et al. |
| 5,285,945 A | 2/1994 | Brinkerhoff et al. |
| 5,292,053 A | 3/1994 | Smith et al. |
| 5,333,773 A | 8/1994 | Main et al. |
| 5,350,104 A | 9/1994 | Main et al. |
| 5,533,661 A | 7/1996 | Main et al. |
| 6,945,444 B2 | 9/2005 | Gresham et al. |
| 7,794,475 B2 | 9/2010 | Hess et al. |
| 8,408,439 B2 | 4/2013 | Huang et al. |
| 8,453,914 B2 | 6/2013 | Laurent et al. |
| 8,910,847 B2 | 12/2014 | Nalagatla et al. |
| 9,113,880 B2 | 8/2015 | Zemlok et al. |
| 9,161,803 B2 | 10/2015 | Yates et al. |
| 9,522,005 B2 | 12/2016 | Williams et al. |
| 2014/0144968 A1 | 5/2014 | Shelton |
| 2014/0144969 A1 | 5/2014 | Scheib et al. |
| 2014/0151429 A1 | 6/2014 | Scheib et al. |
| 2014/0151430 A1 | 6/2014 | Scheib et al. |
| 2014/0158747 A1 | 6/2014 | Measamer et al. |
| 2014/0166717 A1 | 6/2014 | Swayze et al. |
| 2014/0166718 A1 | 6/2014 | Swayze et al. |
| 2014/0166728 A1 | 6/2014 | Swayze et al. |
| 2014/0236184 A1 | 8/2014 | Leimbach et al. |
| 2015/0083772 A1 | 3/2015 | Miller et al. |
| 2015/0083773 A1 | 3/2015 | Measamer et al. |
| 2015/0083774 A1 | 3/2015 | Measamer et al. |
| 2015/0083775 A1 | 3/2015 | Leimbach et al. |

OTHER PUBLICATIONS

European Search Report, Partial, dated Oct. 10, 2016 for Application No. EP 16176144.0, 8 pgs.
European Search Report, Extended, and Written Opinion dated Mar. 16, 2017 for EP 16176144.0, 17 pgs.

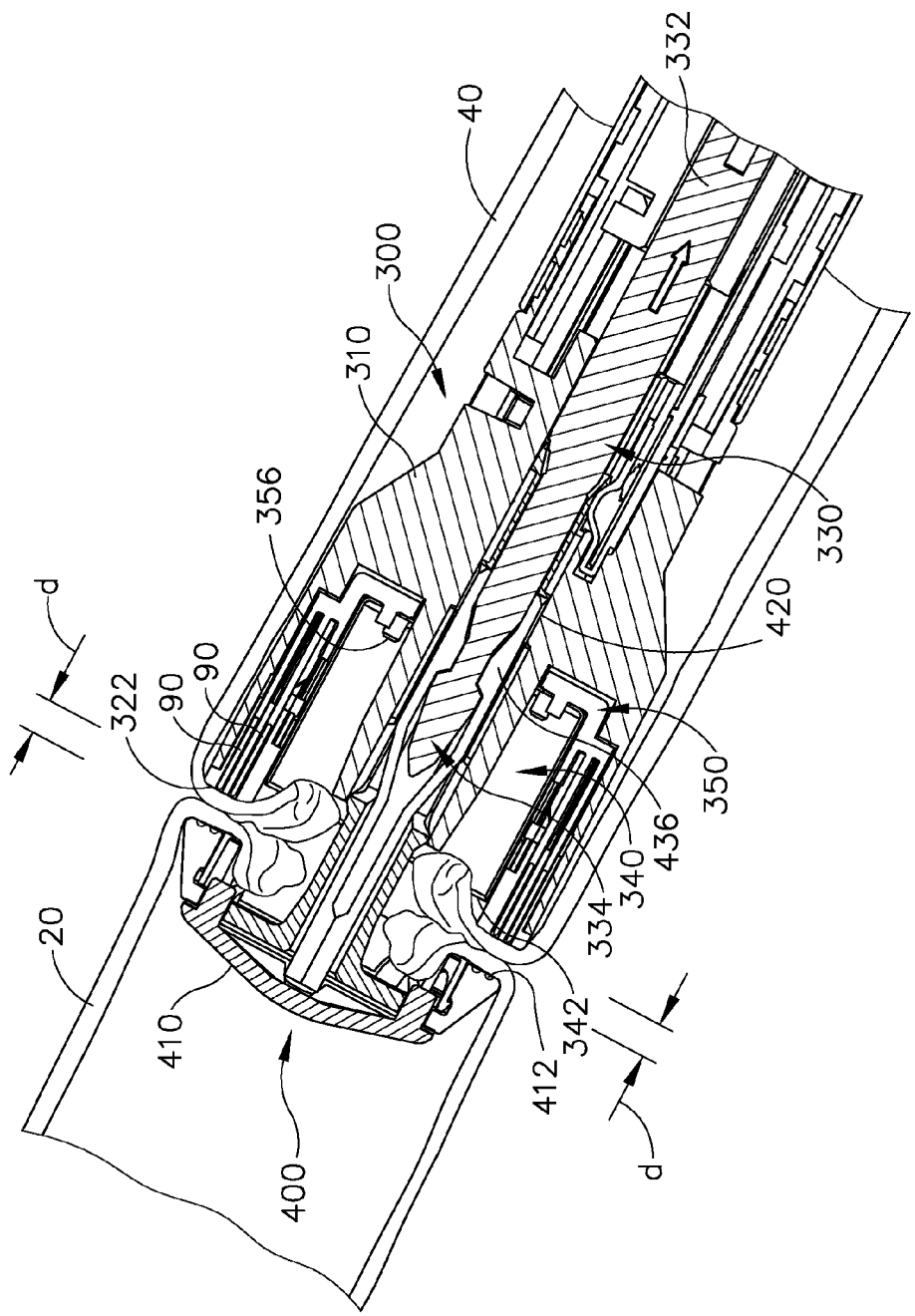

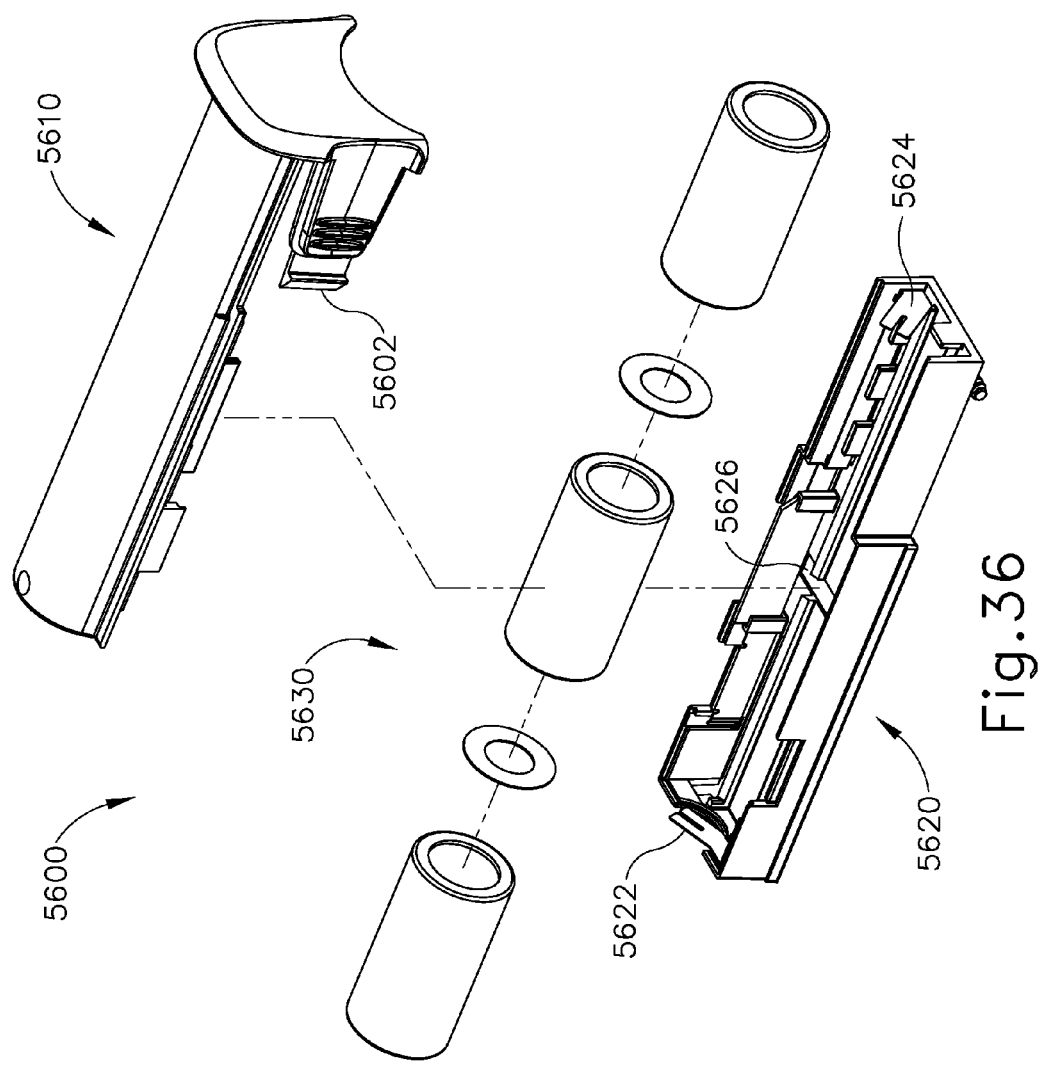

SURGICAL STAPLER WITH READY STATE INDICATOR

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015; U.S. Pub. No. 2015/0083773, entitled "Surgical Stapling Instrument with Drive Assembly Having Toggle Features," published Mar. 26, 2015, now U.S. Pat. No. 9,936,949, issued Apr. 10, 2018; U.S. Pub. No. 2015/0083774, entitled "Control Features for Motorized Surgical Stapling Instrument," published Mar. 26, 2015, now U.S. Pat. No. 9,907,552, issued Mar. 6, 2018; and U.S. Pub. No. 2015/0083775, entitled "Surgical Stapler with Rotary Cam Drive," published Mar. 26, 2015, now U.S. Pat. No. 9,713,469, issued Jul. 25, 2017. The disclosure of each of the above-cited U.S. Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 21C depicts a cross-sectional side view of the anvil of FIG. 3 positioned within the first section of the digestive tract and the stapling head assembly of FIG. 6 positioned in the second section of the digestive tract, with the anvil retracted toward the stapling head assembly to thereby clamp tissue between the anvil and the stapling head assembly;

FIG. 36 depicts a partially exploded perspective view of the battery pack of FIG. 34;

Figure 1:
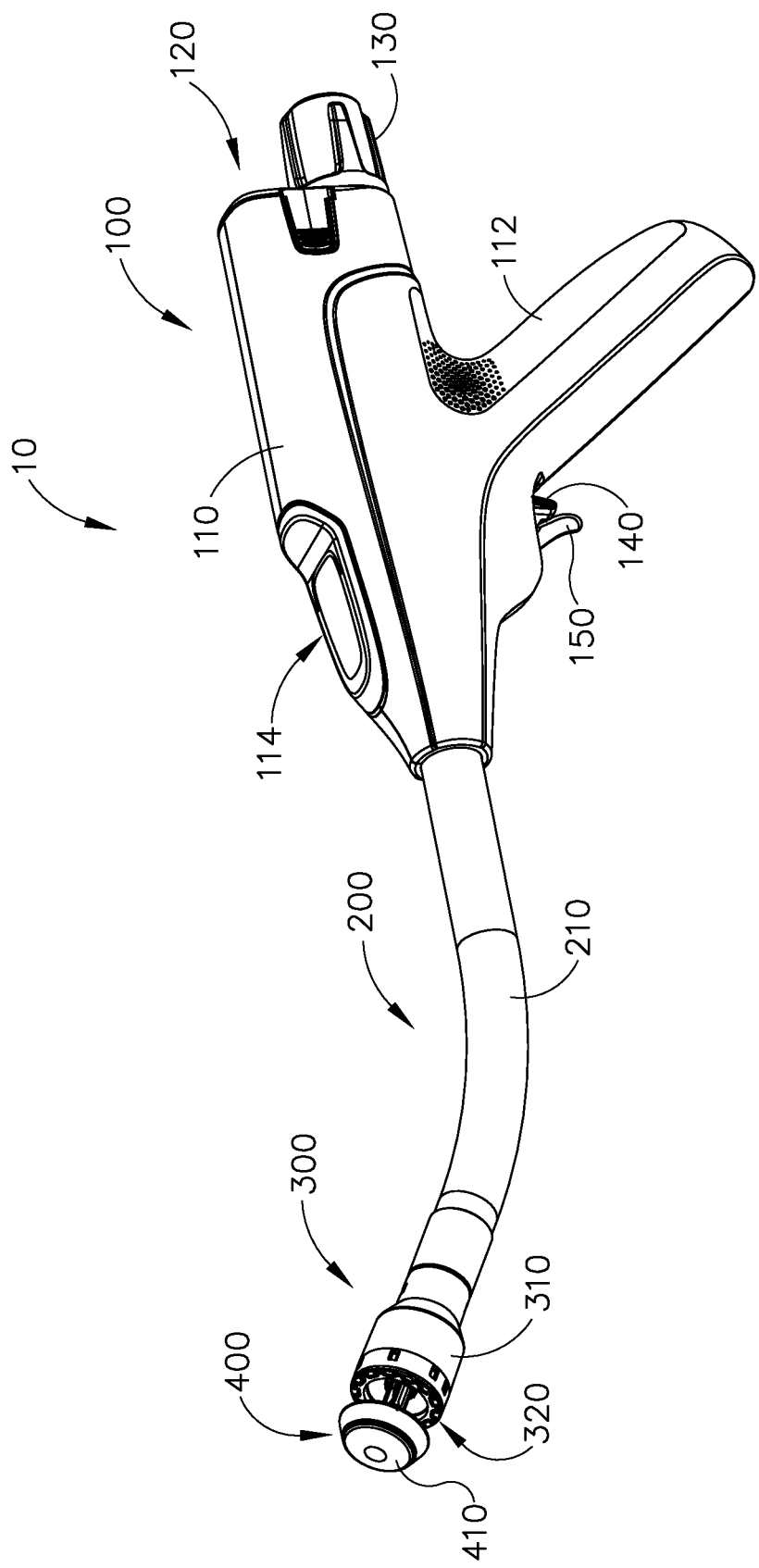
FIG. 1 depicts a perspective view of an exemplary circular stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

Figure 2:
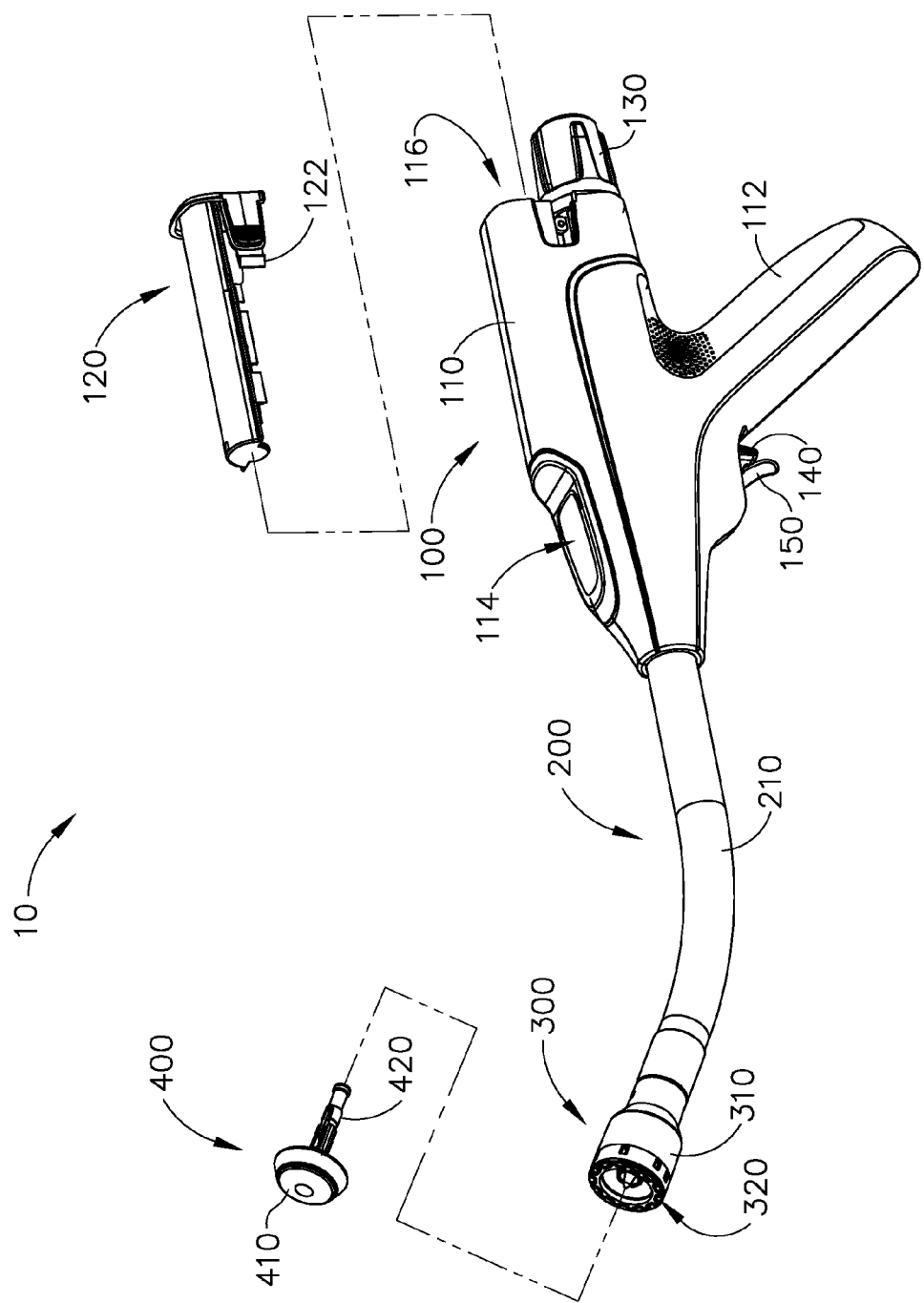
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end anastomosis between two sections of an anatomical lumen such as a portion of a patient's digestive tract. Instrument (10) of this example comprises a handle assembly (100), a shaft assembly (200), a stapling head assembly (300), and an anvil (400). Handle assembly (100) comprises a casing (110) defining an obliquely oriented pistol grip (112). In some versions, pistol grip (112) is perpendicularly oriented. In some other versions, pistol grip (112) is omitted. Handle assembly (110) further includes a window (114) that permits viewing of a movable indicator needle (526) as will be described in greater detail below. In some versions, a series of hash marks, colored regions, and/or other fixed indicators are positioned adjacent to window (114) in order to provide a visual context for indicator needle (526), thereby facilitating operator evaluation of the position of needle (526) within window (114). Various suitable alternative features and configurations for handle assembly (112) will be apparent to those of ordinary skill in the art in view of the teachings herein.

Instrument (10) of the present example further includes a battery pack (120). Battery pack (120) is operable to provide electrical power to a motor (160) in pistol grip (112) as will be described in greater detail below. Battery pack (120) is removable from handle assembly (100). In particular, as shown in FIGS. 1-2, battery pack (120) may be inserted into a socket (116) defined by casing (110). Once battery pack (120) is fully inserted in socket (116), latches (122) of battery pack (120) may resiliently engage interior features of casing (110) to provide a snap fit. To remove battery pack (120), the operator may press latches (122) inwardly to disengage latches (122) from the interior features of casing (110) then pull battery pack (120) proximally from socket (116). It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is inserted in socket (116). It should also be understood that, in some versions, battery pack (120) is unitarily incorporated within handle assembly (100) such that battery back (120) cannot be removed from handle assembly (100).

Shaft assembly (200) extends distally from handle assembly (100) and includes a preformed bend. In some versions, the preformed bend is configured to facilitate positioning of stapling head assembly (300) within a patient's colon. Various suitable bend angles or radii that may be used will be apparent to those of ordinary skill in the art in view of the teachings herein. In some other versions, shaft assembly (200) is straight, such that shaft assembly (200) lacks a preformed bend. Various exemplary components that may be incorporated into shaft assembly (100) will be described in greater detail below.

Stapling head assembly (300) is located at the distal end of shaft assembly (200). As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A knob (130) at the proximal end of handle assembly (100) is rotatable relative to casing (110) to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the tissue.

A. Exemplary Anvil

In the following discussion of anvil (400), the terms "distal" and "proximal" (and variations thereof) will be used with reference to the orientation of anvil (400) when anvil (400) is coupled with shaft assembly (200) of instrument (10). Thus, proximal features of anvil (400) will be closer to the operator of instrument (10); while distal features of anvil (400) will be further from the operator of instrument (10).

Figure 3:
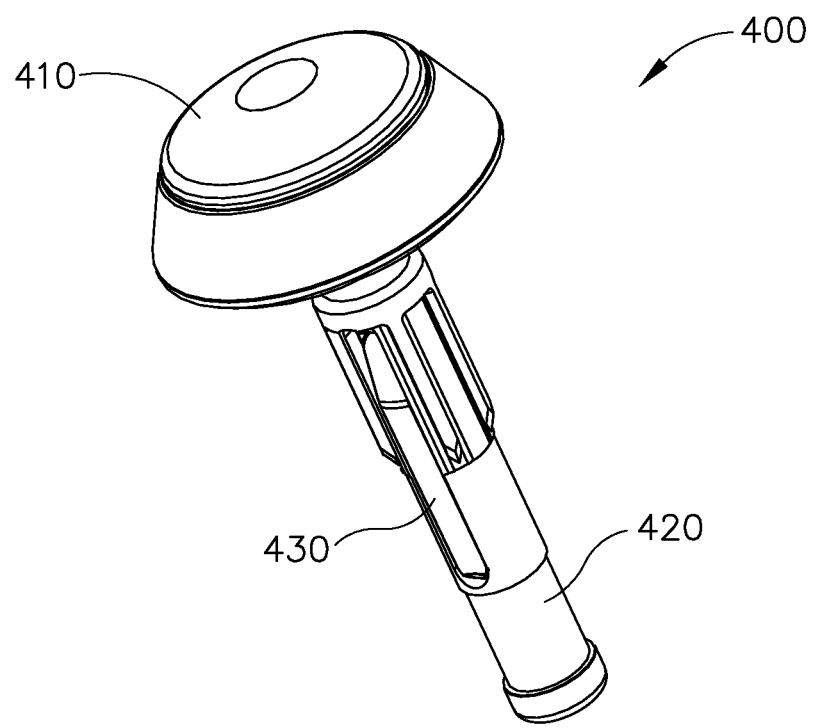
FIG. 3 depicts a perspective view of the anvil of the circular stapler of FIG. 1.
Figure 4:
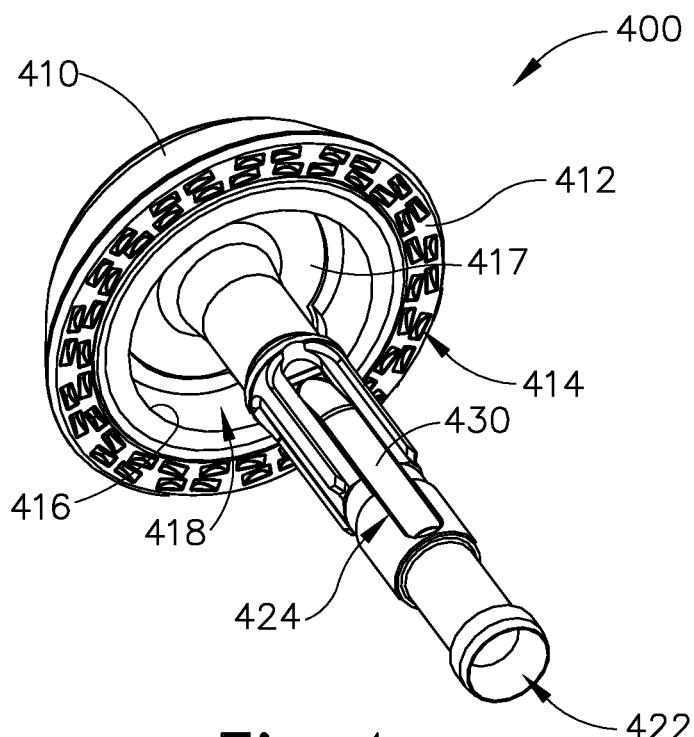
FIG. 4 depicts another perspective view of the anvil of FIG. 3.
Figure 5:
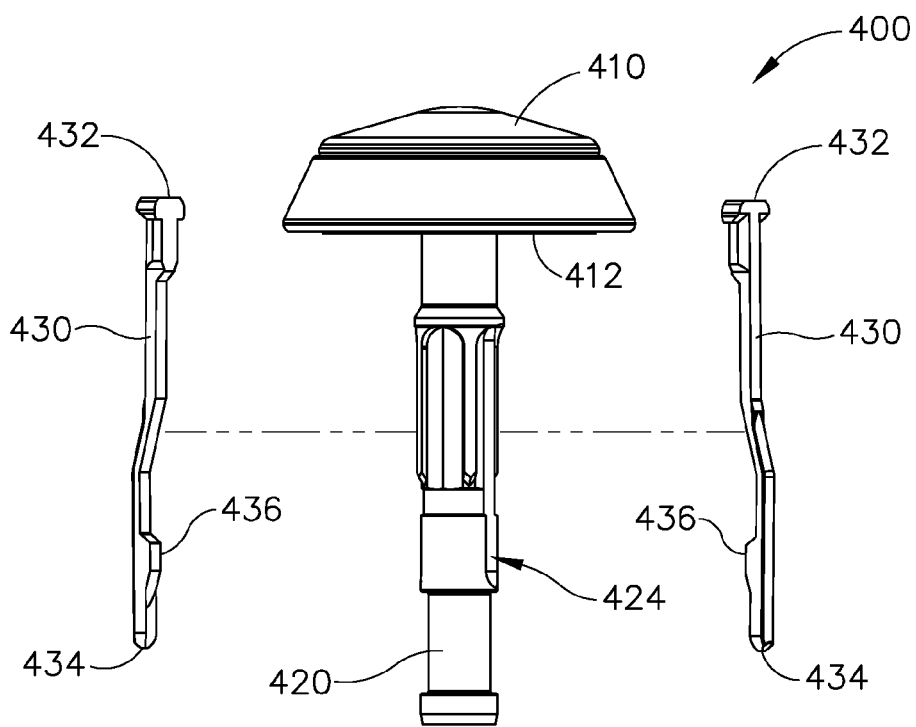
FIG. 5 depicts an exploded side elevational view of the anvil of FIG. 3.

As best seen in FIGS. 3-5, anvil (400) of the present example comprises a head (410) and a shank (420). Head (410) includes a proximal surface (412) that defines a plurality of staple forming pockets (414). Staple forming pockets (414) are arranged in two concentric annular arrays. In some other versions, staple forming pockets (414) are arranged in three or more concentric annular arrays. Staple forming pockets (414) are configured to deform staples as the staples are driven into staple forming pockets (414). For instance, each staple forming pocket (414) may deform a generally "U" shaped staple into a "B" shape as is known in the art. As best seen in FIG. 4, proximal surface (412) terminates at an inner edge (416), which defines an outer boundary of an annular recess (418) surrounding shank (420).

Shank (420) defines a bore (422) and includes a pair of pivoting latch members (430) positioned in bore (422). As best seen in FIG. 5, each latch member (430) includes a "T" shaped distal end (432), a rounded proximal end (434), and a latch shelf (436) located distal to proximal end (434). "T" shaped distal ends (432) secure latch members (430) within bore (422). Latch members (430) are positioned within bore (422) such that distal ends (434) are positioned at the proximal ends of lateral openings (424), which are formed through the sidewall of shank (420). Lateral openings (424) thus provide clearance for distal ends (434) and latch shelves (436) to deflect radially outwardly from the longitudinal axis defined by shank (420). However, latch members (430) are configured to resiliently bias distal ends (434) and latch shelves (436) to radially inwardly toward the longitudinal axis defined by shank (420). Latch members (430) thus act as retaining clips. This allows anvil (400) to be removably secured to a trocar (330) of stapling head assembly (300) as will be described in greater detail below. It should be understood, however, that latch members (436) are merely optional. Anvil (400) may be removably secured to a trocar (330) using any other suitable components, features, or techniques.

In addition to or in lieu of the foregoing, anvil (400) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

B. Exemplary Stapling Head Assembly

Figure 6:
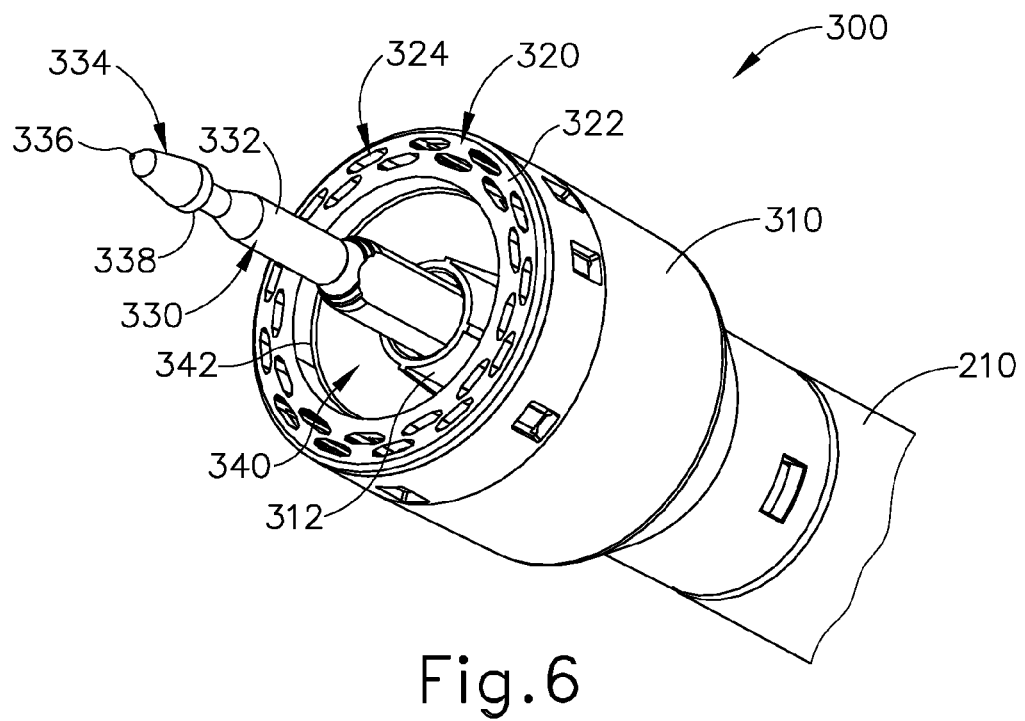
FIG. 6 depicts a perspective view of the stapling head assembly of the circular stapler of FIG. 1.
Figure 7:
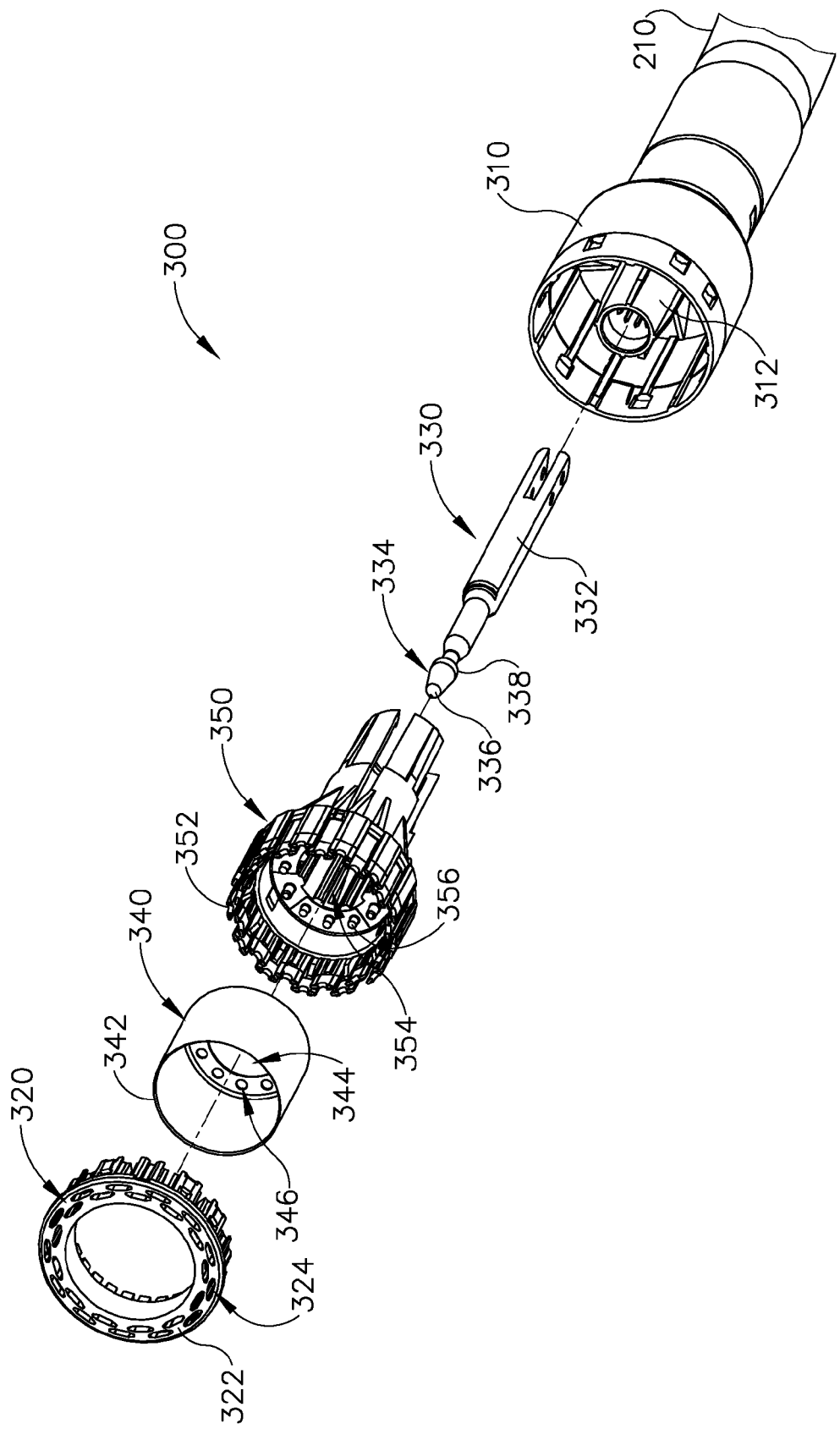
FIG. 7 depicts an exploded perspective view of the stapling head assembly of FIG. 6.

As best seen in FIGS. 6-7, stapling head assembly (300) of the present example is coupled to a distal end of shaft assembly (200) and comprises a tubular casing (310) housing a slidable staple driver member (350). A cylindraceous inner core member (312) extends distally within tubular casing (310). Tubular casing (310) is fixedly secured to an outer sheath (210) of shaft assembly (200), such that tubular casing (310) serves as a mechanical ground for stapling head assembly (300).

Trocar (330) is positioned coaxially within inner core member (312) of tubular casing (310). As will be described in greater detail below, trocar (330) is operable to translate distally and proximally relative to tubular casing (310) in response to rotation of knob (130) relative to casing (110) of handle assembly (100). Trocar (330) comprises a shaft (332) and a head (334). Head (334) includes a pointed tip (336) and an inwardly extending proximal surface (338). Shaft (332) thus provides a reduced outer diameter just proximal to head (334), with surface (338) providing a transition between that reduced outer diameter of shaft (332) and the outer diameter of head (334). While tip (336) is pointed in the present example, tip (336) is not sharp. Tip (336) will thus not easily cause trauma to tissue due to inadvertent contact with tissue. Head (334) and the distal portion of shaft (332) are configured for insertion in bore (422) of anvil (420). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit due to latch members (430).

Staple driver member (350) is operable to actuate longitudinally within tubular casing (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. It should be understood that the arrangement of staple drivers (352) may be modified just like the arrangement of staple forming pockets (414) as described above. Staple driver member (350) also defines a bore (354) that is configured to coaxially receive core member (312) of tubular casing (310). An annular array of studs (356) project distally from a distally presented surface surrounding bore (354).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of tubular casing (310). An annular array of openings (346) formed in knife member (340) is configured to complement the annular array of studs (356) of staple driver member (350), such that knife member (340) is fixedly secured to staple driver member (350) via studs (356) and openings (346). Other suitable structural relationships between knife member (340) and stapler driver member (350) will be apparent to those of ordinary skill in the art in view of the teachings herein.

A deck member (320) is fixedly secured to tubular casing (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (322) may be modified just like the arrangement of staple forming pockets (414) as described above. It should also be understood that various structures and techniques may be used to contain staples within stapling head assembly (300) before stapling head assembly (300) is actuated. Such structures and techniques that are used to contain staples within stapling head assembly (300) may prevent the staples from inadvertently falling out through staple openings (324) before stapling head assembly (300) is actuated. Various suitable forms that such structures and techniques may take will be apparent to those of ordinary skill in the art in view of the teachings herein.

As best seen in FIG. 6, deck member (320) defines an inner diameter that is just slightly larger than the outer diameter defined by knife member (340). Deck member (320) is thus configured to allow knife member (340) to translate distally to a point where cutting edge (342) is distal to deck surface (322).

In addition to or in lieu of the foregoing, stapling head assembly (300) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

C. Exemplary Shaft Assembly

Figure 8:
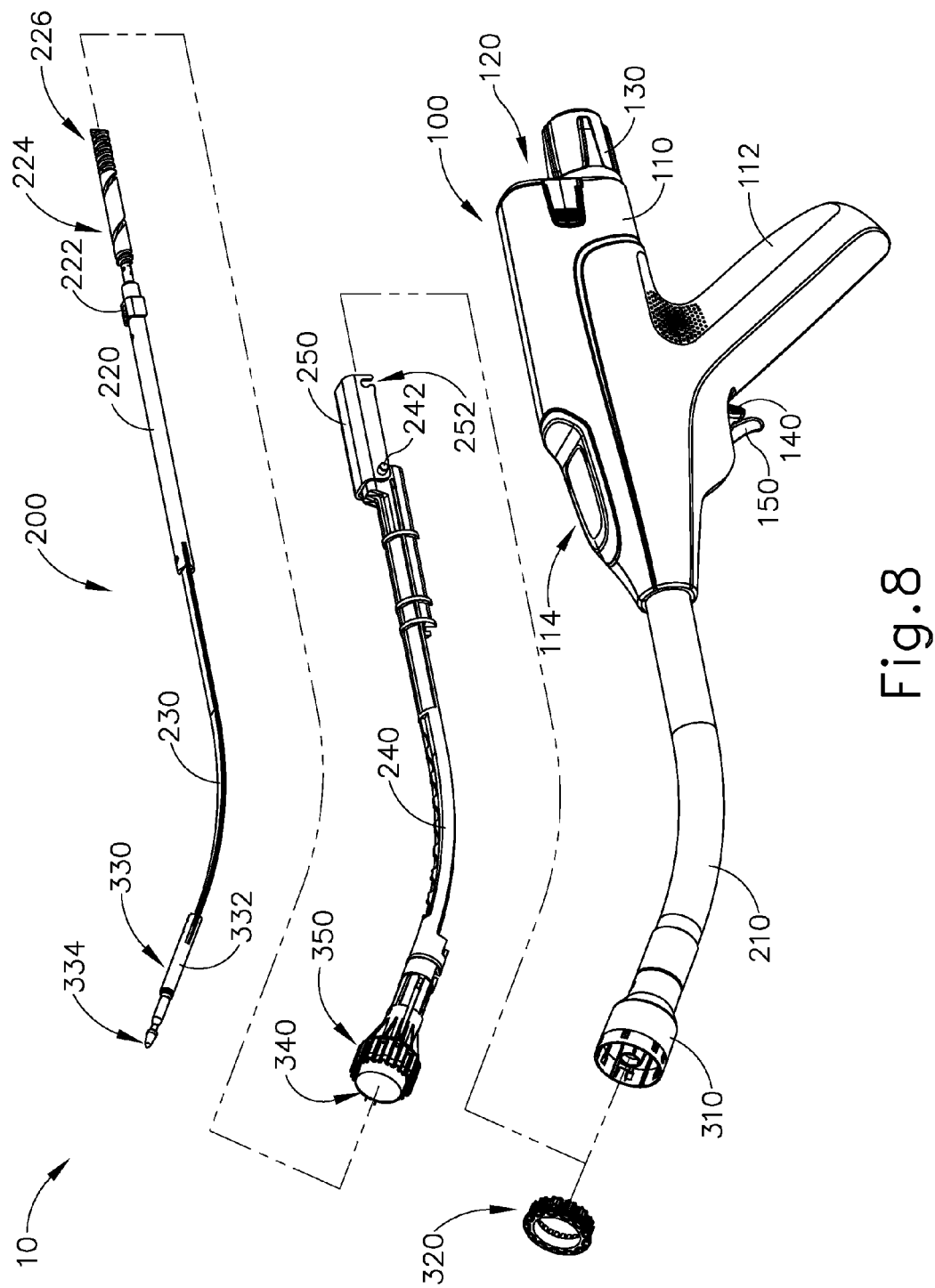
FIG. 8 depicts an exploded perspective view of the circular stapler of FIG. 1, with portions of the shaft assembly shown separately from each other.

FIG. 8 shows various components of shaft assembly (200), which couples components of stapling head assembly (300) with components of handle assembly (100). In particular, and as noted above, shaft assembly (200) includes an outer sheath (210) that extends between handle assembly (100) and tubular casing (310). In the present example, outer sheath (210) is rigid and includes a preformed curved section as noted above.

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220). It should therefore be understood that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226). Details regarding the movement of trocar actuation rod (220) will be described in greater detail below.

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350). Details regarding the movement of drive bracket (250) will be described in greater detail below.

While not shown in FIG. 8, it should be understood that shaft assembly (200) may further include one or more spacer elements within outer sheath (210). Such spacer elements may be configured to support trocar actuation band assembly (230) and/or stapling head assembly driver (240) as trocar actuation band assembly (230) and/or stapling head assembly driver (240) translate through outer sheath (210). For instance, such spacer elements may prevent trocar actuation band assembly (230) and/or stapling head assembly driver (240) from buckling as trocar actuation band assembly (230) and/or stapling head assembly driver (240) translate through outer sheath (210). Various suitable forms that such spacer elements may take will be apparent to those of ordinary skill in the art in view of the teachings herein.

In addition to or in lieu of the foregoing, shaft assembly (200) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

D. Exemplary Actuator Handle Assembly

Figure 9:
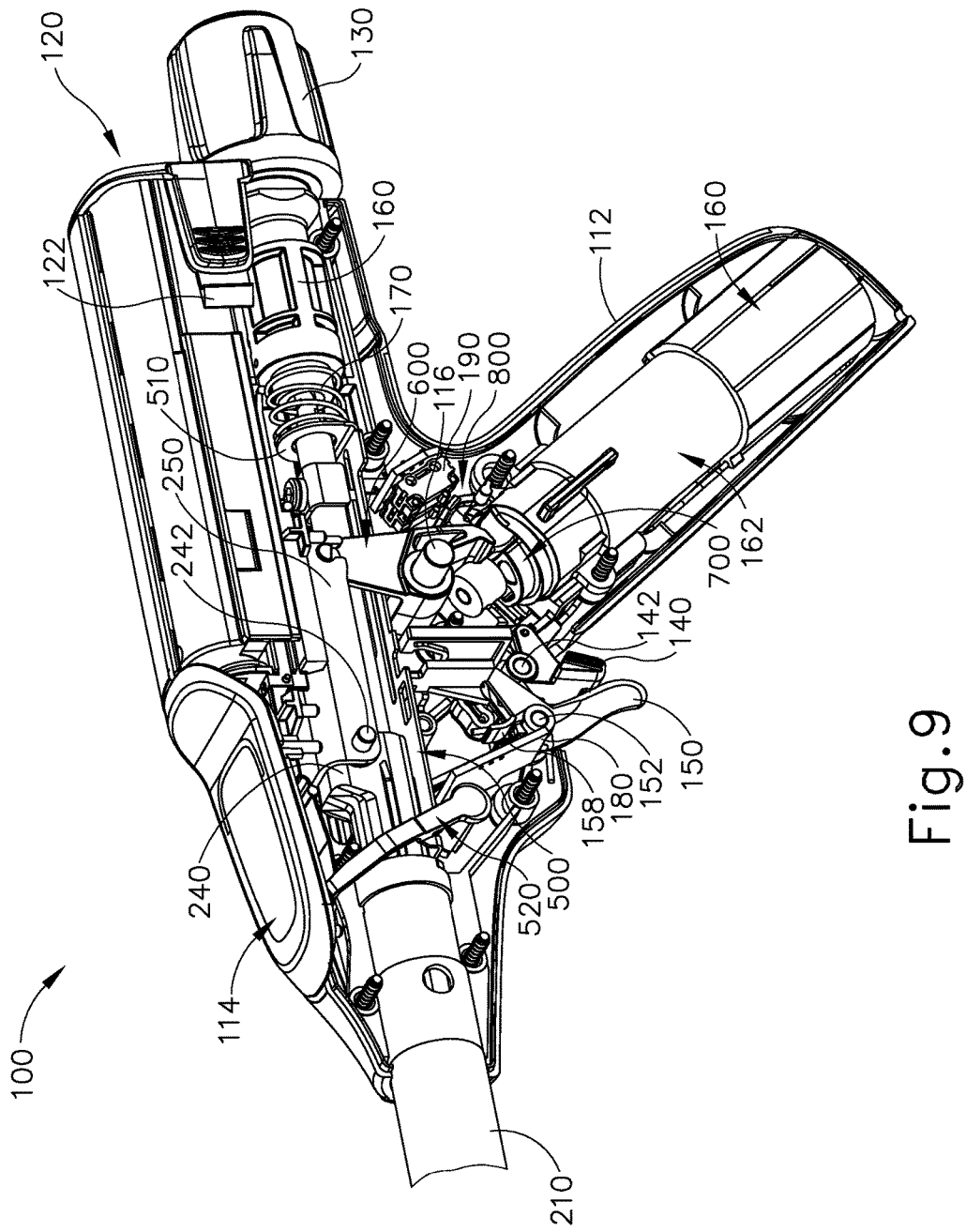
FIG. 9 depicts a perspective view of the handle assembly of the circular stapler of FIG. 1, with a housing half omitted to reveal internal components of the handle assembly.

As shown in FIG. 9, handle assembly (100) includes several components that are operable to actuate anvil (400) and stapling head assembly (300). Handle assembly (100) also includes components that are operable to selectively lock out triggers (140, 150) based on the position of anvil (400) relative to stapling head assembly (300). When triggers (140, 150) are locked out, firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range. The components of handle assembly (100) that provide the foregoing operability will be described in greater detail below.

1. Exemplary Anvil Actuation Assembly

Knob (130) protrudes proximally from casing (110) of handle assembly and is rotatable relative to casing (110). As shown in FIG. 9, a nut (160) is secured to the distal end of knob (130). In the present example, nut (160) is fixedly secured to the distal end of knob (130) such that nut (160) will rotate unitarily with knob (130). Nut (160) and knob (130) are configured to cooperate with trocar actuation rod (220) to thereby translate trocar actuation rod (220) longitudinally relative to casing (110) in response to rotation of nut (160) and knob (130) relative to casing (110). As noted above, trocar (330) will translate longitudinally relative to outer sheath (210) in response to translation of trocar actuation rod (220) relative to outer sheath (210) and casing (110).

The proximal portion of trocar actuation rod (220) is positioned within handle assembly (100) to engage nut (160) and knob (130). In particular, trocar actuation rod (220) is positioned within handle assembly (100) such that coarse helical threading (224) will selectively engage a thread engagement feature (not shown) within the interior of nut (160); and such that fine helical threading (226) will selectively engage a thread engagement feature (not shown) within the interior of knob (130). In some versions, the thread engagement feature of nut (160) comprises an inwardly directed tab; while the thread engagement feature of knob (130) comprises a helical threading. Other suitable forms that such thread engagement features may take will be apparent to those of ordinary skill in the art in view of the teachings herein.

In the present example, when nut (160) and knob (130) are rotated relative to casing (110), trocar actuation rod (220) travels proximally through a first range of longitudinal motion where coarse helical threading (224) is engaged with nut (160) to provide a relatively rapid rate of translation. Fine helical threading (226) is not engaged with knob (130) during this range of motion. When nut (160) and knob (130) are further rotated relative to casing (110) after trocar actuation rod (220) completes the first range of motion, trocar actuation rod (220) will continue to travel proximally through a second range of longitudinal motion where fine helical threading (226) is engaged with knob (130) to provide a relatively slow rate of translation. Thus, trocar actuation rod (220) will translate proximally through a sequence of rapid translation followed by slow translation, based on engagement between coarse helical threading (224) and nut (160) followed by engagement between fine helical threading (226) and knob (130).

It should be understood that when anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (500) away from stapling head assembly (300). Knob (130) may thus be used to adjust the gap distance (d) between opposing surfaces (412, 322) of anvil (400) and stapling head assembly (300) until a suitable gap distance (d) has been achieved as shown in FIG. 21C and as described in greater detail below.

2. Exemplary Trigger Lockout Assembly

As noted above, knob may be used to adjust the gap distance (d) between opposing surfaces (412, 322) of anvil (400) and stapling head assembly (300). Setting an appropriate gap distance (d) before actuating stapling head assembly (300) may be critical to the success of an anastomosis. For instance, if the gap distance (d) is too great, the staples that are deployed at the anastomosis site may not be sufficiently formed by staple forming pockets (414). This may result in leakage at the anastomosis site, and in some cases may ultimately lead to the separation of the anatomical lumen sections that are joined at the anastomosis site. If the gap distance (d) is too small, the internal structure of the tissue compressed between surfaces (412, 322) may be damaged to the point where the structural integrity of the tissue is compromised. This may prevent the tissue from adequately holding the formed staples, which again may result in leakage or other failure of the anastomosis. It may therefore be desirable to provide the operator with some form of feedback indicating whether the gap distance (d) is within an appropriate range. It may also be desirable to prevent the operator from actuating stapling head assembly (300) unless the gap distance (d) is within an appropriate range.

Figure 10:
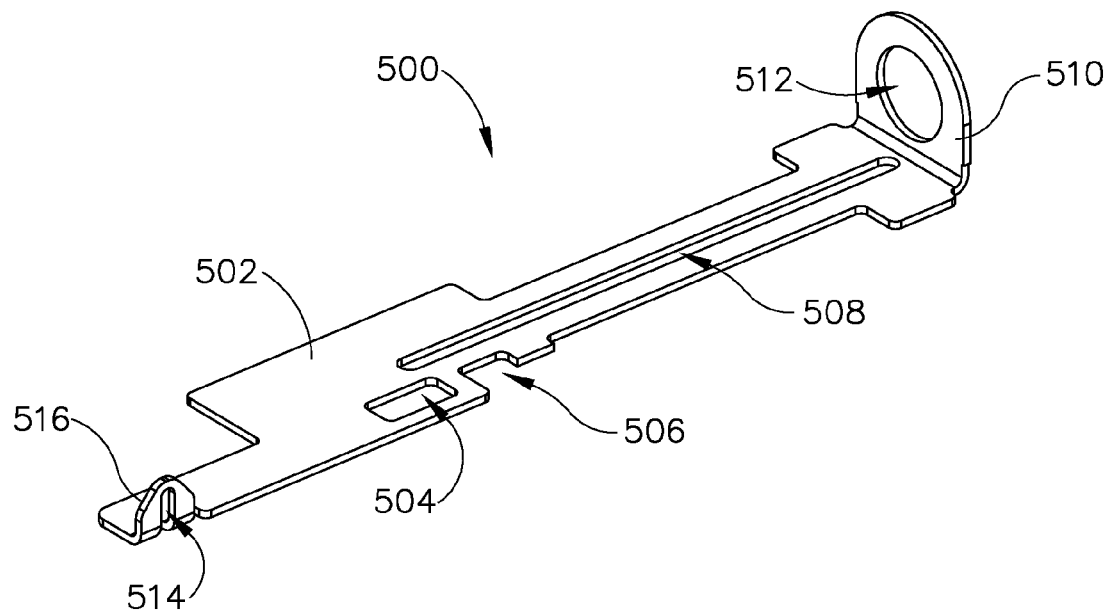
FIG. 10 depicts a perspective view of a bracket of the handle assembly of FIG. 9.

FIGS. 9-12E show components that provide feedback to the operator to indicate whether the gap distance (d) is within an appropriate range; and prevent the operator from actuating stapling head assembly (300) unless the gap distance (d) is within an appropriate range. As best seen in FIGS. 12B-12C, a bracket (500) is configured and positioned to move in response to movement of trocar actuation rod (220). As best seen in FIG. 10, bracket (500) includes a rigid body (502) that defines a first slot (504), a second slot (506), and a third slot (508). An upright feature (510) is positioned at the proximal end of body (502) and defines an opening (512). Trocar actuation rod (220) extends coaxially through opening (512). As shown in FIG. 9, a coil spring (170) is interposed between the proximal end of upright feature (510) and a rigid bulkhead feature that is defined by casing (110) and that forms a support journal for nut (160). The bulkhead is fixed within casing (110) and thereby provides a ground for the proximal end of coil spring (170), such that coil spring (170) resiliently imparts a distal bias to bracket (500) via upright feature (510). Bracket (500) further includes a laterally presented flange (516) at the distal end of body (502). Flange (516) defines a slot (514).

Figure 11:
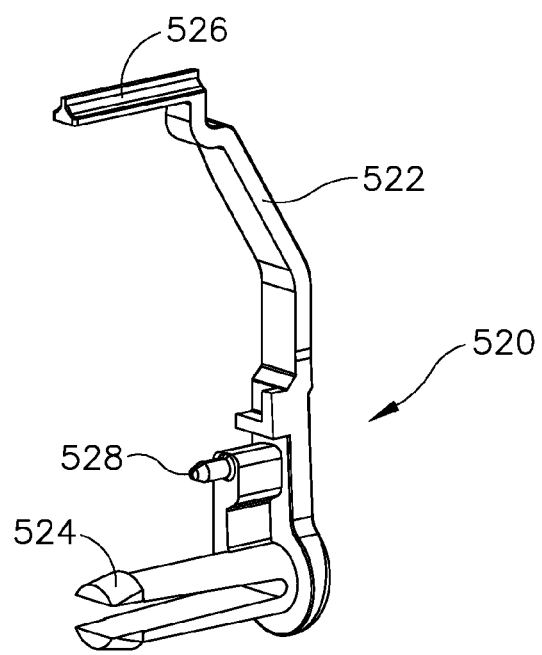
FIG. 11 depicts a perspective view of an indicator member of the handle assembly of FIG. 9.
Figure 12A:
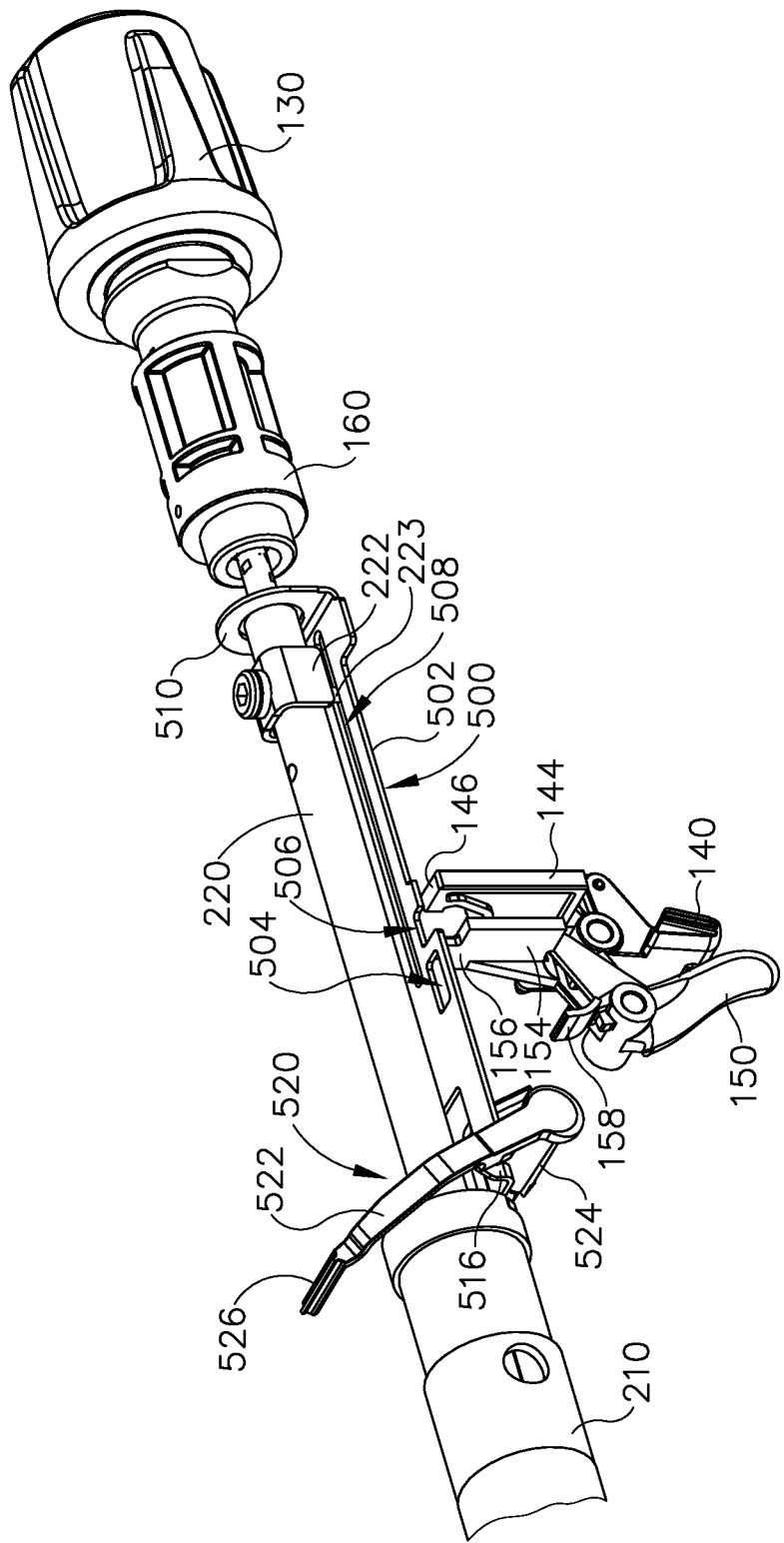
FIG. 12A depicts a perspective view of an anvil actuation assembly of the circular stapler of FIG. 1, an actuation rod in a first position.
Figure 12B:
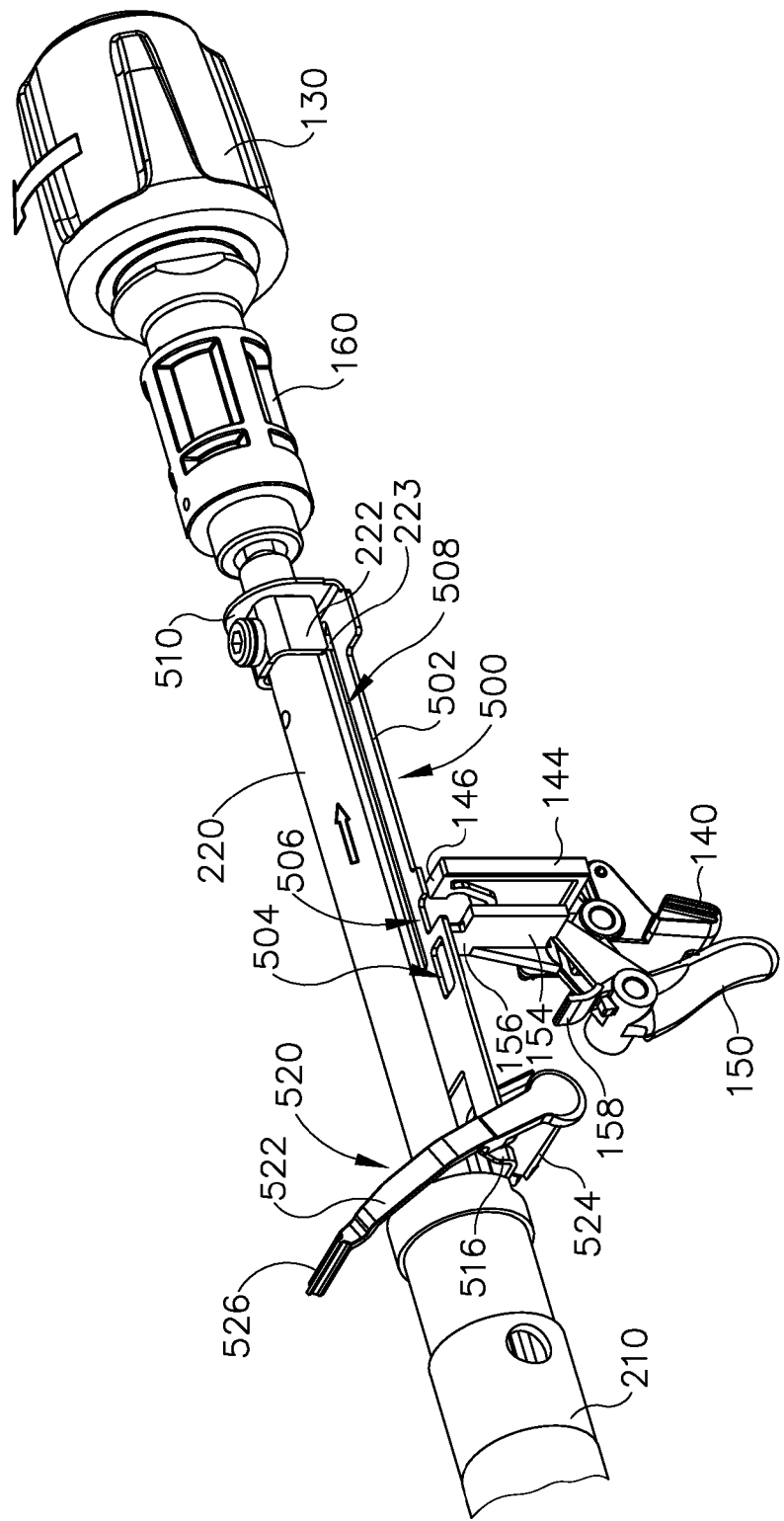
FIG. 12B depicts a perspective view of the anvil actuation assembly of FIG. 12A, with the actuation rod moved to a second position to engage the bracket of FIG. 10.
Figure 12C:
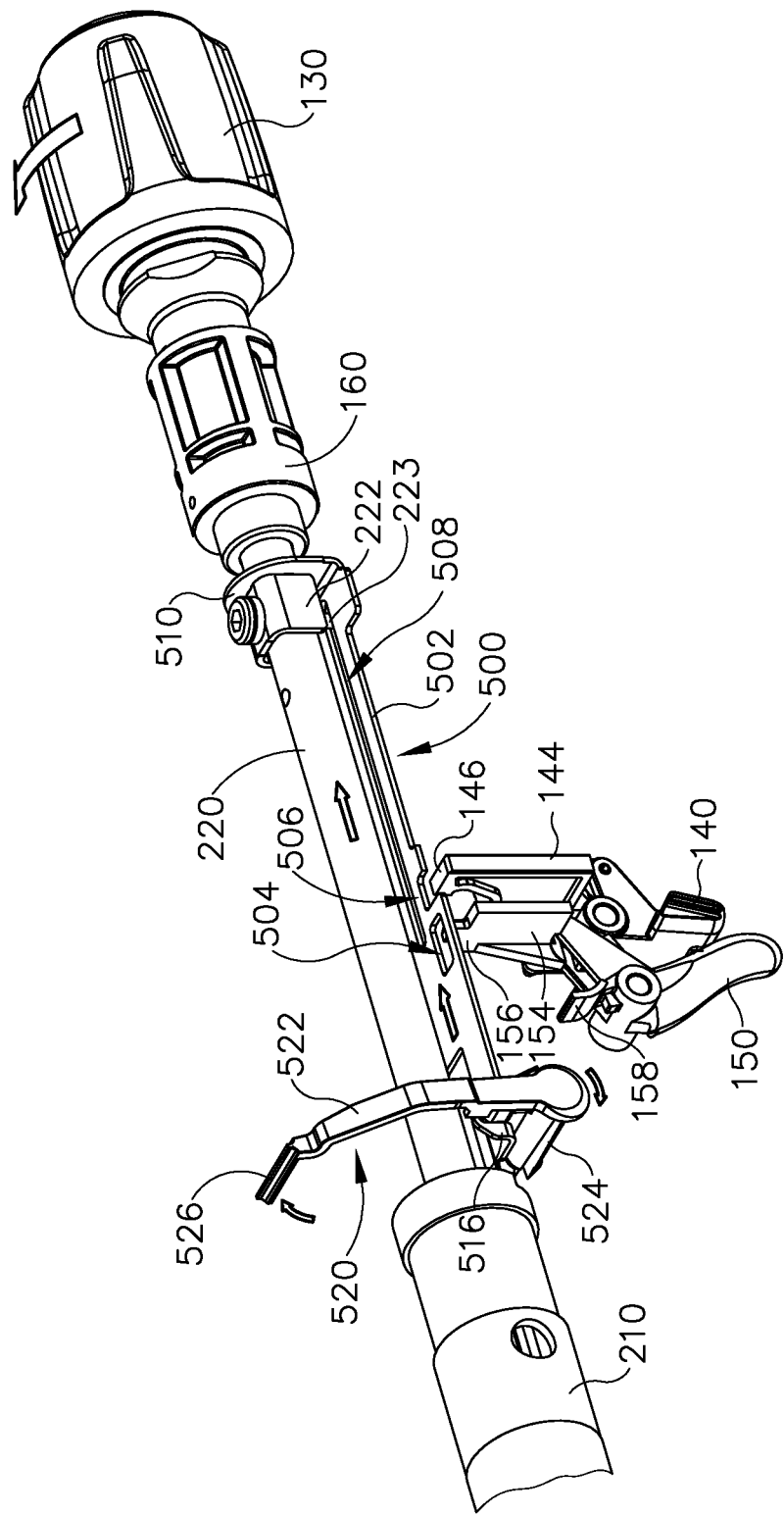
FIG. 12C depicts a perspective view of the anvil actuation assembly of FIG. 12A, with the actuation rod moved to a third position to retract the bracket of FIG. 10 proximally.

As best seen in FIGS. 12B-12C, an indicator member (520) is configured to pivot in response to translation of bracket (500). As best seen in FIG. 11, indicator member (520) comprises an upright arm (522), a snap pin (524) projecting laterally from a lower end of arm (522), an indicator needle (526) projecting laterally from an upper end of arm (522), and a coupling pin (528) projecting laterally from an intermediate region of arm (522). Snap pin (524) is configured to snap into a complementary recess provided by casing (110). Snap pin (524) thereby secures indicator member (520) to casing (110) yet permits indicator member (520) to pivot relative to casing (110) about the longitudinal axis of snap pin (524). Indicator needle (526) is positioned to be visible through window (114) of handle assembly (110) to thereby visually indicate the pivotal position of indicator member (520). Coupling pin (528) is slidably received in slot (514) of flange (516) of bracket (500). This engagement between indicator member (520), casing (110), and bracket (500) provides pivotal movement of indicator member (520) in response to translation of bracket (500).

Bracket (500) is configured to selectively prevent and permit actuation of triggers (140, 150). In particular, slots (504, 506) of bracket (500) are configured to selectively provide clearance for actuation of triggers (140, 150). As shown in FIGS. 12A-12E, safety trigger (140) is pivotably coupled with a first upright member (144). First upright member (144) is coupled with casing (110) such that first upright member (144) is configured to translate upwardly in response to pivoting of safety trigger (140) toward pistol grip (112). However, body (502) of bracket (500) is configured to prevent this movement of first upright member (144) and safety trigger (140) by engaging the upper end (146) of first upright member (144). Body (502) thus blocks movement of first upright member (144) and safety trigger (140) until bracket (500) is moved to a position where slot (506) is aligned with upper end (146) to thereby provide clearance for upward movement of first upright member (144). It should therefore be understood that safety trigger (140) cannot be pivoted toward pistol grip (112) until slot (506) is positioned over upper end (146).

Similarly, firing trigger (150) is pivotably coupled with a second upright member (154). Second upright member (154) is coupled with casing (110) such that second upright member (154) is configured to translate upwardly in response to pivoting of safety trigger (150) toward pistol grip (112). However, body (502) of bracket (500) is configured to prevent this movement of second upright member (154) and firing trigger (150) by engaging the upper end (156) of second upright member (154). Even if safety trigger (140) is pivoted out of the way to otherwise permit movement of firing trigger (150), body (502) blocks movement of second upright member (154) and firing trigger (150) until bracket (500) is moved to a position where slot (504) is aligned with upper end (156) to thereby provide clearance for upward movement of second upright member (154). It should therefore be understood that, even if safety trigger (140) is pivoted out of the way to otherwise permit movement of firing trigger (150), firing trigger (150) cannot be pivoted toward pistol grip (112) until slot (504) is positioned over upper end (156).

Third slot (508) is configured to receive a downwardly projecting boss (223) of clip (222), which is rigidly secured to trocar actuation rod (220). While casing (110) is configured to allow bracket (500) to translate longitudinally within casing (110), casing (110) includes rails, channels, and/or other features that prevent bracket (500) from rotating within casing (110). Thus, the positioning of boss (223) in slot (508) prevents clip (222) and trocar actuation rod (220) from rotating within casing (110). Boss (223) and slot (508) nevertheless allow bracket (500) to translate longitudinally within casing (110) as will be described in greater detail below.

FIGS. 12A-12E depict the above-described components at various stages of operation. In particular, in FIG. 12A, trocar actuation rod (220) is in a distal-most position, such that trocar (330) is in a distal-most position. At this stage, the operator may couple anvil (400) with trocar (330) by inserting trocar (330) into bore (422) until latch members (430) are secured to head (334) of trocar (330). The operator then rotates knob (130), which rotates nut (160). As knob (130) and nut (160) rotate, engagement between coarse helical threading (224) of trocar actuation rod (220) and the complementary feature of nut (160) causes trocar actuation rod (220) to retract proximally at a relatively rapid rate, such that trocar actuation rod (220) reaches the position shown in FIG. 12B. This provides proximal retraction of trocar actuation rod (220) provides retraction of trocar (330) and anvil (400). As trocar actuation rod (220) moves from the position shown in FIG. 12A to the position shown in FIG. 12B, bracket (500) remains stationary. This is due to the fact that clip (222) is spaced apart from upright feature (510) at the stage shown in FIG. 12A and does not engage upright feature (510) until trocar actuation rod (220) reaches the position shown in FIG. 12B.

After reaching the stage shown in FIG. 12B, the operator may continue rotating knob (130) and nut (160), which causes further proximal retraction of trocar actuation rod (220) as shown in FIG. 12C. This of course causes further proximal retraction of trocar (330) and anvil (400). As trocar actuation rod (220) moves from the position shown in FIG. 12B to the position shown in FIG. 12C, clip (222) bears against bracket (500), driving bracket (500) proximally. This proximal movement of bracket (500) causes indicator member (520) to pivot from the position shown in FIG. 12B to the position shown in FIG. 12C due to the positioning of pin (528) in slot (514) of flange (516).

As indicator member (520) pivots from the position shown in FIG. 12B to the position shown in FIG. 12C, the operator may observe the position of indicator needle (526) through window (114) of handle assembly (110). As noted above, a series of hash marks, colored regions, and/or other fixed indicators may be positioned adjacent to window (114) in order to provide a visual context for indicator needle (526), thereby facilitating operator evaluation of the position of needle (526) within window (114). It should be understood that the position of needle (526) within window (114) will be indicative of the longitudinal position of trocar (330)

and anvil (400). The position of needle (526) within window (114) will thus indicate the gap distance (d) between opposing surfaces (412, 322) of anvil (400) and stapling head assembly (300). While observing the position of needle (526) within window (114), the operator may rotate knob (130) clockwise or counterclockwise to further retract or advance trocar (330) and anvil (400), thereby providing fine adjustment of the gap distance (d) until a desired gap distance (d) is reached within an appropriate range.

In order to provide fine control of the gap distance (d) adjustment at the stage shown in FIG. 12C, trocar actuation rod (220) will be at a longitudinal position where fine helical threading (226) is engaged with a complementary feature of knob (130) and coarse helical threading (224) is disengaged from the complementary feature of nut (160). In some versions, coarse helical threading (224) disengages nut (160) and fine helical threading (226) begins to engage knob (130) once trocar actuation rod (220) reaches the longitudinal position shown in FIG. 12B (i.e., when clip (222) first engages upright member (510)). In some other versions, the transition from engagement by coarse helical threading (224) to fine helical threading (226) occurs sometime between the stage shown in FIG. 12B and the stage shown in FIG. 12C. Other suitable stages at which the coarse-to-fine transition may occur will be apparent to those of ordinary skill in the art in view of the teachings herein. It should also be understood that some alternative versions of trocar actuation rod (220) may have just a single threading section, with the pitch of the threading being consistent along the length of the threading. In other words, trocar actuation rod (220) does not necessarily need to have two different sections of threading (224, 226) with different pitches.

At the stage shown in FIG. 12C, slot (506) is aligned with upper end (146) to thereby provide clearance for upward movement of first upright member (144). Similarly, slot (504) is aligned with upper end (156) to thereby provide clearance for upward movement of second upright member (154). In the present example, slots (504, 506) are sized and positioned such that slots (504, 506) only provide clearance for upward movement of upright members (144, 154) when the gap distance (d) is within a clinically acceptable range. By way of example only, a "clinically acceptable range" for the gap distance (d) may be between approximately 0.110 inches and approximately 0.040 inches. As another merely illustrative example, a "clinically acceptable range" for the gap distance (d) may be between approximately 0.110 inches and approximately 0.020 inches. Even when slots (504, 506) are positioned to provide clearance for upward movement of upright members (144, 154) as shown in FIG. 12C, safety trigger (140) will still block pivotal movement of firing trigger (150) about a pin (152) (FIG. 9) when safety trigger (140) is in the non-actuated position shown in FIG. 12C. Thus, in order to enable movement of firing trigger (150), the operator will need to first actuate safety trigger (140) about a pin (142) (FIG. 9) from the position shown in FIG. 12C to the position shown in FIG. 12D.

Figure 12D:
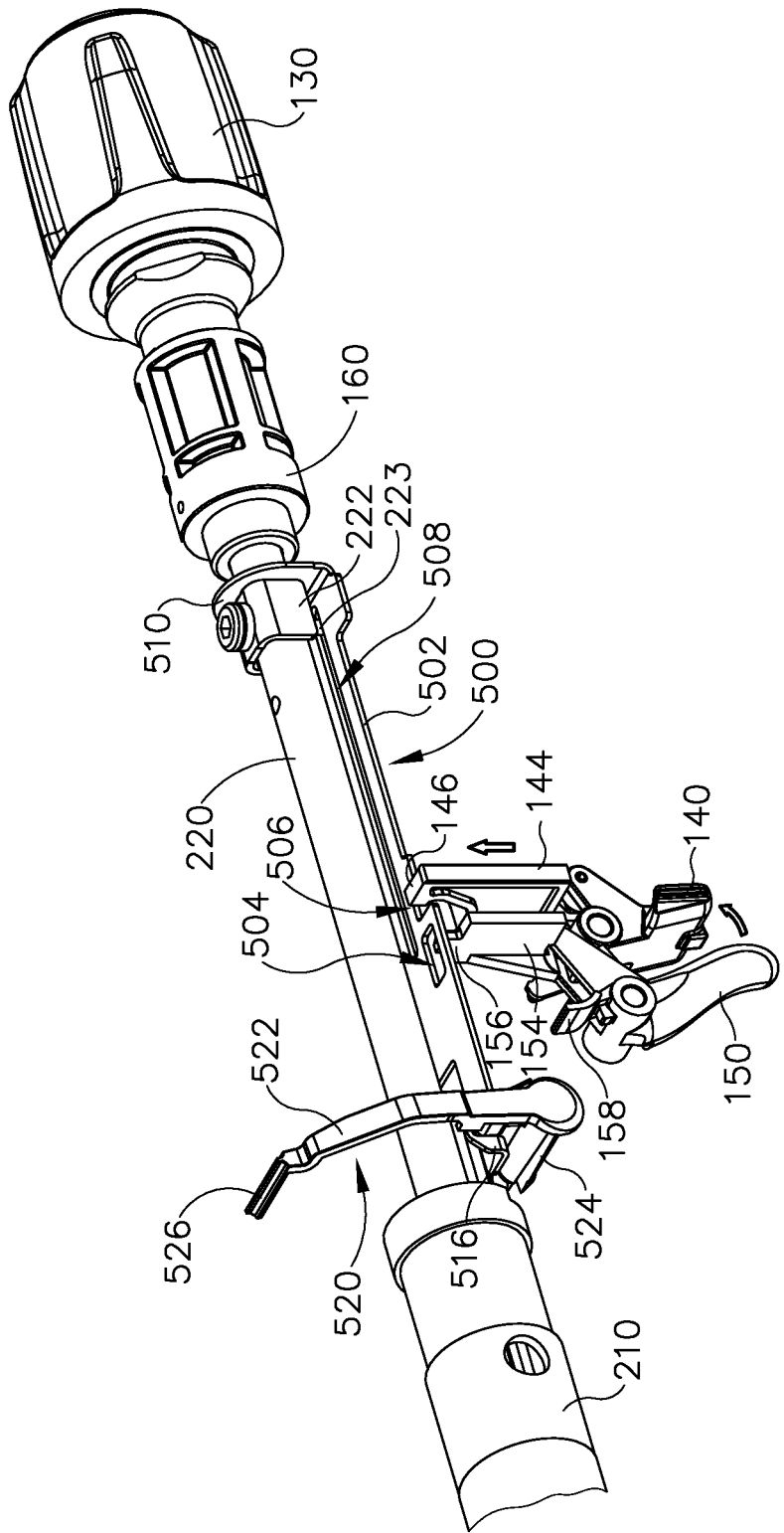
FIG. 12D depicts a perspective view of the anvil actuation assembly of FIG. 12A, with a safety trigger pivoted from a first position to a second position.

As shown in FIG. 12D, upper end (146) passes through slot (506) as safety trigger (140) is pivoted from the position shown in FIG. 12C to the position shown in FIG. 12D. It should be understood that this movement of upper end (146) would not be possible at the stages shown in FIGS. 12A-12B (when the gap distance (d) is too great) because body (502) would physically block upward movement of upright member (144), thereby physically blocking pivotal movement of safety trigger (140). In the present example, a cap (not shown) incorporated into knob (130) prevents knob (130) from rotating to a point where anvil (400) would be retracted too far proximally (such that the gap distance (d) is too small). In some other variations, even if knob (130) were to permit anvil (400) to be retracted too far proximally (such that the gap distance (d) is too small), body (502) would physically block upward movement of upright member (144), thereby physically blocking pivotal movement of safety trigger (140), in the event that the operator retracts trocar (330) and anvil (400) too far proximally (such that the gap distance (d) is too small). Regardless of whether body (502), knob (130), or some other feature prevents actuation when the gap distance (d) would be too small, it should be understood that instrument (10) permits actuation of safety trigger (140) only when the gap distance (d) is within the clinically acceptable range.

Figure 12E:
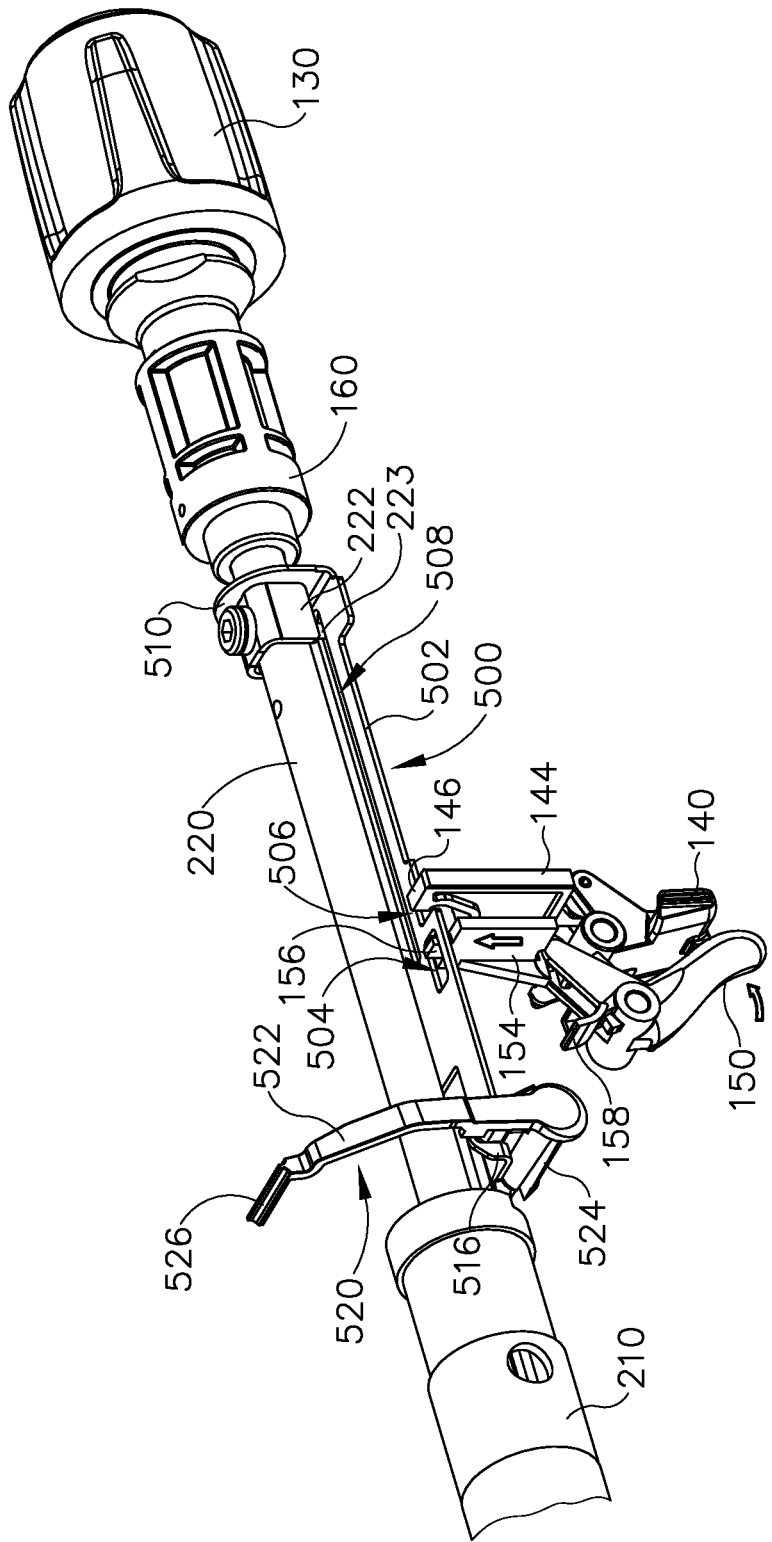
FIG. 12E depicts a perspective view of the anvil actuation assembly of FIG. 12A, with a firing trigger pivoted from a first position to a second position.
Figure 13:
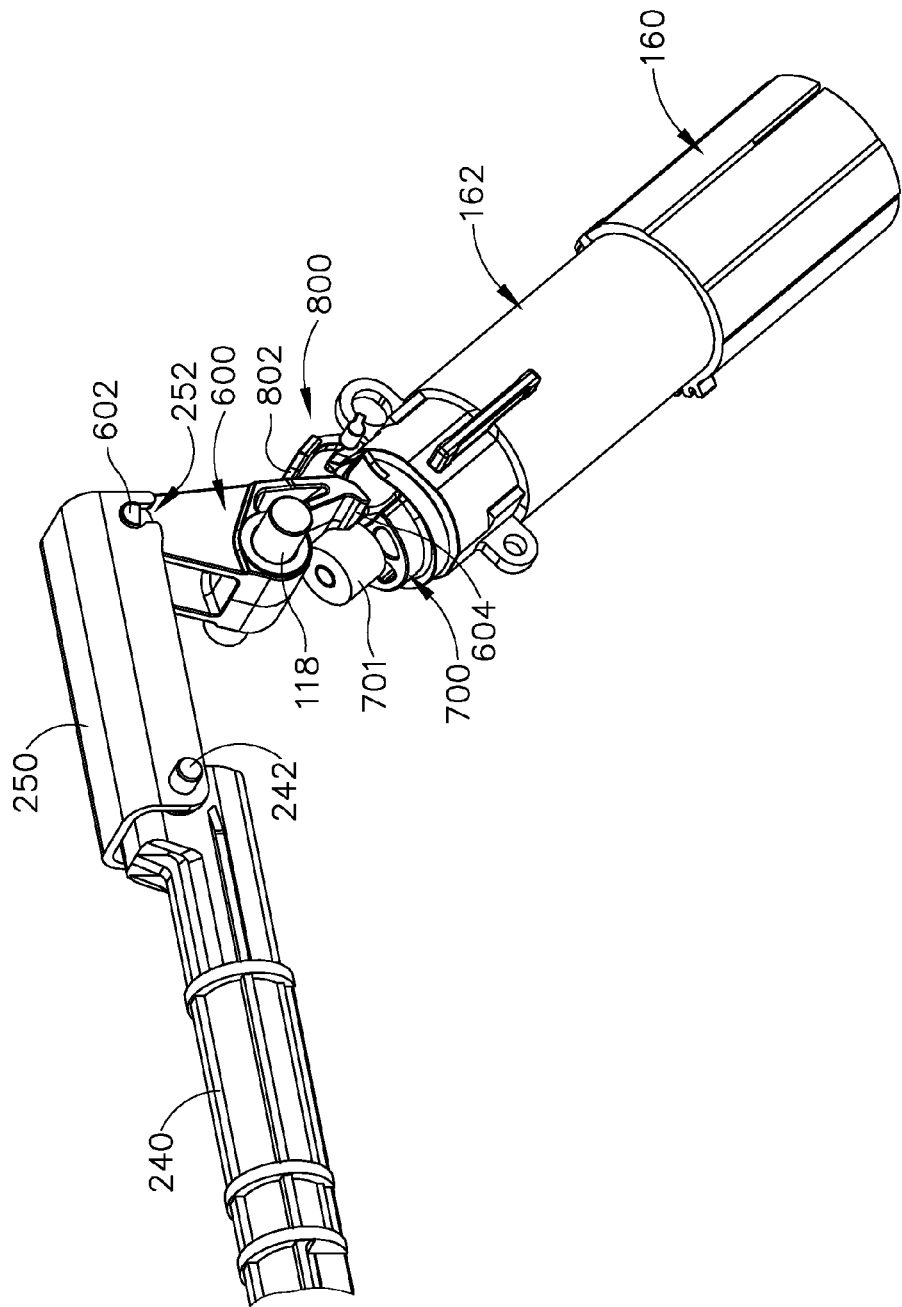
FIG. 13 depicts a perspective view of a stapling head actuation assembly of the circular stapler of FIG. 1.

As noted above, safety trigger (140) is configured to prevent actuation of firing trigger (150) until safety trigger (140) has been actuated. Once safety trigger (140) has been actuated, the operator may actuate firing trigger (150) from the position shown in FIG. 12D to the position shown in FIG. 12E. As shown in FIG. 12E, upper end (156) passes through slot (504) as firing trigger (150) is pivoted from the position shown in FIG. 12D to the position shown in FIG. 12E. It should be understood that, even in the complete absence of safety trigger (140), this movement of upper end (156) would not be possible at the stages shown in FIGS. 12A-12B (when the gap distance (d) is too great) because body (502) would physically block upward movement of upright member (154), thereby physically blocking pivotal movement of firing trigger (150). It should also be understood that body (502) would also physically block upward movement of upright member (154), thereby physically blocking pivotal movement of firing trigger (150), in the event that the operator retracts trocar (330) and anvil (400) too far proximally (such that the gap distance (d) is too small). Thus, even in the complete absence of safety trigger (140), firing trigger (150) may only be actuated when the gap distance (d) is within the clinically acceptable range.

Firing trigger (150) of the present example includes an integral actuation paddle (158). Paddle (158) pivots forwardly as firing trigger (150) pivots from the position shown in FIG. 12D to the position shown in FIG. 12E. Paddle (158) is configured to actuate a switch of a motor activation module (180), which is shown in FIG. 9, when firing trigger (150) pivots from the position shown in FIG. 12D to the position shown in FIG. 12E. Motor activation module (180) is in communication with battery pack (120) and motor (160), such that motor activation module (180) is configured to provide activation of motor (160) with electrical power from battery pack (120) in response to paddle (158) actuating the switch of motor activation module (180). Thus, motor (160) will be activated when firing trigger (150) is pivoted from the position shown in FIG. 12D to the position shown in FIG. 12E. This activation of motor (160) will actuate stapling head assembly (300) as described in greater detail below.

3. Exemplary Stapling Head Actuation Assembly

FIGS. 13-20D show various components that are operable to actuate stapling head assembly (300). These components include motor (160), a gearbox (162), a rotary cam member (700), a cam follower (600), drive bracket (250) and stapling head assembly driver (240). Gearbox (162) is coupled with a drive shaft of motor (160) and is further coupled with cam member (700). Activation of motor (160) thus causes rotation of cam member (700) via gearbox (162). Various suitable configurations that may be used for gearbox (162) will be apparent to those of ordinary skill in the art in view of the teachings herein. Cam member (700) is configured to interact with cam follower (160) to pivot cam follower (160) in two angular directions about a pin (118) as will be described in greater detail below. Pin (118) is coupled with casing (110). A bushing (701) provides rotary support to cam member (700) relative to casing (110).

Figure 14:
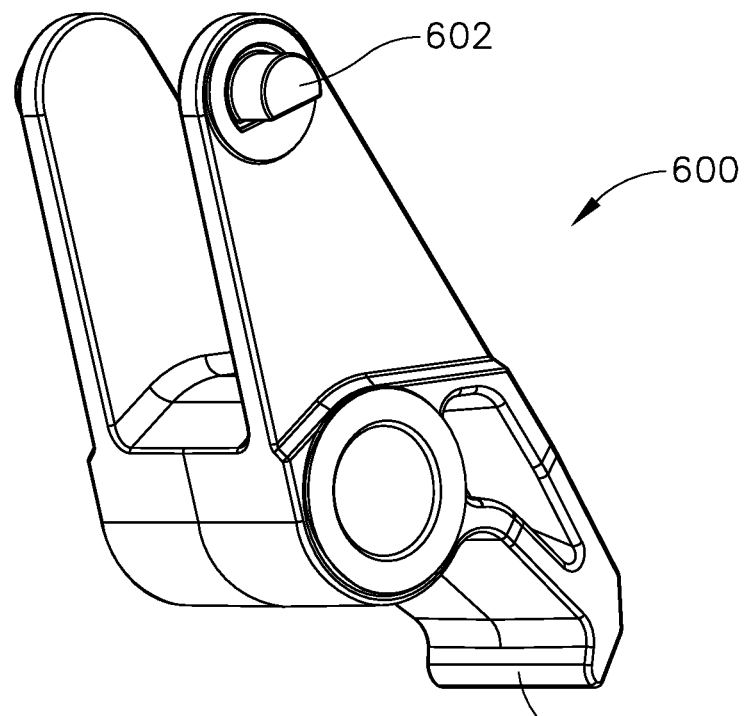
FIG. 14 depicts a perspective view of a cam follower of the stapling head actuation assembly of FIG. 13.
Figure 15:
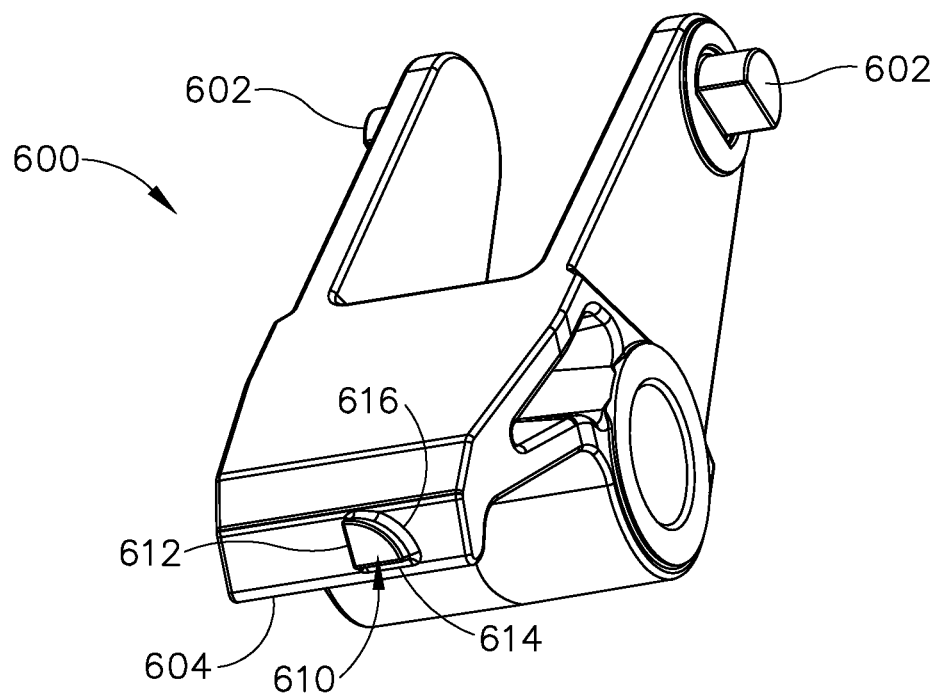
FIG. 15 depicts another perspective view of the cam follower of FIG. 14.

Cam follower (600) is pivotably coupled with drive bracket (250) via a pair of integral pins (602), which are received in complementary notches (252) of drive bracket (250). As shown in FIGS. 14-15, cam follower (600) includes a first bearing feature (604) and a second bearing feature (610). First bearing feature (604) consists of a rounded, horizontally extending surface. Second bearing feature (610) is shaped like a quarter-pie defined by a straight vertical surface (612), a horizontally extending surface (614), and a curved surface (616). Second bearing feature (610) projects proximally relative to first bearing feature (504).

Figure 16:
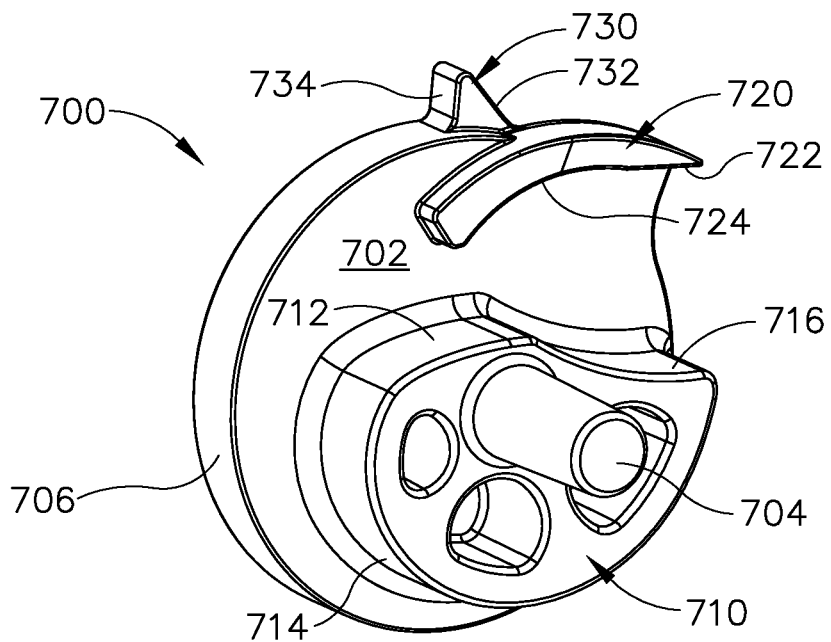
FIG. 16 depicts a perspective view of a rotary cam of the stapling head actuation assembly of FIG. 13.
Figure 17:
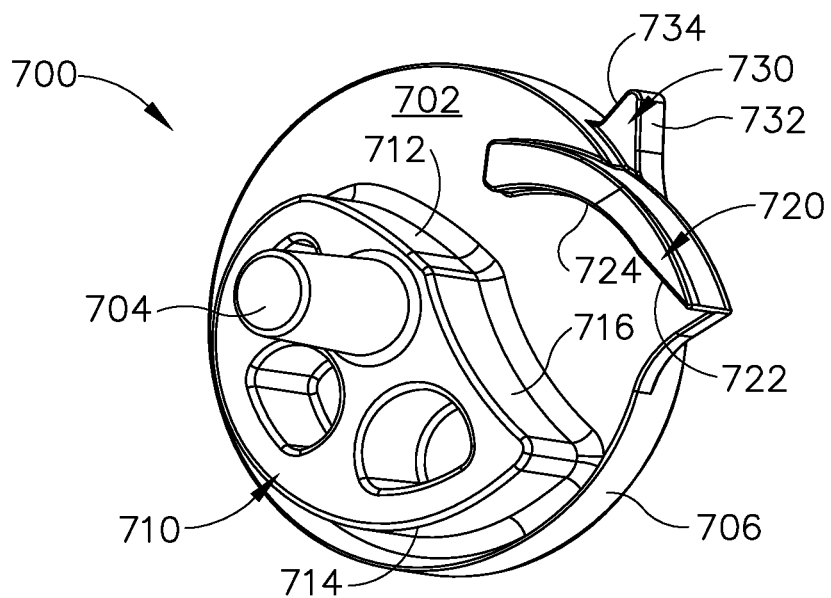
FIG. 17 depicts another perspective view of the rotary cam of FIG. 16.

FIGS. 16-17 show cam member (700) in greater detail. Cam member (700) comprises a distal face (702), a distally projecting post (704), and an outer circumferential surface (706). A first cam feature (710) and a second cam feature (720) project distally from distal face (702). Post (704) engages bushing (701). First cam feature (710) comprises a first surface region (712), a second surface region (714), and a third surface region (716). First surface region (712) is convexly defined by a relatively large radius of curvature, such that first surface region (712) is nearly flat. Second surface region (714) is convexly defined by a progressively increasing radius of curvature. Third surface region (716) is concavely defined by a relatively large radius of curvature. In addition to projecting distally from distal face (702), second cam feature (720) projects outwardly from outer circumferential surface (706). Second cam feature (720) includes a first surface region (722) and a second surface region (724). First surface region (722) is substantially flat while second surface region (724) is concavely curved. The origin of the radius of curvature for each curved surface region (712, 714, 716, 724) is offset from the center of post (704).

Figure 18A:
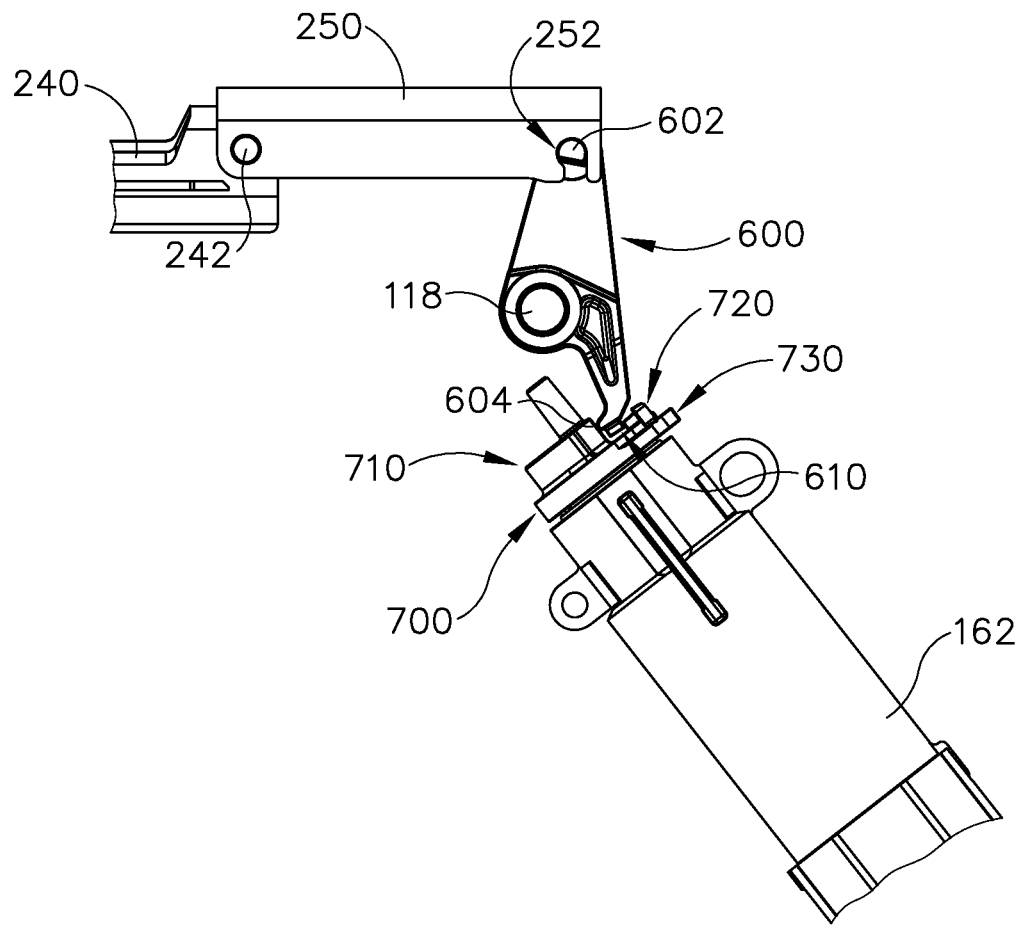
FIG. 18A depicts a side elevational view of the stapling head actuation assembly of FIG. 13, with the rotary cam in a first angular position and the cam follower in a first pivotal position.
Figure 18B:
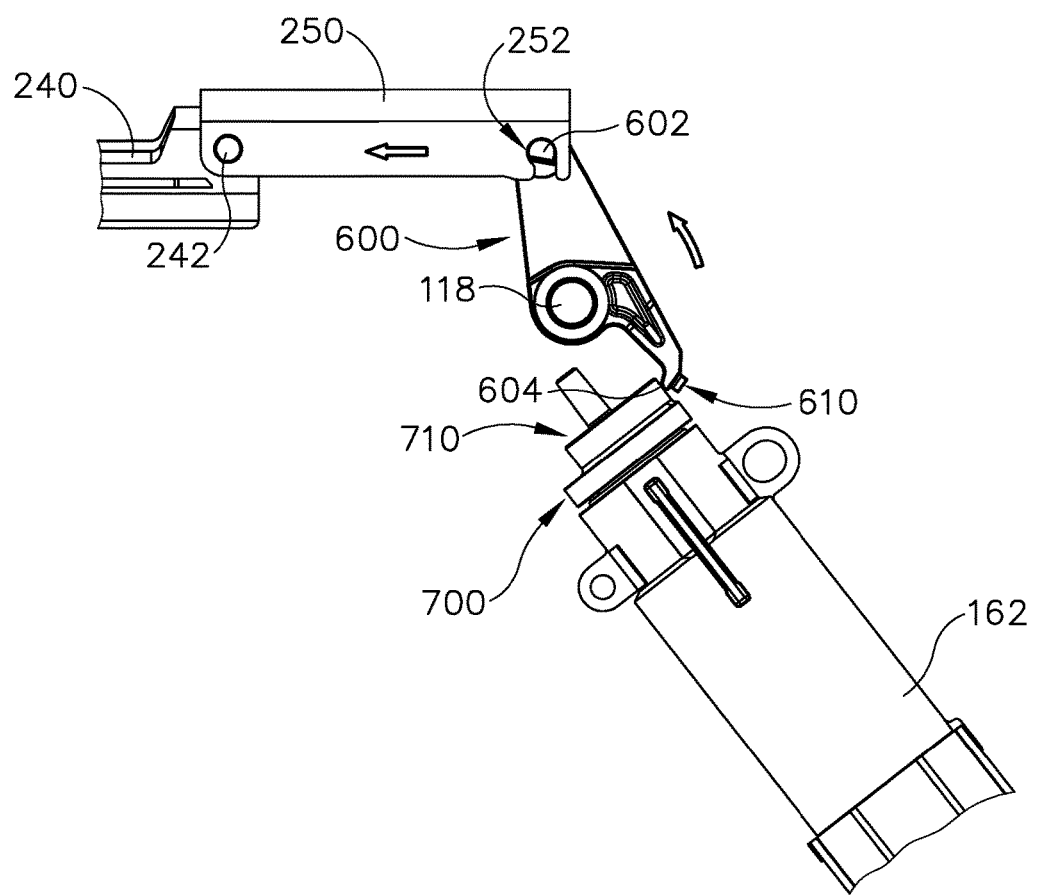
FIG. 18B depicts a side elevational view of the stapling head actuation assembly of FIG. 13, with the rotary cam in a second angular position and the cam follower in a second pivotal position.

FIGS. 18A-18B show the general interaction between cam follower (600) and first and second cam features (710, 720), though this interaction will be described in greater detail below with reference to FIGS. 20A-20D. As cam member (700) is rotated from the position shown in FIG. 18A to the position shown in FIG. 18B, first cam feature (710) bears against first bearing feature (604) of cam follower (600), causing cam follower to pivot about pin (118). In the view shown in FIGS. 18A-18B, cam follower (600) pivots counterclockwise as cam member (700) is rotated from the position shown in FIG. 18A to the position shown in FIG. 18B. As can be seen in the transition from FIG. 18A to FIG. 18B, this counterclockwise pivoting of cam follower (600) drives drive bracket (250) and stapling head assembly driver (240) distally, thereby actuating stapling head assembly (300). As cam member (700) continues to rotate in the same direction back toward the position shown in FIG. 18A, second cam feature (720) engages and bears against second bearing feature (610) of cam follower (600), causing cam follower (600) to pivot clockwise about pin (118). This clockwise pivoting of cam follower (600) about pin (118) retracts drive bracket (250) and stapling head assembly driver (240) proximally back toward the position shown in FIG. 18A.

Figure 19A:
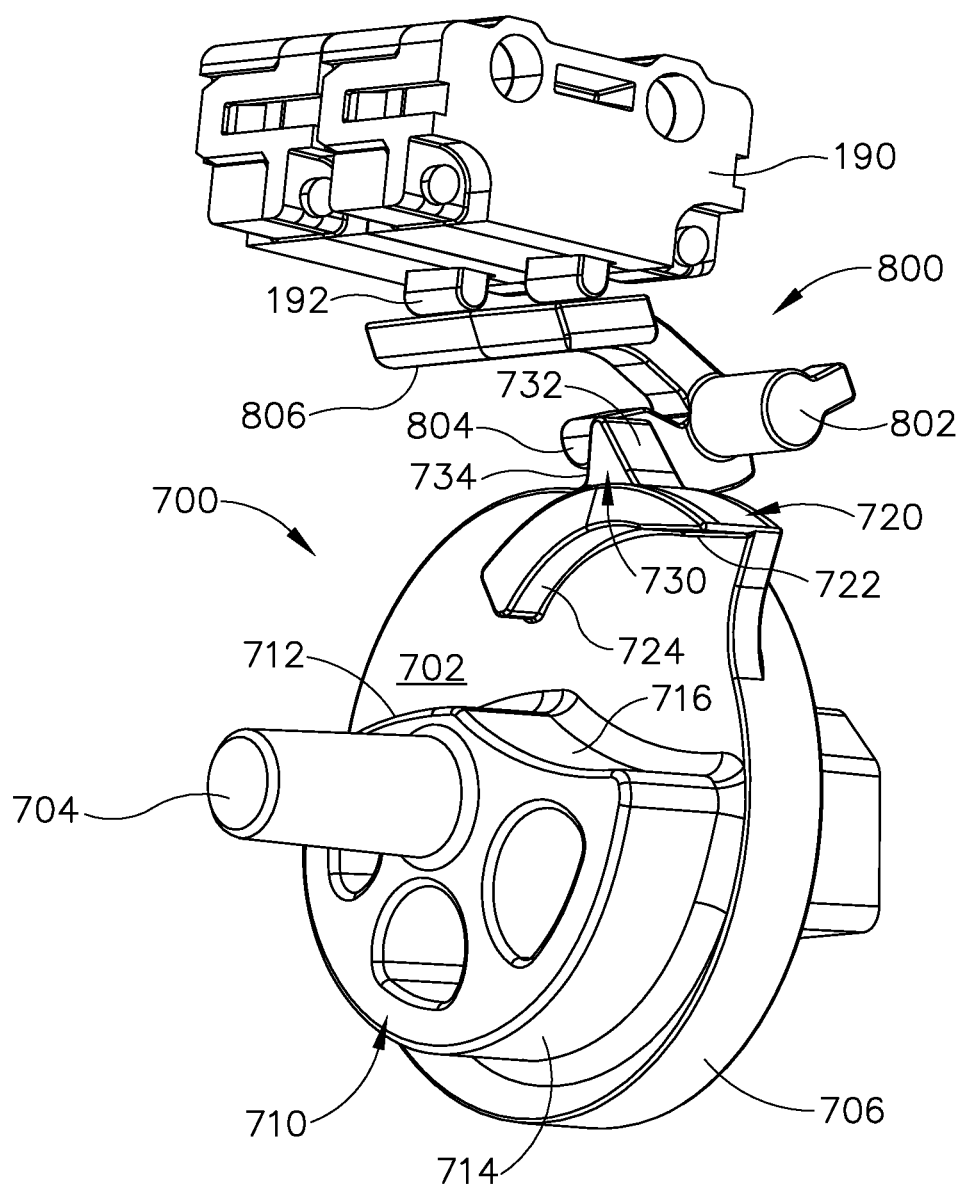
FIG. 19A depicts a perspective view of the rotary cam of FIG. 16, a rocker member, and a stop switch, with the rotary cam in a first angular position and the rocker member in a first pivotal position.
Figure 19B:
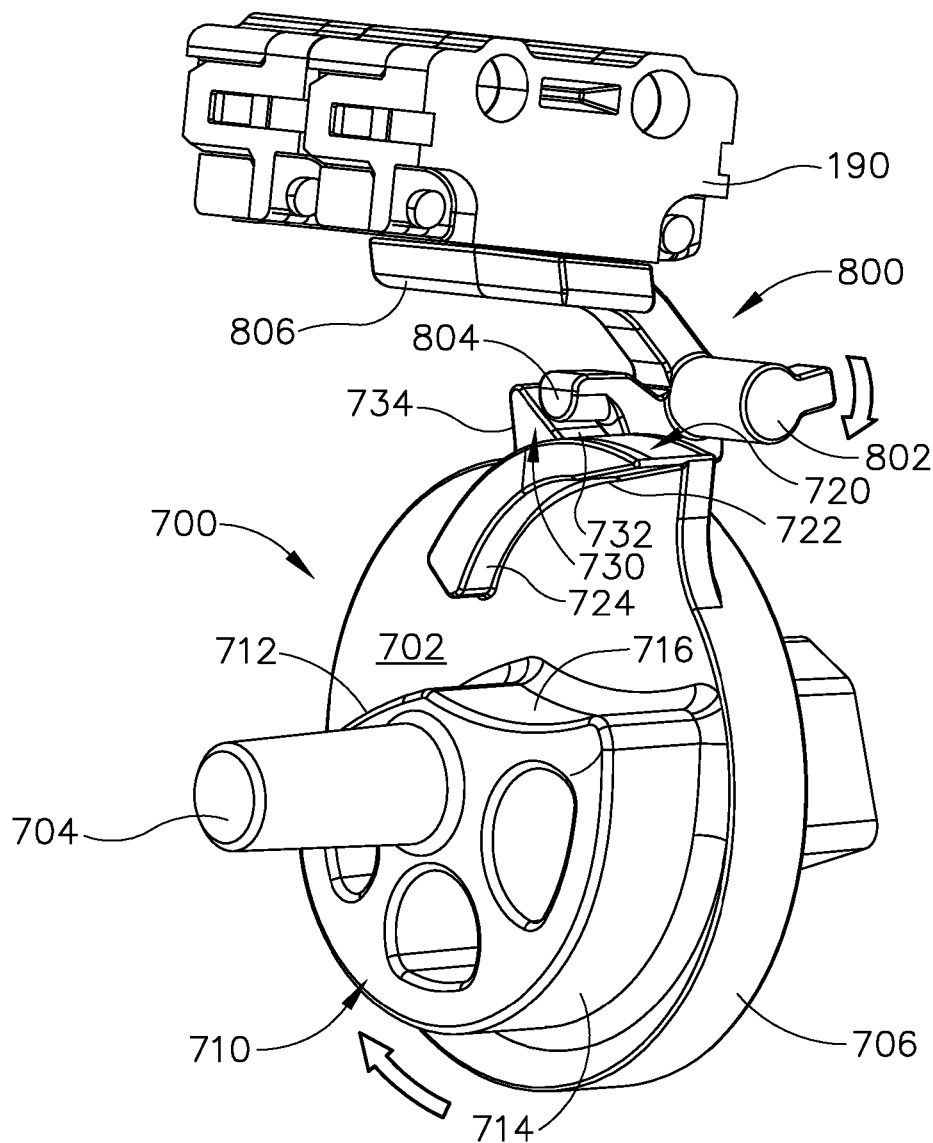
FIG. 19B depicts a perspective view of the rotary cam of FIG. 16, the rocker member of FIG. 19A, and the stop switch of FIG. 19A, with the rotary cam in a fourth angular position and the rocker member in a second pivotal position.

Referring back to FIGS. 16-17, a third cam feature (730) projects outwardly from outer circumferential surface (706). Third cam feature (730) comprises a first surface region (732) and a second surface region (734). First surface region (732) is flat and is oriented generally tangentially relative to outer circumferential surface (706). Second surface region (732) is also flat and is oriented radially outwardly relative to outer circumferential surface (706). Third cam feature (730) is configured to interact with a rocker member (800) as shown in FIGS. 19A-19B. Rocker member (800) comprises an integral pin (802), a bearing member (804), and a paddle (806). Pin (802) is pivotably coupled with casing (110), such that rocker member (800) is pivotable within casing (110) about the longitudinal axis defined by pin (802). Bearing member (804) is configured to interact with third cam feature (730) as will be described in greater detail below. Paddle (806) is configured to actuate a switch button (192) of a short circuit module (190) as will also be described in greater detail below.

FIG. 19A shows cam member (700) in the same position as shown in FIG. 18A. At this stage, second surface region (734) of third cam feature (730) is adjacent to bearing member (804) of rocker member (800). FIG. 19B shows cam member (700) in a position where cam member (700) has been rotated past the position shown in FIG. 18B and back toward the position shown in FIG. 18A. However, cam member (700) has not completed a full revolution. At the stage shown in FIG. 19B, first surface region (732) has engaged and borne against bearing member (804), thereby pivoting rocker member (800) about the longitudinal axis defined by pin (802). This has caused paddle (806) to actuate switch button (192) of short circuit module (190). Short circuit module (190) is configured to prevent motor (160) from further activation when switch button (192) has been actuated. In some versions, short circuit module (190) couples battery pack (120) with a power sink, in addition to short circuiting motor (160), when switch button (192) is actuated. This may result in discharge of battery pack (120) in addition to stopping activation of motor (160) once an actuation stroke of stapling head assembly (300) has been completed. By way of example only, short circuit module (190) may be configured and operable in accordance with at least some of the teachings of U.S. Pub. No. 2015/0083774, now U.S. Pat. No. 9,907,552, issued Mar. 6, 2018, the disclosure of which is incorporated by reference herein. Other suitable configurations will be apparent to those of ordinary skill in the art in view of the teachings herein.

Figure 20A:
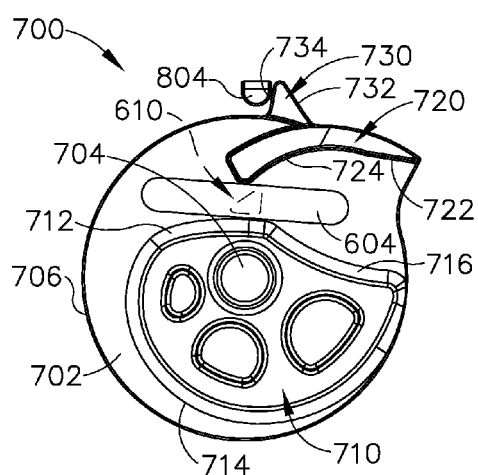
FIG. 20A depicts a schematic end view of the rotary cam of FIG. 16, the cam follower of FIG. 14, and the rocker member of FIG. 19A, with the rotary cam in the first angular position, the cam follower in the first pivotal position, and the rocker member in the first pivotal position.
Figure 20B:
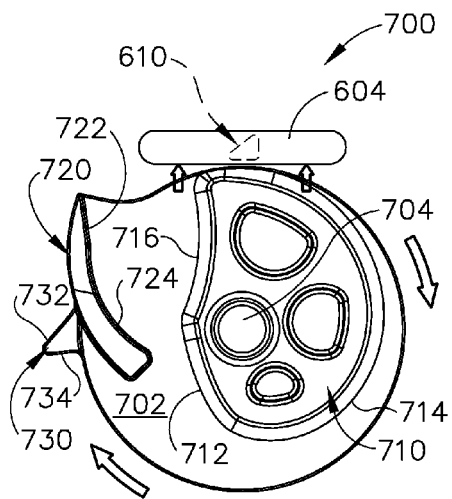
FIG. 20B depicts a schematic end view of the rotary cam of FIG. 16 and the cam follower of FIG. 14, with the rotary cam in the second angular position, the cam follower in the second pivotal position, and the rocker member of FIG. 19A in the first pivotal position.

FIGS. 20A-20D schematically depict the interaction between cam member (700), features of cam follower (600), and features of rocker member (800) as cam member (700) rotates. It should be understood that the rotation of cam member (700) throughout the stages shown in FIGS. 20A-20D is driven by motor (160) and gearbox (162). FIG. 20A shows cam member (700) in the same position as shown in FIGS. 18A and 19A. At this stage, first bearing feature (604) of cam follower (600) is positioned on first surface region (712) and bearing member (804) or rocker member (800) is adjacent to second surface region (734) of third cam feature (730). Also at this stage, knife member (340) and staple driver member (350) are in proximal positions, such that stapling head assembly (300) is in a non-actuated state. As cam member (700) is rotated to the position shown in FIG. 20B, second surface region (714) bears against bearing member (804), thereby driving bearing member (804) upwardly. This causes cam follower (600) to pivot about pin (118) to the position shown in FIG. 18B. Cam follower (600) thus drives knife member (340) and staple driver member (350) distally via drive bracket (250) and stapling head assembly driver (240). Stapling head assembly (300) is thus in an actuated state at the stage shown in FIG. 20B. In some versions, cam member (700) rotates through an angular range of approximately 270° in order to transition stapling head assembly (300) from the non-actuated state to the actuated state.

Figure 20C:
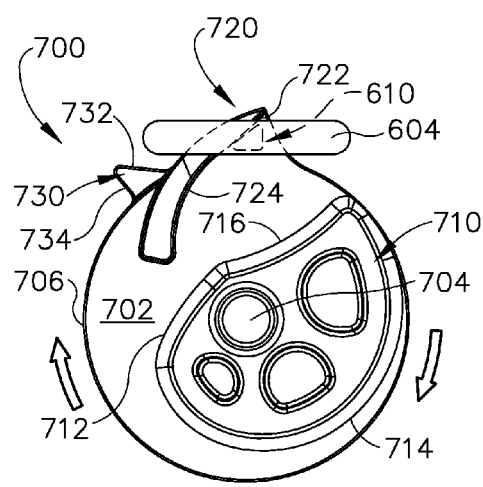
FIG. 20C depicts a schematic end view of the rotary cam of FIG. 16 and the cam follower of FIG. 14, with the rotary cam in a third angular position, the cam follower in the second pivotal position, and the rocker member of FIG. 19A in the first pivotal position.
Figure 20D:
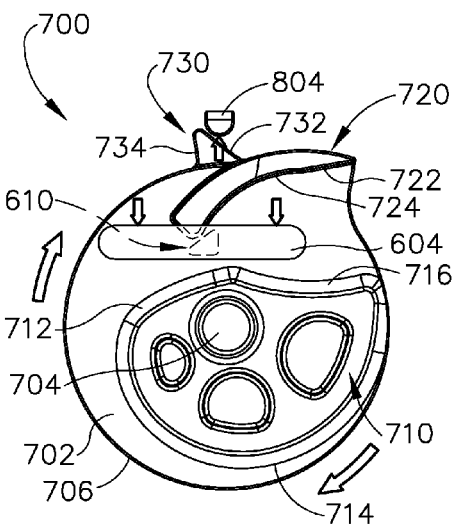
FIG. 20D depicts a schematic end view of the rotary cam of FIG. 16, the cam follower of FIG. 14, and the rocker member of FIG. 19A, with the rotary cam in a fourth angular position, the cam follower in a third pivotal position, and the rocker member in a second pivotal position.

After stapling head assembly (300) has been actuated, cam member (700) continues to rotate to the position shown in FIG. 20C. At this stage, first surface region (722) of second cam member (720) begins to engage curved surface (616) of second bearing feature (610) of cam follower (600). As cam member (700) continues to rotate to the position shown in FIG. 20D, second surface region (724) engages curved surface (616) of second bearing feature (610), driving second bearing feature (610) downwardly. This causes cam follower (600) to pivot about pin (118) back from the position shown in FIG. 18B toward the position shown in FIG. 18A. Cam follower (600) thus drives knife member (340) and staple driver member (350) proximally via drive bracket (250) and stapling head assembly driver (240). In addition, first surface region (732) has engaged and borne against bearing member (804), thereby pivoting rocker member (800) about the longitudinal axis defined by pin (802) at the stage shown in FIG. 20D. Rocker member (800) is thus in the same state in FIG. 20D as shown in FIG. 19B. Short circuit module (190) has thus been actuated at the stage shown in FIG. 20D.

It should be understood from the foregoing that cam member (700) is operable to drive knife member (340) and staple driver member (350) distally, then drive knife member (340) and staple driver member (350) proximally and actuate short circuit module (190) by rotating in a single angular direction through the range of motion shown in FIGS. 20A-20D. Other suitable ways in which knife member (340), staple driver member (350), and short circuit module (190) may be actuated will be apparent to those of ordinary skill in the art in view of the teachings herein.

E. Exemplary Anastomosis Procedure

Figure 21A:
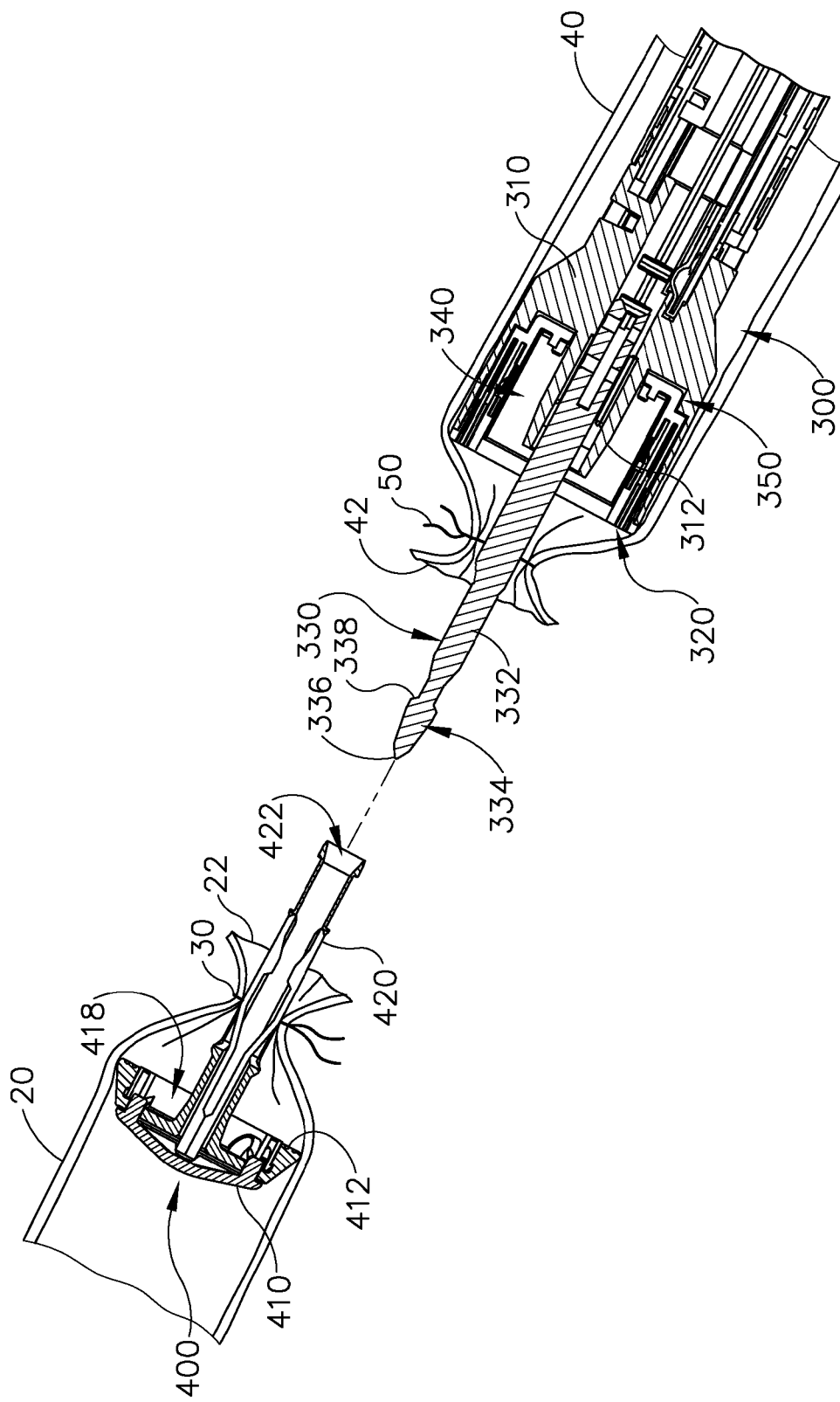
FIG. 21A depicts a cross-sectional side view of the anvil of FIG. 3 positioned within a first section of a digestive tract and the stapling head assembly of FIG. 6 positioned in a second section of the digestive tract, with the anvil separated from the stapling head assembly.

FIGS. 21A-21E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. As shown in FIG. 21A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 21A-21E is an open surgical procedure, though the procedure may instead be performed laparoscopically. Various suitable ways in which instrument (10) may be used to form an anastomosis (70) in a laparoscopic procedure will be apparent to those of ordinary skill in the art in view of the teachings herein.

As shown in FIG. 21A, anvil (400) is positioned in tubular anatomical structure (20) such that shank (420) protrudes from the open severed end (22) of tubular anatomical structure (20). A purse-string suture (30) is provided about a mid-region of shank (420) to generally secure the position of anvil (400) in tubular anatomical structure (20). Similarly, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40).

Figure 21B:
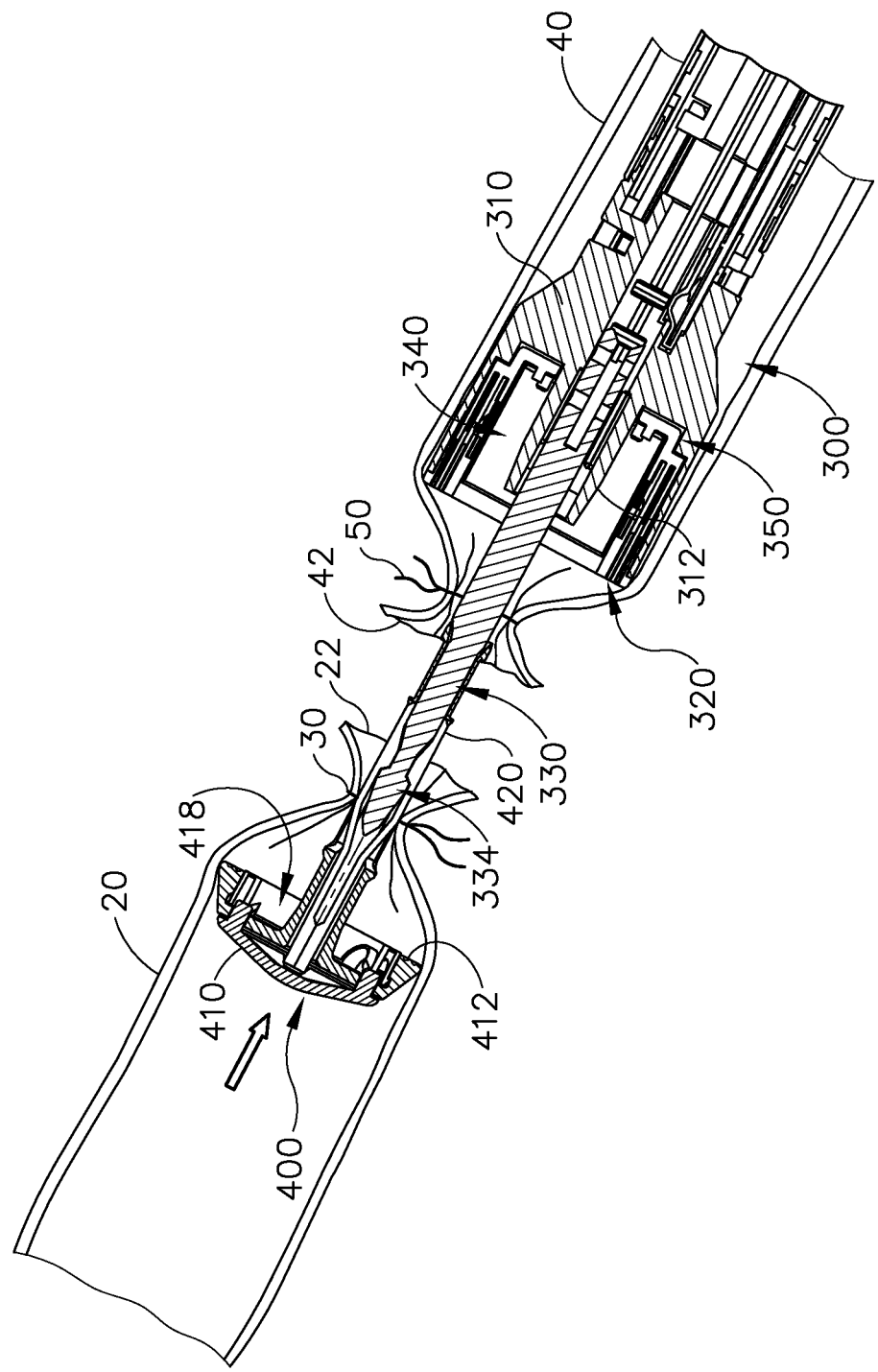
FIG. 21B depicts a cross-sectional side view of the anvil of FIG. 3 positioned within the first section of the digestive tract and the stapling head assembly of FIG. 6 positioned in the second section of the digestive tract, with the anvil secured to the stapling head assembly.

Next, anvil (400) is secured to trocar (330) by inserting trocar (330) into bore (422) as shown in FIG. 21B. Latch members (430) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally (as described above with reference to FIGS. 12A-12C). As shown in FIG. 21C, this proximal retraction of trocar (330) and anvil (400) compresses the tissue of tubular anatomical structures (20, 40) between surfaces (412, 322) of anvil (400) and stapling head assembly (300). The operator observes the position of needle (526) within window (114) to determine whether the gap distance (d) between opposing surfaces (412, 322) of anvil (400) and stapling head assembly (300) is appropriate; and makes any necessary adjustments via knob (130).

Figure 21D:
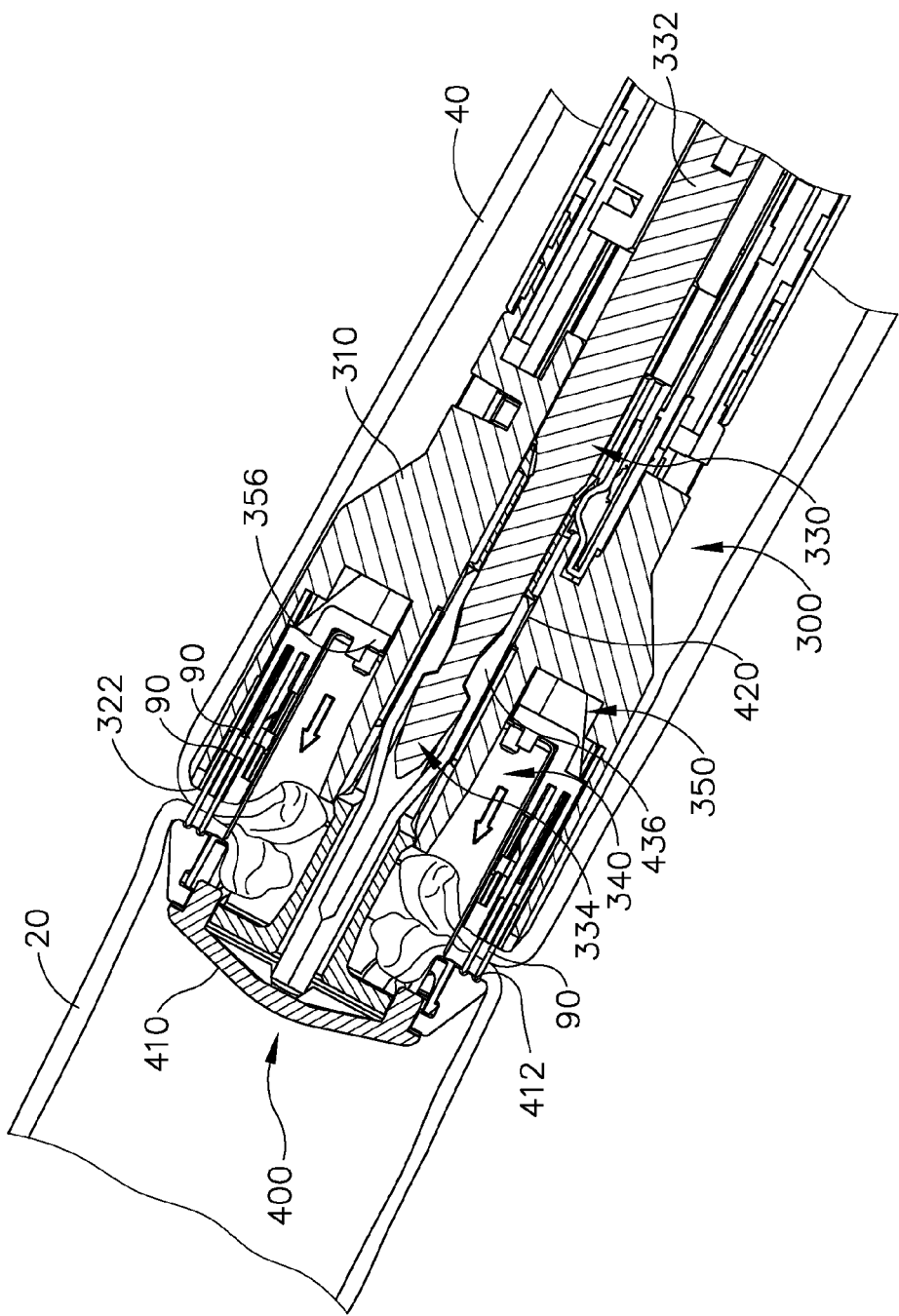
FIG. 21D depicts a cross-sectional side view of the anvil of FIG. 3 positioned within the first section of the digestive tract and the stapling head assembly of FIG. 6 positioned in the second section of the digestive tract, with the stapling head assembly actuated to sever and staple the clamped tissue.

Once the operator has appropriately set the gap distance (d) via knob (130), the operator actuates safety trigger (140) (as shown in FIG. 12D) to enable actuation of firing trigger (150). The operator then actuates firing trigger (150) (as shown in FIG. 12D). This causes paddle (158) to actuate the switch of a motor activation module (180), thereby activating motor to rotate cam member (700) (as shown in FIGS. 20A-20D). This rotation of cam member (700) actuates stapling head assembly (300) by driving knife member (340) and staple driver member (350) distally as shown in FIG. 21D. As knife member (340) translates distally, cutting edge (342) of knife member (340) cooperates with inner edge (416) of anvil (400), thereby shearing excess tissue that is positioned within annular recess (418) of anvil (400) and the interior of knife member (340).

As shown in FIG. 4, anvil (400) of the present example includes a breakable washer (417) within annular recess (418). This washer (417) is broken by knife member (340) when the knife member (340) completes a full distal range of motion from the position shown in FIG. 21C to the position shown in FIG. 21D. The progressively increasing radius of curvature of second surface region may provide an increasing mechanical advantage as knife member (340) reaches the end of its distal movement, thereby providing greater force by which to break the washer (417). Of course, the breakable washer (417) may be omitted entirely in some versions. In versions where washer (417) is included, it should be understood that washer (417) may also serve as a cutting board for knife member (340) to assist in cutting of tissue. Such a cutting technique may be employed in addition to or in lieu of the above-noted shearing action between inner edge (416) and knife member (340).

As staple driver member (350) translates distally from the position shown in FIG. 21C to the position shown in FIG. 21D, staple driver member (350) drives staples (90) through the tissue of tubular anatomical structures (20, 40) and into staple forming pockets (414) of anvil (400). Staple forming pockets (414) deform the driven staples (90) into a "B" shape as is known in the art. The formed staples (90) thus secure the ends of tissue together.

Figure 21E:
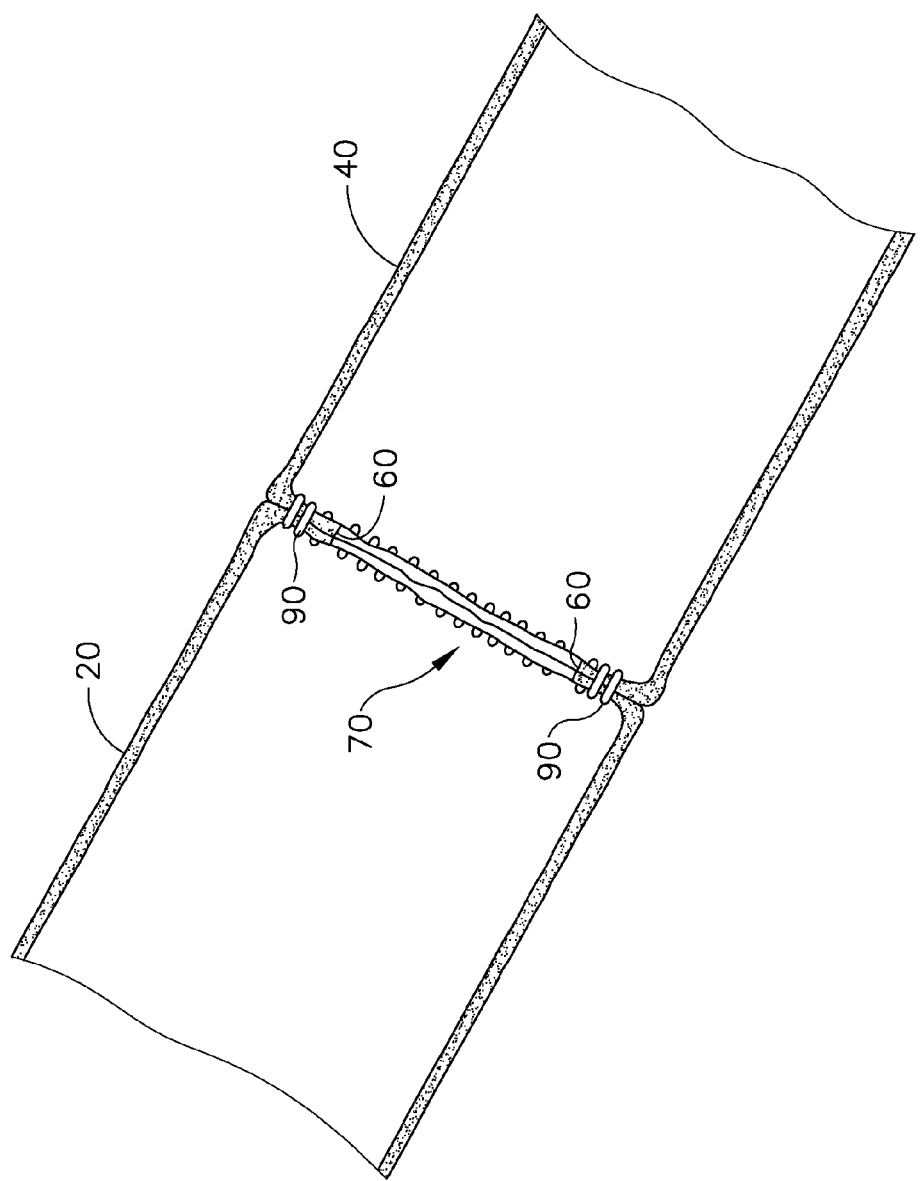
FIG. 21E depicts a cross-sectional side view of the first and second sections of the digestive tract of FIG. 21A joined together at an end-to-end anastomosis.

After the operator has actuated stapling head assembly (300) as shown in FIG. 21D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400)

still secured to trocar (330). Referring back to the example where the tubular anatomical structures (20, 40) comprise sections of a patient's colon, instrument (10) may be removed via the patient's rectum. With instrument (10) is removed, the tubular anatomical structures (20, 40) are left secured together by two annular arrays of staples (90) at an anastomosis (70) as shown in FIG. 21E. The inner diameter of the anastomosis (70) is defined by the severed edge (60) left by knife member (340).

II. Exemplary "Readiness" Indicators

In some versions of instrument (10) it may desirable to provide instrument (10) with features that are configured to indicate the "readiness" of instrument (10) to actuate stapling head assembly (300). For instance, such features may indicate any one or more of the following conditions: whether battery pack (120) is appropriately attached; whether anvil (400) is appropriately attached with stapling head assembly (300); whether the gap distance (d) between opposing surfaces (412, 322) of anvil (400) and stapling head assembly (300) is appropriate; and/or whether battery pack (120) has sufficient charge to complete actuation of stapling head assembly (300). In addition, features may be provided to prevent actuation of stapling head assembly (300) unless instrument (10) is "ready" and/or to prevent subsequent actuation of stapling head assembly (300) after a single use. For instance, such features may cause the charge to be drained from battery pack (120) after a first use of battery pack (120) so as to prevent subsequent use of battery pack (120). Various examples of such features will be described in greater detail below; while other examples will be apparent to those of ordinary skill in the art in view of the teachings herein. Moreover, the following teachings may be applied to devices that are used in various other contexts.

A. Exemplary Rotation Knob Lockout Features

Figure 22:
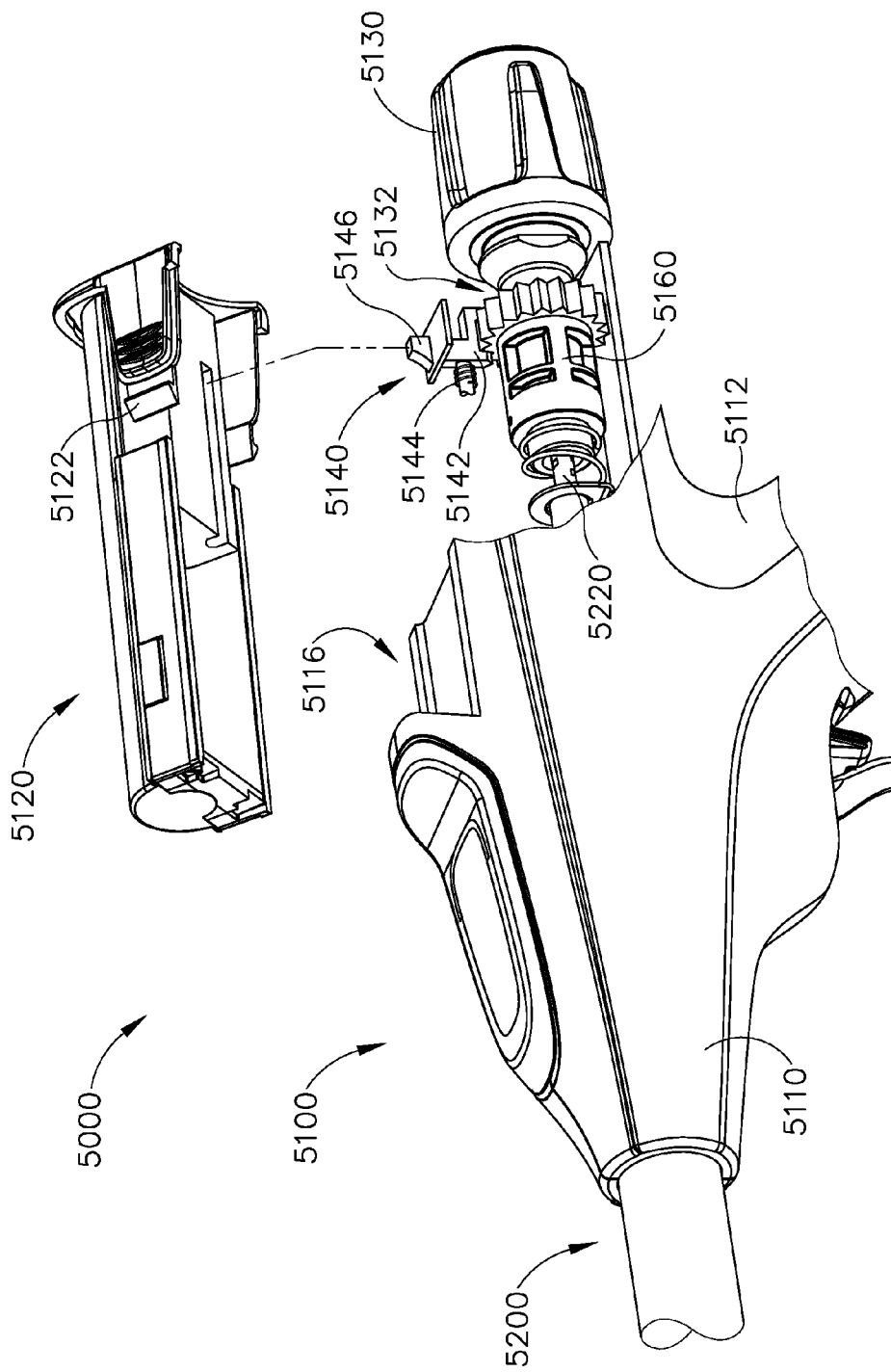
FIG. 22 depicts a perspective view of a handle assembly of an exemplary alternative circular stapler.
Figure 23A:
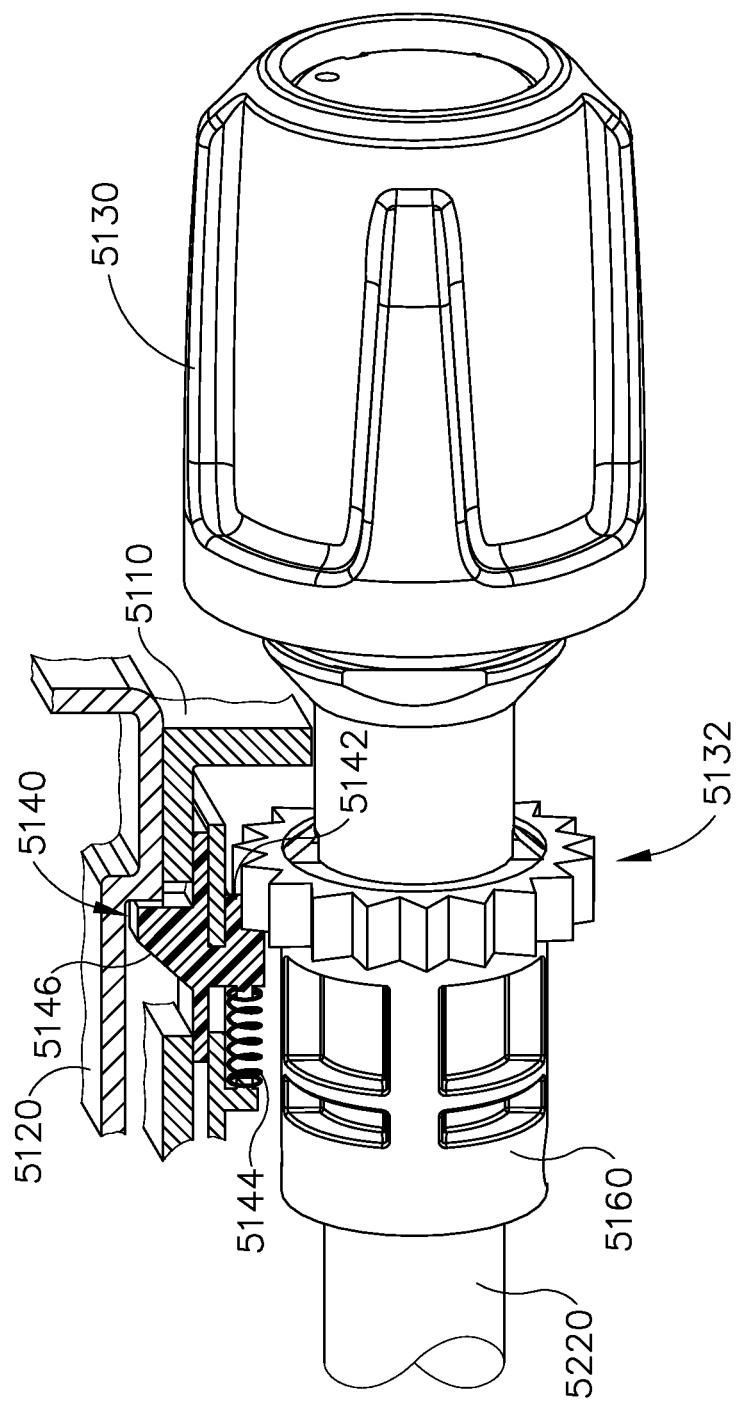
FIG. 23A depicts a detailed cross-sectional side view of the handle assembly of FIG. 22 with a battery pack of the handle assembly in a proximal position.
Figure 23B:
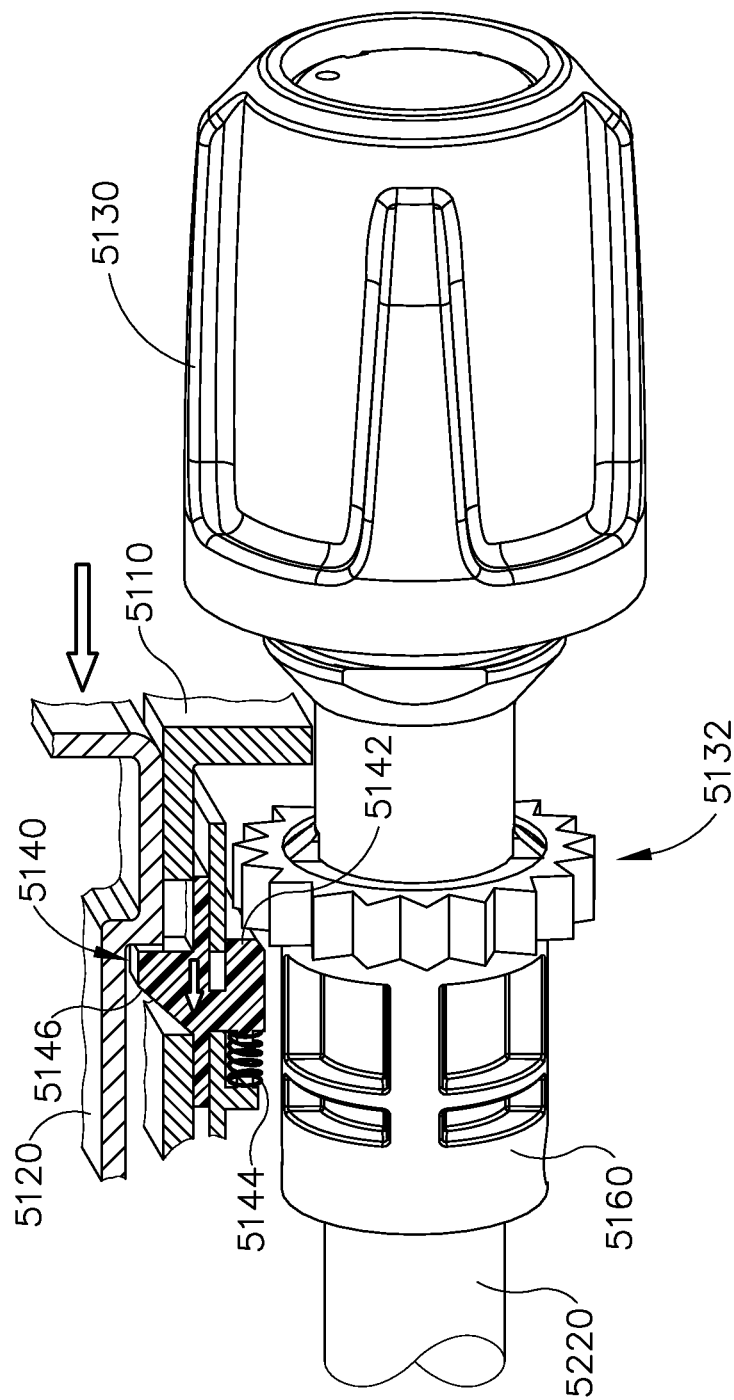
FIG. 23B depicts a detailed cross-sectional side view of the handle assembly of FIG. 23A with the battery pack of FIG. 23A moved to a distal position.

FIGS. 22-23B show an exemplary surgical circular stapling instrument (5000) that is configured to operate substantially similar to instrument (10) discussed above except for any differences discussed below. For instance, instrument (5000) may be used to provide an end-to-end anastomosis between two sections of an anatomical lumen such as a portion of a patient's digestive tract. Instrument (5000) of this example comprises a handle assembly (5100), a shaft assembly (5200), a stapling head assembly (not shown), and an anvil (not shown). Instrument (5100) of the present example further includes a battery pack (5120) that is configured to operate substantially similar to battery pack (120) discussed above except for any differences discussed below. Battery pack (5120) is removable from handle assembly (5100). In particular, battery pack (5120) may be inserted into a socket (5116) defined by casing (5110). Once battery pack (5120) is fully inserted in socket (5116), latches (5122) of battery pack (5120) may resiliently engage interior features of casing (5110) to provide a snap fit.

Handle assembly (5100) comprises a casing (5110) defining an obliquely oriented pistol grip (5112). A knob (5130) at the proximal end of handle assembly (5100) is rotatable relative to casing (5110) to provide precise clamping of the tissue between the anvil and the stapling head assembly as discussed above with reference to knob (130) of instrument (10). In particular, a nut (5160) is secured to the distal end of knob (5130). In the present example, nut (5160) is fixedly secured to the distal end of knob (5130) such that nut (5160) will rotate unitarily with knob (5130). Nut (5160) and knob (5130) are configured to cooperate with a trocar actuation rod (5220) to thereby translate trocar actuation rod (5220) longitudinally relative to casing (5110) in response to rotation of nut (5160) and knob (5130) relative to casing (5110). As discussed above with reference to instrument (10), a trocar (not shown) will translate longitudinally relative to shaft assembly (5200) in response to translation of trocar actuation rod (5220) relative to outer shaft assembly (5200) and casing (5110).

Nut (5160) of this example comprises a plurality of outwardly extending teeth (5132) that are disposed in an array that is angularly spaced about an exterior circumference of nut (5160). As will be discussed in more detail below, teeth (5132) of nut (5160) are configured to engage a lockout sled (5140) of handle assembly (5100) to thereby prevent rotation of knob (5130) in the absence of battery pack (5120) or when battery pack (5120) is not properly secured in socket (5116) of handle assembly (5100). Lockout sled (5140) is slidably secured to an interior of casing (5110) within handle assembly (5100) such that lockout sled (5140) is translatable between a proximal position (FIG. 23A) and a distal position (FIG. 23B). A spring (5144) biases lockout sled (5140) toward the proximal position.

As shown in FIG. 23A, in the absence of battery pack (5120) or when battery pack (5120) is not properly secured in socket (5116), with lockout sled (5140) in the proximal position, a lower flange (5142) of lockout sled (5140) engages teeth (5132) of nut (5160) to thereby prevent rotation of knob (5130).

As shown in FIG. 23B, when battery pack (5120) is properly secured in socket (5116), contact between battery pack (5120) and an upper flange (5146) lockout sled (5140) drives lockout sled (5140) distally against the bias of spring (5144) into the distal position. In the distal position, lower flange (5142) of lockout sled (5140) disengages teeth (5132) of nut (5160) so as to permit rotation of knob (5130). It should therefore be appreciated that in the absence of battery pack (5120) or when battery pack (5120) is not properly secured in socket (5116) of handle assembly (5100), the trocar cannot be translated longitudinally relative to shaft assembly (5200); and when battery pack (5120) is properly secured in socket (5116), the trocar can be translated longitudinally relative to shaft assembly (5200).

B. Exemplary Pinhole Indicator

Figure 24:
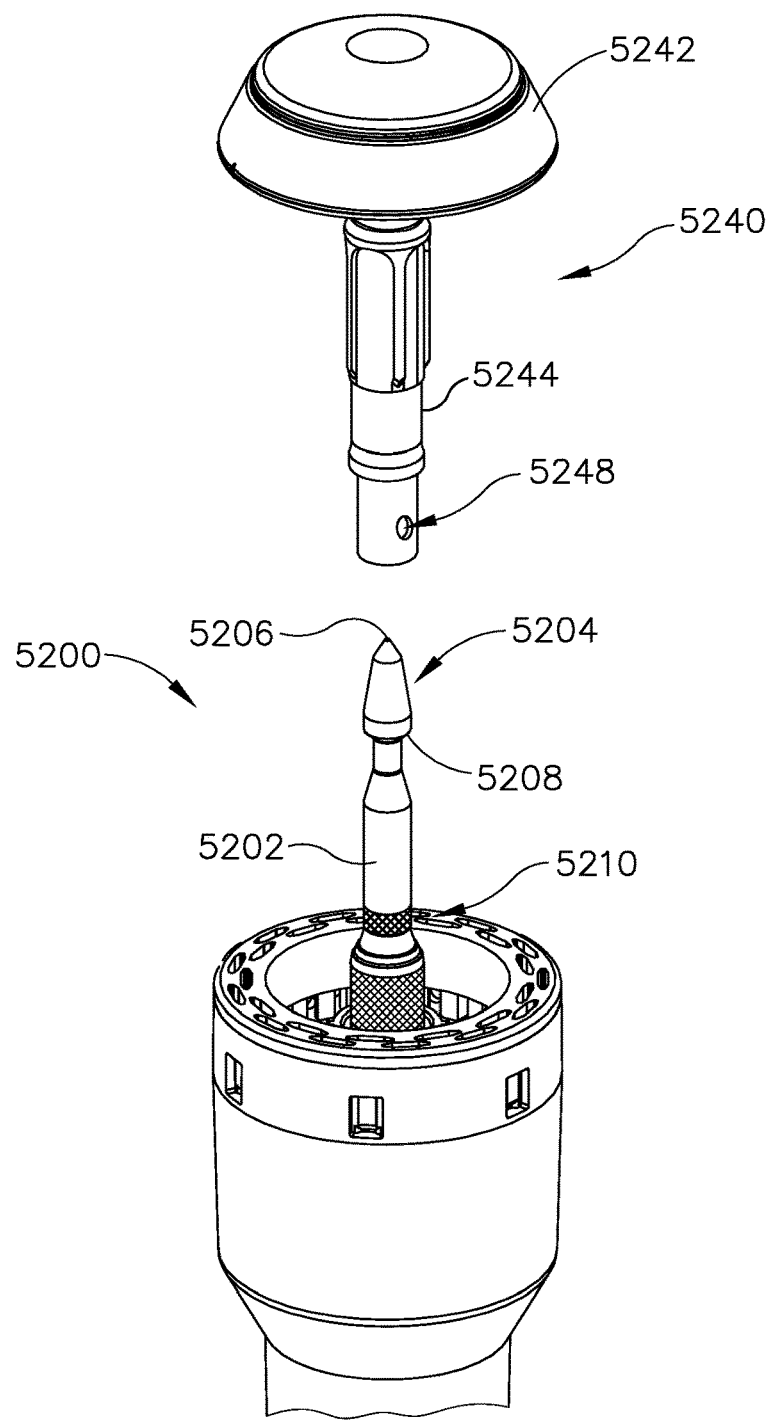
FIG. 24 depicts a perspective view of the distal end of another exemplary alternative circular stapler with an anvil of the circular stapler spaced apart from a trocar of the circular stapler.
Figure 25A:
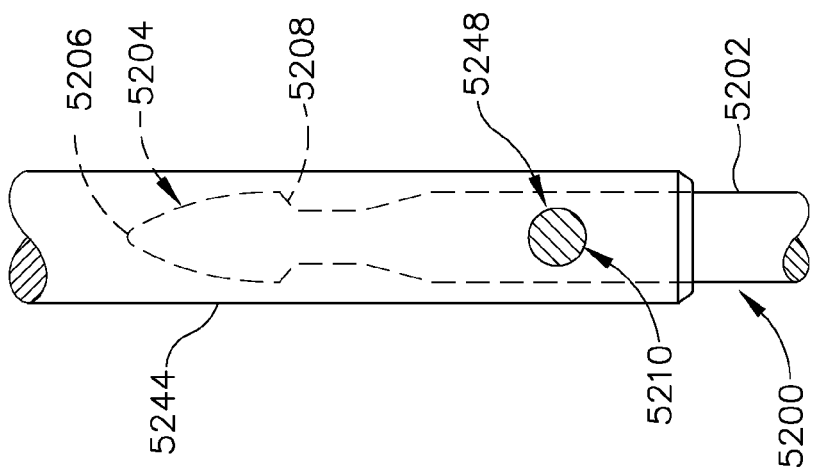
FIG. 25A depicts a side view of the anvil of FIG. 24 in a first position relative to the trocar of FIG. 24.
Figure 25B:
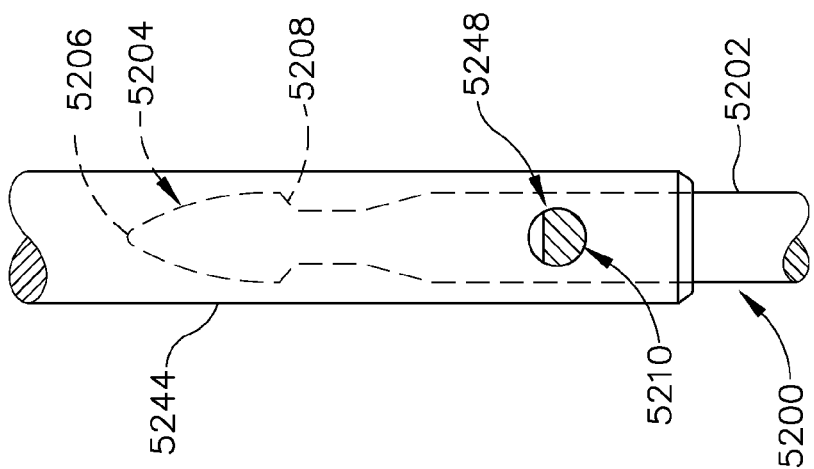
FIG. 25B depicts a side view of the anvil of FIG. 24 in a second position relative to the trocar of FIG. 24.

FIGS. 24-25B show an exemplary trocar (5200) and anvil (5240) that are configured to operate substantially similar to trocar (330) and anvil (400) discussed above respectively except for any differences discussed below. For instance, trocar (5200) is operable to translate distally and proximally relative to tubular casing (310) in response to rotation of knob (130) as discussed above. As will be discussed in more detail below, anvil (5240) is configured to be attached to trocar (5200) such that translation of trocar (5200) relative to tubular casing (310) is communicated directly to anvil (5240) as described above with reference to FIGS. 12A-12C.

Trocar (5200) comprises a shaft (5202) and a head (5204). Head (5204) includes a pointed tip (5206) and an inwardly extending proximal surface (5208). Shaft (5202) thus provides a reduced outer diameter just proximal to head (5204), with surface (5208) providing a transition between that reduced outer diameter of shaft (5202) and the outer diameter of head (5204). While tip (5206) is pointed in the present example, tip (5206) is not sharp. Tip (5206) will thus not easily cause trauma to tissue due to inadvertent contact with tissue. Anvil (5240) of the present example comprises a head (5242) and a shank (5244). Head (5242) includes a proximal surface (not shown) that defines a plurality of staple forming pockets (not shown). Shank (5244) defines a bore (5246). Head (5204) and the distal portion of shaft (5202) are configured for insertion in bore (5246) of anvil (5240). Anvil (5240) is configured to be secured to trocar (5200) in a snap-fit manner when anvil (5240) is fully seated on trocar (5200) as discussed above with reference to instrument (10). In addition to or in lieu of the foregoing, anvil (5240) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

Anvil (5240) includes a pinhole (5248) formed in a sidewall of shank (5244). Pinhole (5248) extends completely through the sidewall of shank (5244) thus providing an operator with visual access through the sidewall of shank (5244) and into bore (5246) of shank (5244). Trocar (5200) includes a marker region (5210) formed in or disposed about an exterior surface of shaft (5202) of trocar (5200). Marker region (5210) is visually distinguishable from the remainder of shaft (5202). For instance, marker region (5210) may comprise a painted region, a decal, and/or a colored band disposed about shaft (5202).

As shown in FIG. 25A, when anvil (5240) is not fully seated on trocar (5200), marker region (5210) is only partially visible via pinhole (5248). In other words, when anvil (5240) is not fully seated on trocar (5200), marker region (5210) extends only partially across the diameter pinhole (5248).

As shown in FIG. 25B, when anvil (5240) is fully seated on trocar (5200), marker region (5210) is completely visible via pinhole (5248). In other words, when anvil (5240) is fully seated on trocar (5200), marker region (5210) extends completely across the diameter pinhole (5248). Thus, it should be understood that pinhole (5248) and marker region (5210) provide an operator with an indication of whether anvil (5240) is fully seated on trocar (5200). It should also be understood that the operator may visualize marker region (5210) through pinhole (5248) directly, endoscopically, or in any other suitable fashion.

C. Exemplary Indicator Latch Members

Figure 26A:
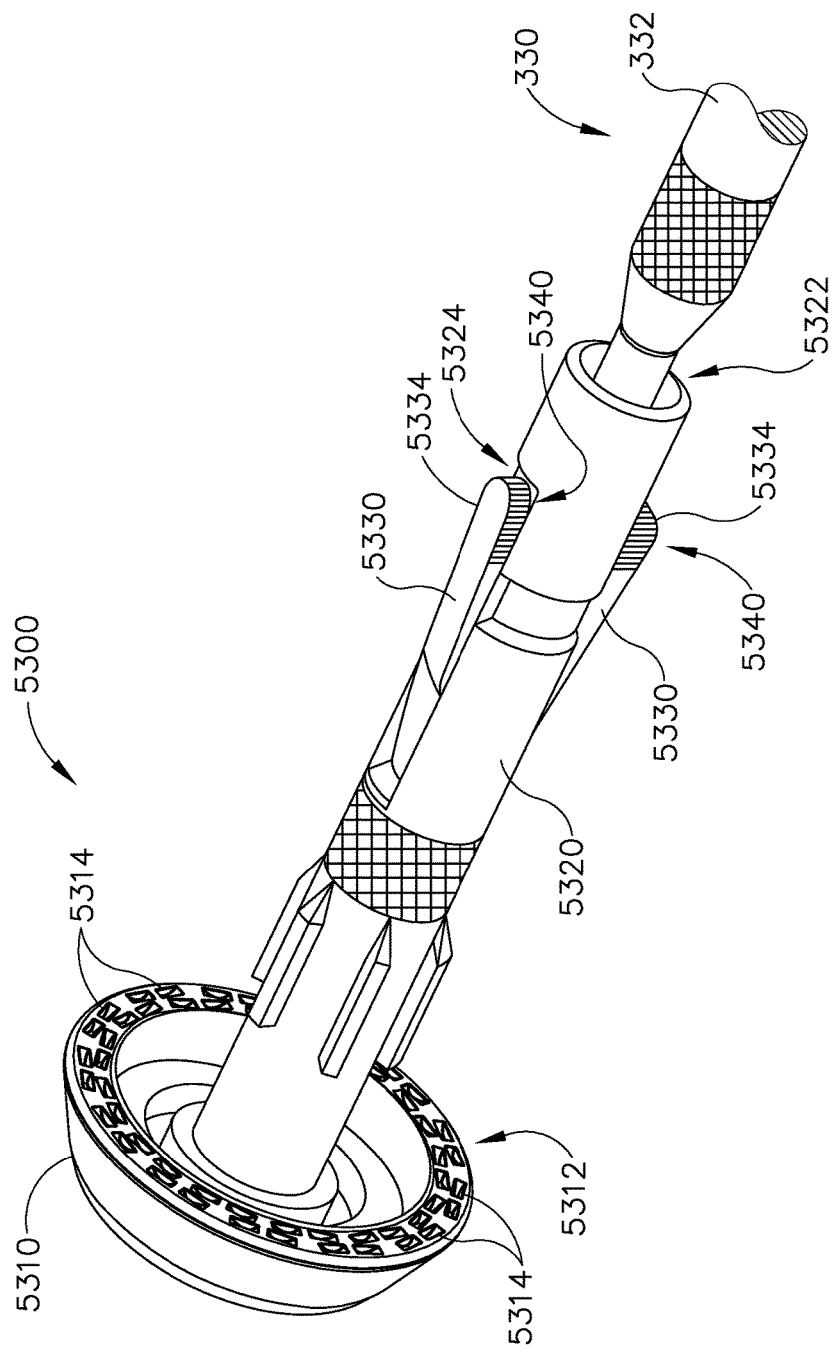
FIG. 26A depicts a perspective view of the distal end of yet another exemplary alternative circular stapler, with an anvil of the circular stapler positioned about a distal end of a trocar of the circular stapler in a distal position, with a pair of indicator tabs extending from an exterior surface of the anvil.
Figure 26B:
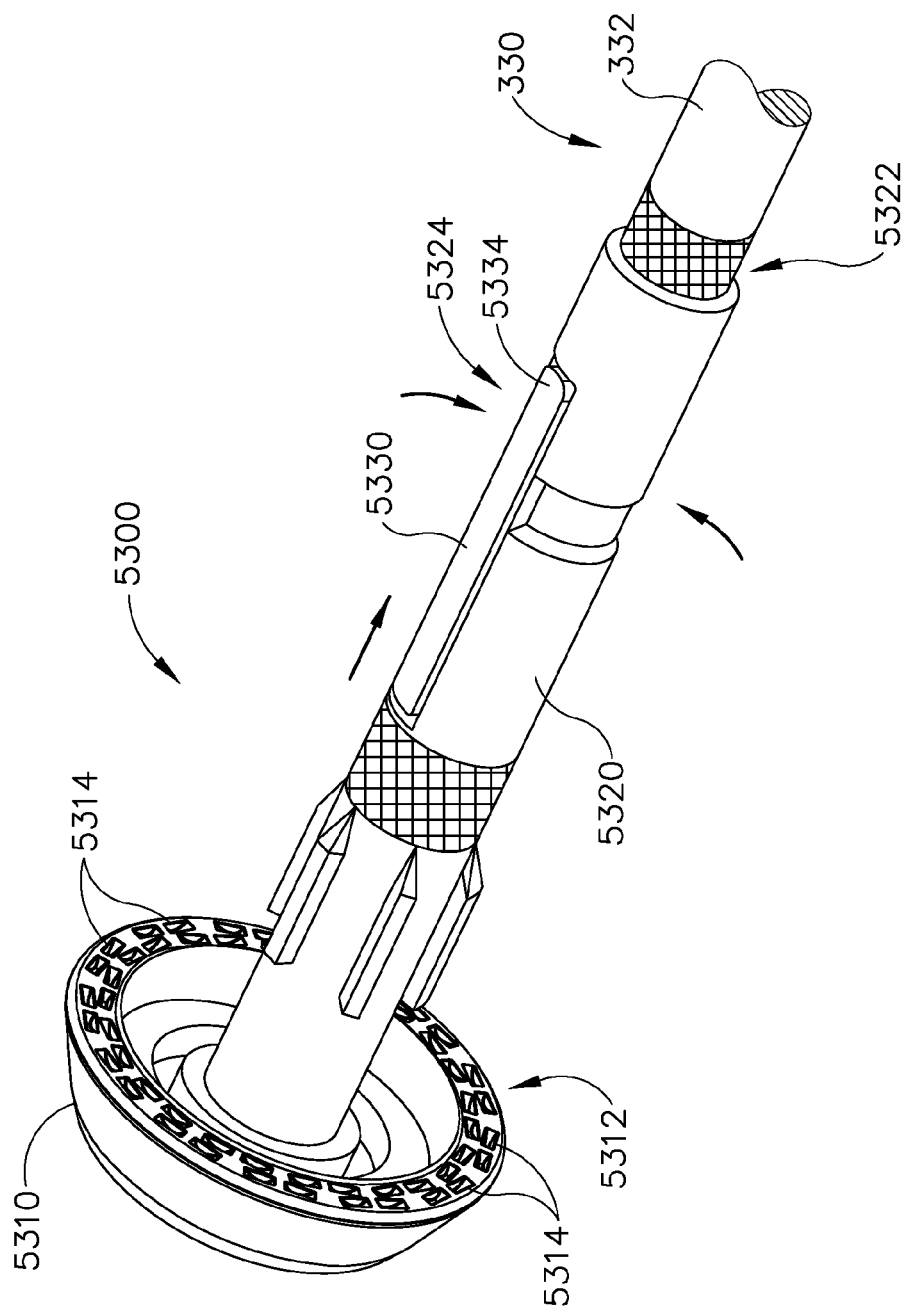
FIG. 26B depicts a perspective view of the distal end of the circular stapler of FIG. 26A, with the anvil of FIG. 26A positioned about a distal end of the trocar of FIG. 26A and moved into a proximal position, with the indicator tabs of FIG. 26A moved inwardly adjacent the exterior surface of the anvil.

FIGS. 26A and 26B show an exemplary anvil (5300) that is configured to operate substantially similar to anvils (400, 5240) discussed above except for any differences discussed below. For instance, anvil (5300) is configured to be attached to trocars (330, 5200) discussed above such that translation of trocars (330, 5200) relative to tubular casing (310) is communicated directly to anvil (5300) as described above with reference to FIGS. 12A-12C.

Anvil (5300) of the present example comprises a head (5310) and a shank (5320). Head (5310) includes a proximal surface (5312) that defines a plurality of staple forming pockets (5314). Staple forming pockets (5314) are arranged in two concentric annular arrays. In some other versions, staple forming pockets (5314) are arranged in three or more concentric annular arrays. Staple forming pockets (5314) are configured to deform staples as the staples are driven into staple forming pockets (5314). For instance, each staple forming pocket (5314) may deform a generally "U" shaped staple into a "B" shape as is known in the art.

Shank (5320) defines a bore (5322) and includes a pair of pivoting latch members (5330) positioned in bore (5322). Latch members (5330) are configured to operate substantially similar to latch members (430) discussed above except for any differences discussed below. Latch members (5330) are positioned within a pair of lateral openings (5324), which are formed through the sidewall of shank (5320). Lateral openings (5324) provide clearance for latch members (5330) to deflect radially outwardly from a longitudinal axis defined by shank (5320) such that latch members (5330) may be passed over head (334) of trocar (330). However, latch members (5330) are configured to resiliently bias distal ends (5334) and latch shelves (not shown) of latch members (5330) radially inwardly toward the longitudinal axis defined by shank (5320). Latch members (5330) thus act as retaining clips. This allows anvil (5300) to be removably secured to a trocars (330, 5240) of stapling head assembly (300). For instance, as discussed above with reference to anvil (400), trocar (330) is configured for insertion in bore (5322) of anvil (5320). Proximal surface (338) of trocar (330) and the latch shelves of latch members (5330) have complementary positions and configurations such that when latch members (5330) deflect radially inwardly, the latch shelves engage proximal surface (338) when shank (5320) of anvil (5300) is fully seated on trocar (330). Anvil (5300) is thus secured to trocar (330) through a snap fit due to latch members (5330).

Distal end (5334) of each latch member (5330) includes a marker region (5340). Marker regions (5340) are visually distinguishable from the remainder of latch members (5330) and shank (5320). For instance, marker regions (5340) may comprise a painted region, a decal, and/or a colored band secured to distal ends (5334). As shown in FIG. 26A, when latch members (5330) are deflected outwardly, marker regions (5340) are exposed relative to shank (5320) and are thus visible to an operator so as to indicate to the operator that anvil (5300) is not fully seated on trocar (330). When anvil (5300) fully seated on trocar (330), latch members (5330) deflect inwardly as discussed above such that marker regions (5340) are obscured by shank (5320) and thus indicate to the operator that anvil (5300) is fully seated on trocar (330). It should be understood that the operator may inspect for the visibility of marker regions (5340) through direct vizualization, endoscopically, or in any other suitable fashion.

In addition to or in lieu of the foregoing, anvil (5300) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

D. Exemplary Anvil with Integral Circuit

Figure 27:
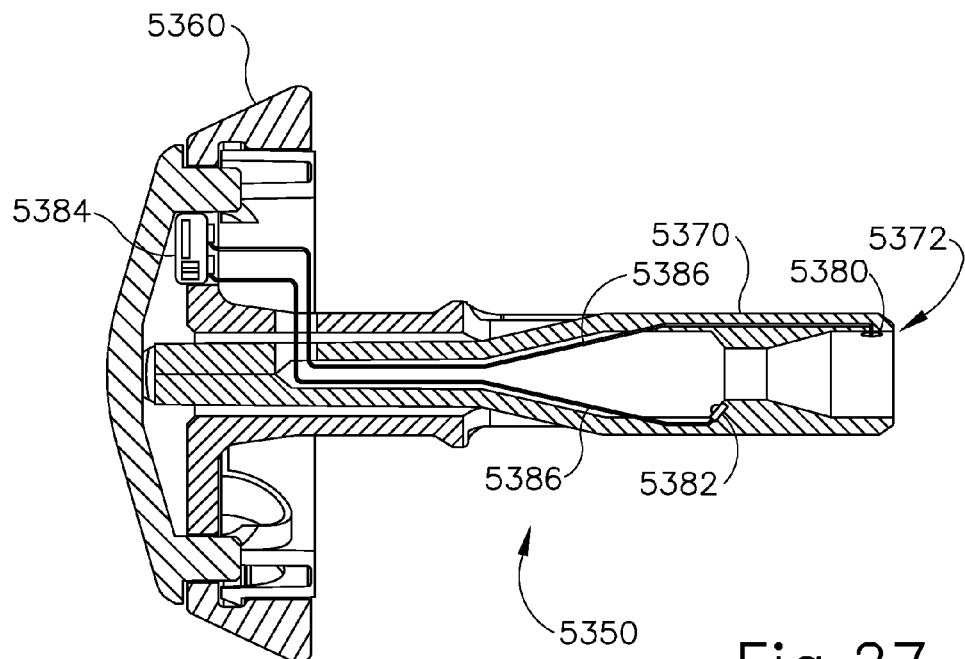
FIG. 27 depicts a cross-sectional side view of an anvil operable for use with any of the circular staplers described herein.
Figure 28:
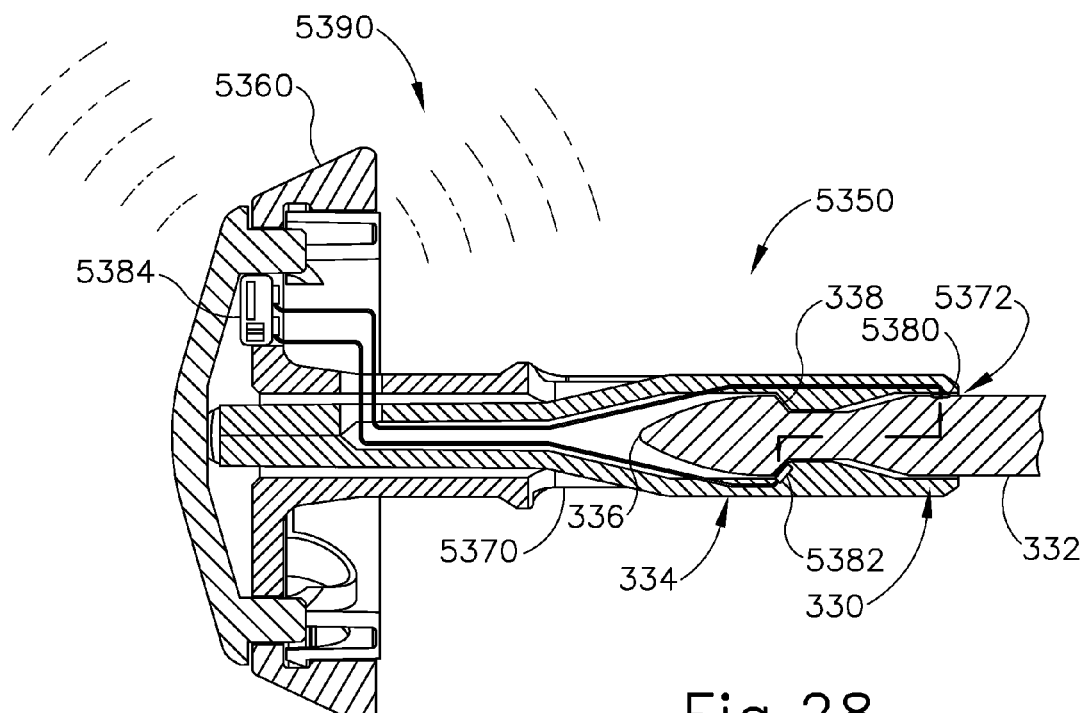
FIG. 28 depicts a cross-sectional side view of the anvil of FIG. 27 positioned about a trocar.

FIGS. 27 and 28 depict an exemplary anvil (5350) that is configured to operate substantially similar to anvils (400, 5240, 5300) discussed above except for any differences discussed below. For instance, anvil (5350) is configured to be attached to trocars (330, 5200) discussed above such that translation of trocars (330, 5200) relative to tubular casing (310) is communicated directly to anvil (5350) as described above with reference to FIGS. 12A-12C.

Anvil (5350) of the present example comprises a head (5360) and a shank (5370). Shank (5370) defines a bore (5372). Anvil (5350) further includes a pair of electrical contact surfaces (5380, 5382) positioned within bore (5372) of shank (5370). Contact surfaces (5380, 5382) are in electrical communication with a transmitter (5384) via wires (5386). As will be discussed in more detail below, transmitter (5384) is configured to emit a signal operable to actuate audible, tactile, and/or visible feedback to an operator indicating proper attachment of anvil (5350) to trocar (330). A first electrical contact surface (5380) is positioned for contact with an exterior surface of shaft (332) of trocar (330). A second electrical contact surface (5382) is positioned for contact with surface (338) of trocar (330). In the present example, at least the exterior surface of trocar (330) comprises an electrically conductive material.

When anvil (5350) is not attached to trocar (330), an electrical circuit defined by contact surfaces (5380, 5382) and wires (5386) is in an open state as shown in FIG. 27. As shown in FIG. 28, with anvil (5350) properly attached to trocar (330), contact between the exterior surface of shaft (332) of trocar (330) and electrical contact surface (5380); and between surface (338) of trocar (330) and electrical contact surface (5382) completes and closes the electrical circuit defined by contact surfaces (5380, 5382) and wires (5386) so as to actuate transmitter (5384). Actuation of transmitter (5384) causes a signal (5390) to be emitted from transmitter (5384). Signal (5390) is configured to actuate an indicator (not shown) so as to cause the indicator to emit audible, tactile, and/or visible feedback to an operator so as to indicate proper attachment of anvil (5350) to trocar (330). In some instances, the indicator is positioned within handle assembly (110). In some other instances, the indicator is positioned external to instrument (10). In still other instances, the indicator is positioned within anvil (5350). For instance, an LED light on anvil (5350) may serve as the indicator, such that the light illuminates in response to closure of the circuit defined by trocar (330), contact surfaces (5380, 5382), and wires (5386). Other suitable forms that the indicator may take, and other suitable locations for the indicator, will be apparent to those of ordinary skill in the art in view of the teachings herein.

E. Exemplary Snap-Fit Anvil and Trocar

Figure 29:
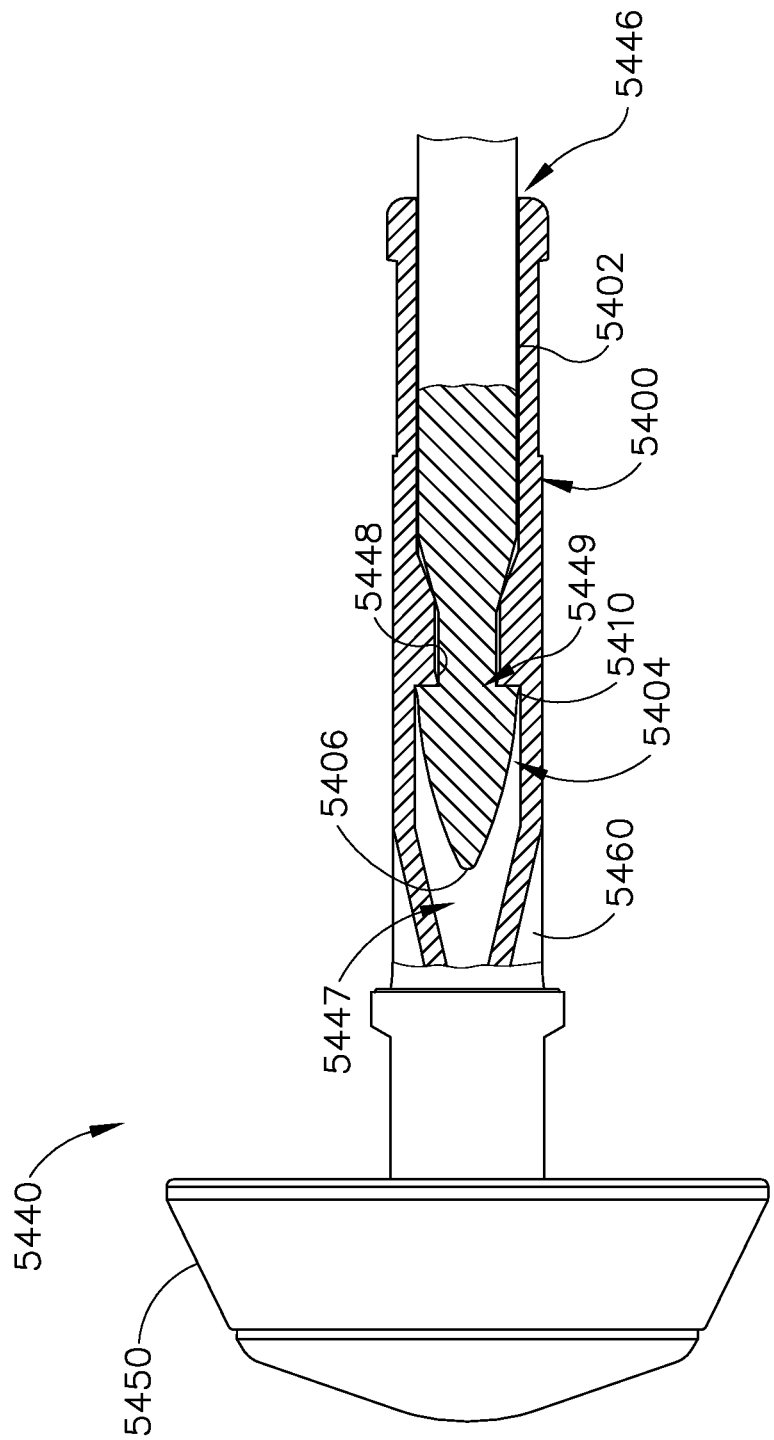
FIG. 29 depicts a cross-sectional side view of the distal end of yet another exemplary alternative circular stapler with an anvil of the circular stapler secured to a trocar of the circular stapler.
Figure 30A:
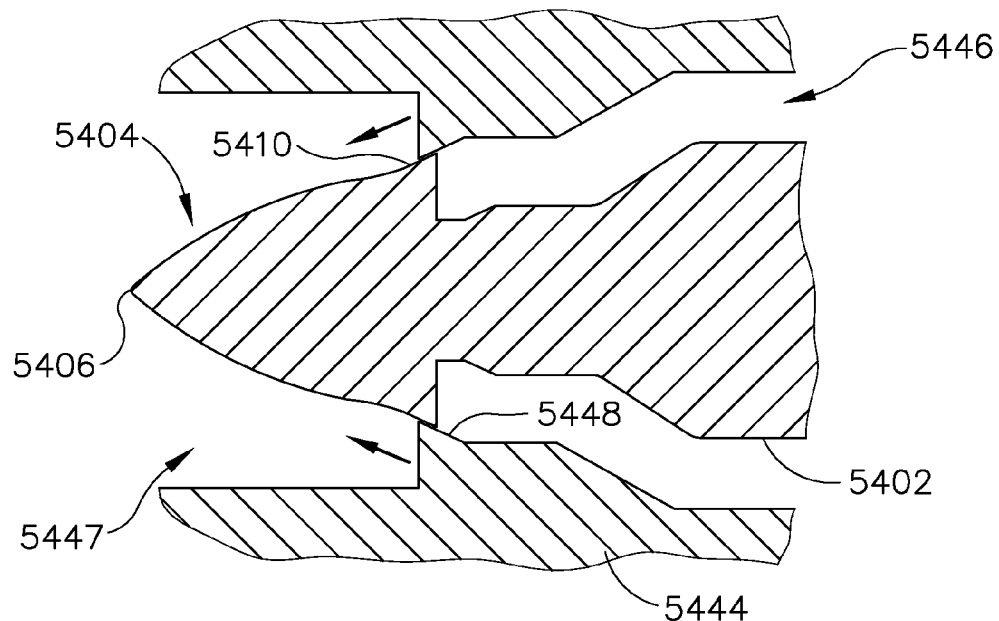
FIG. 30A depicts a cross-sectional side view of the anvil of FIG. 29 positioned about the trocar of FIG. 29 in a first position.
Figure 30B:
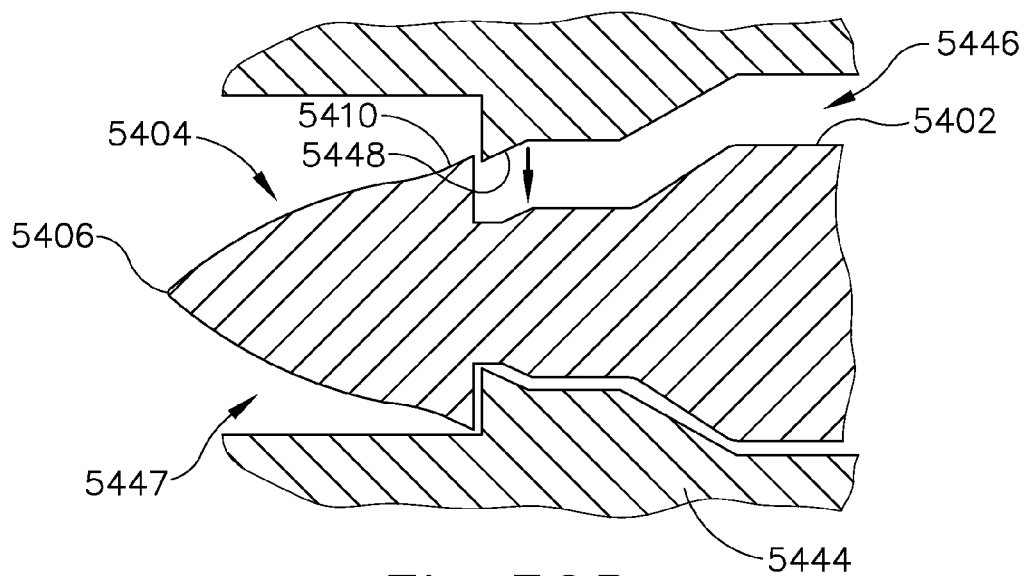
FIG. 30B depicts a cross-sectional side view of the anvil of FIG. 29 positioned about the trocar of FIG. 29 in a second position.

FIGS. 29-30B show an exemplary trocar (5400) and anvil (5440) that are configured to operate substantially similar to trocars (330, 5200) and anvils (400, 5240, 5300, 5350) discussed above respectively except for any differences discussed below. For instance, trocar (5400) is operable to translate distally and proximally relative to tubular casing (310) in response to rotation of knob (130) as discussed above. As will be discussed in more detail below, anvil (5440) is configured to be attached to trocar (5400) such that translation of trocar (5400) relative to tubular casing (310) is communicated directly to anvil (5440) as described above with reference to FIGS. 12A-12C.

Trocar (5400) comprises a shaft (5402) and a head (5404). Head (5404) includes a pointed tip (5406). While tip (5406) is pointed in the present example, tip (5406) is not sharp. Tip (5406) will thus not easily cause trauma to tissue due to inadvertent contact with tissue. Head (5404) is generally conically shaped. A proximal end of head (5404) is flared outwardly so as to present a conical lip (5410) which is raised relative to the remainder of head (5404).

Anvil (5440) of the present example comprises a head (5442) and a shank (5444). Shank (5444) defines a bore (5446). Bore (5446) defines a distal chamber (5447) configured to receive head (5404) of trocar (5400) so as to selectively secure anvil (5440) with trocar (5400). A proximal end of chamber (5447) includes a raised conical lip (5448) which defines a proximal opening (5449). As best seen in FIG. 30A, raised conical lip (5448) of bore (5446) and raised conical lip (5410) of head (5404) present mating angular surfaces. A diameter of raised conical lip (5410) of head (5404) is greater than a diameter of conical lip (5448) of chamber (5447) such that head (5404) must be forced into chamber (5447). In particular, as trocar (5404) is forced distally relative to anvil (5440), the mating angular surfaces presented by raised conical lips (5410, 5448) cause compression and/or deflection of one or both raised conical lips (5410, 5448) such that head (5404) of trocar (5400) may be passed into chamber (5447). Once head (5404) is positioned within chamber (5447), raised conical lips (5410, 5448) return to their original shape such that head (5404) is locked within chamber (5447) as shown in FIG. 30B.

In addition to or in lieu of the foregoing, anvil (5440) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

F. Exemplary Anvil Proximity Sensor

Figure 31:
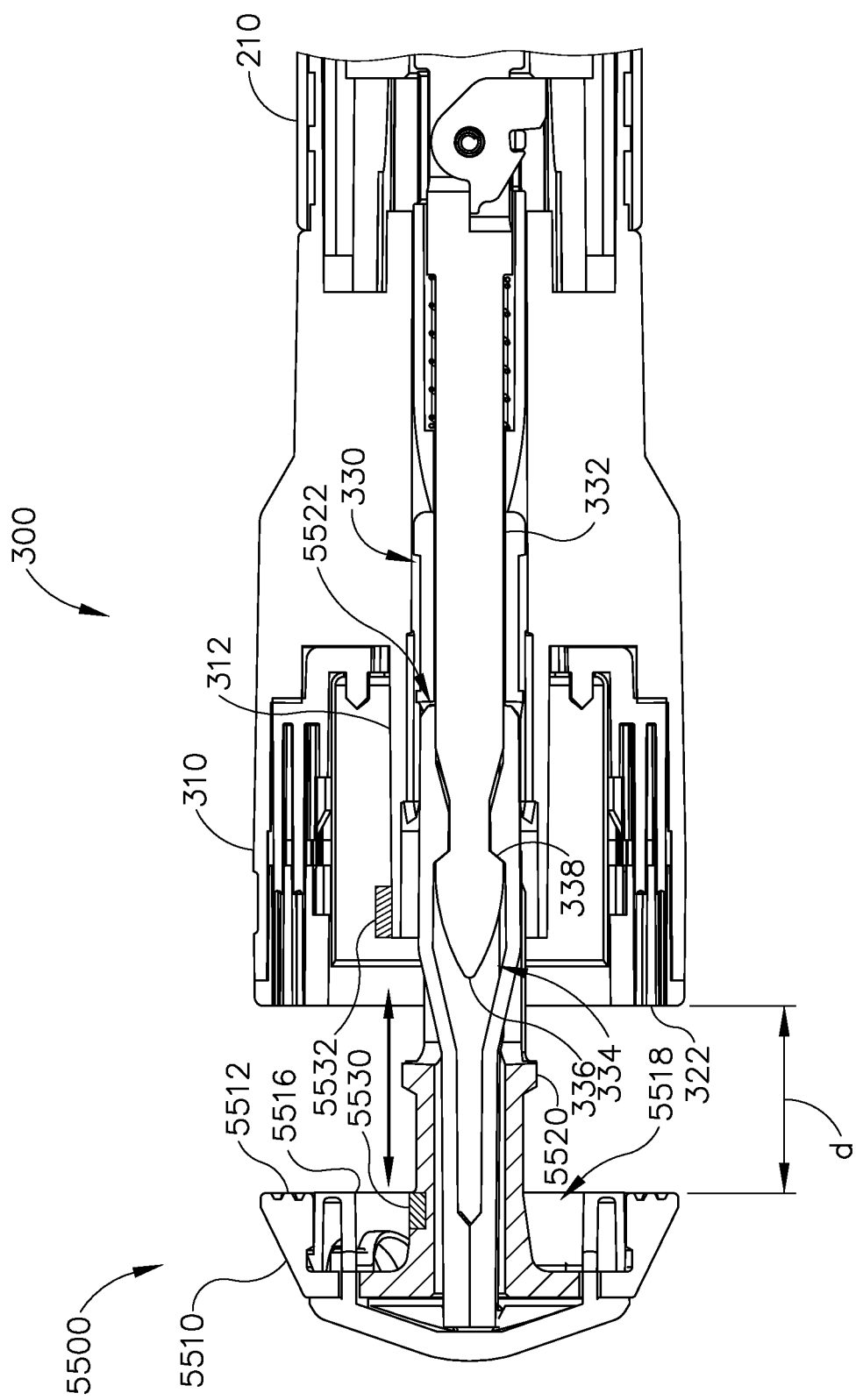
FIG. 31 depicts a cross-sectional side view of the distal end of yet another exemplary alternative circular stapler.

FIG. 31 depicts an exemplary anvil (5500) that is configured to operate substantially similar to anvils (400, 5240, 5300, 5440) discussed above except for any differences discussed below. For instance, anvil (5500) is configured to be attached to trocars (330, 5200, 5400) discussed above such that translation of trocars (330, 5200, 5400) relative to tubular casing (310) is communicated directly to anvil (5500) as described above with reference to FIGS. 12A-12C.

Anvil (5500) of the present example comprises a head (5510) and a shank (5520). Head (5510) includes a proximal surface (5512). Proximal surface (5512) terminates at an inner edge (5516), which defines an outer boundary of an annular recess (5518) surrounding shank (5520). As discussed above, knob (130) may be used to adjust the gap distance (d) between opposing surfaces (5512, 322) of anvil (5500) and stapling head assembly (300). Setting an appropriate gap distance (d) before actuating stapling head assembly (300) may be critical to the success of an anastomosis. For instance, if the gap distance (d) is too great, the staples that are deployed at the anastomosis site may not be sufficiently formed as discussed above. This may result in leakage at the anastomosis site, and in some cases may ultimately lead to the separation of the anatomical lumen sections that are joined at the anastomosis site. If the gap distance (d) is too small, the internal structure of the tissue compressed between surfaces (5512, 322) may be damaged to the point where the structural integrity of the tissue is compromised. This may prevent the tissue from adequately holding the formed staples, which again may result in leakage or other failure of the anastomosis. It may therefore be desirable to provide the operator with some form of feedback indicating whether the gap distance (d) is within an appropriate range. It may also be desirable to prevent the operator from actuating stapling head assembly (300) unless the gap distance (d) is within an appropriate range.

Shank (5520) includes a magnet (5530) that is secured within an exterior surface of shank (5520) such that translation of anvil (5500) causes concurrent translation of magnet (5530). Magnet (5530) of the present example is secured within a portion of shank (5520) located within annular recess (5518) Inner core member (312) of stapling head assembly (300) includes a Hall Effect sensor (5532). Hall Effect sensor (5532) is configured to sense a magnetic field emitted from magnet (5530). In particular, as anvil (5500) translates distally and proximally relative to tubular casing (310) of stapling head assembly (300), an output voltage of Hall Effect sensor (5532) varies in response to translation of magnet (5530) toward and away from Hall Effect sensor (5532).

Hall Effect sensor (5532) is in electrical communication with a control circuit (not shown) that is configured to control firing of stapling head assembly (300). When anvil (5500) is appropriately positioned relative to stapling head assembly (300) (i.e., an appropriate gap distance (d) exists between opposing surfaces (322, 5512)), a predetermined voltage, or range of voltages, is communicated from Hall Effect sensor (5532) to the control unit so as to indicate to the control unit that anvil (5500) is appropriately positioned. In response, the control circuit permits firing of stapling head assembly (300). Otherwise, when anvil (5500) is not appropriately positioned relative to stapling head assembly (300), a predetermined voltage, or range of voltages, is communicated from Hall Effect sensor (5532) to the control circuit so as to indicate to the control unit that anvil (5500) is not appropriately positioned. In response, the control unit prohibits firing of stapling head assembly (300).

In addition to or as an alternative to selectively enabling/disabling firing of stapling head assembly (300) based on signals from Hall Effect sensor (5532), the control circuit and/or some other circuit may be configured to provide some form of audible, tactile, and/or visible feedback to the operator, with the feedback being indicative of whether the gap distance (d) is within an appropriate range. For instance, the feedback may be provided once the gap distance (d) reaches an appropriate range. Alternatively, the feedback may be provided during the entire time that the position of anvil (5500) is being adjusted, with the feedback changing based on whether the gap distance (d) is within an appropriate range. The feedback may be provided in any of the various forms described herein. Other suitable ways in which feedback may be provided based on the gap distance (d) will be apparent to those of ordinary skill in the art in view of the teachings herein.

G. Exemplary Force Limiting Knob

Figure 32A:
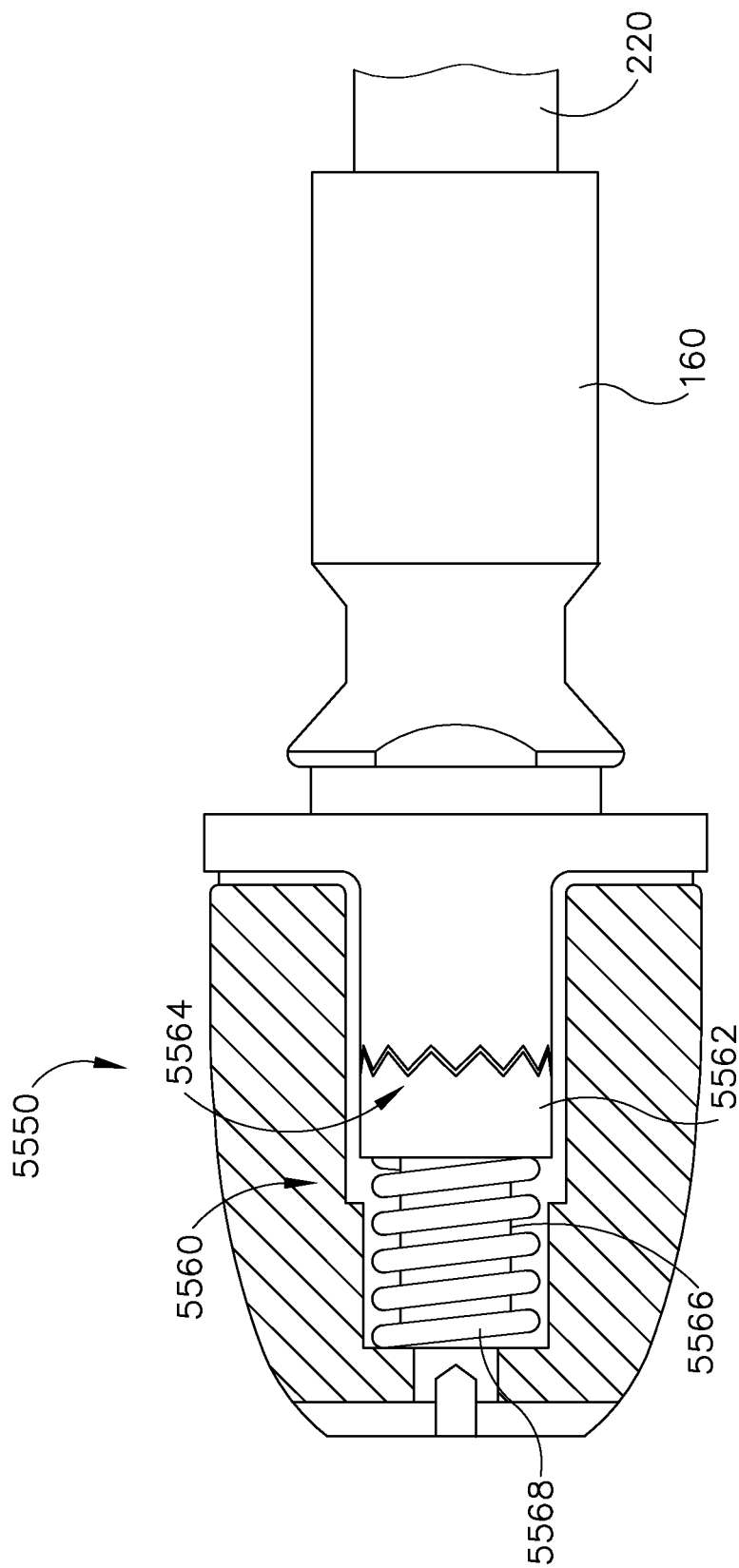
FIG. 32A depicts a cross-sectional side view of an adjustment knob of yet another alternative circular stapler, with a clutch of the adjustment knob engaged with a rod of the adjustment member.
Figure 32B:
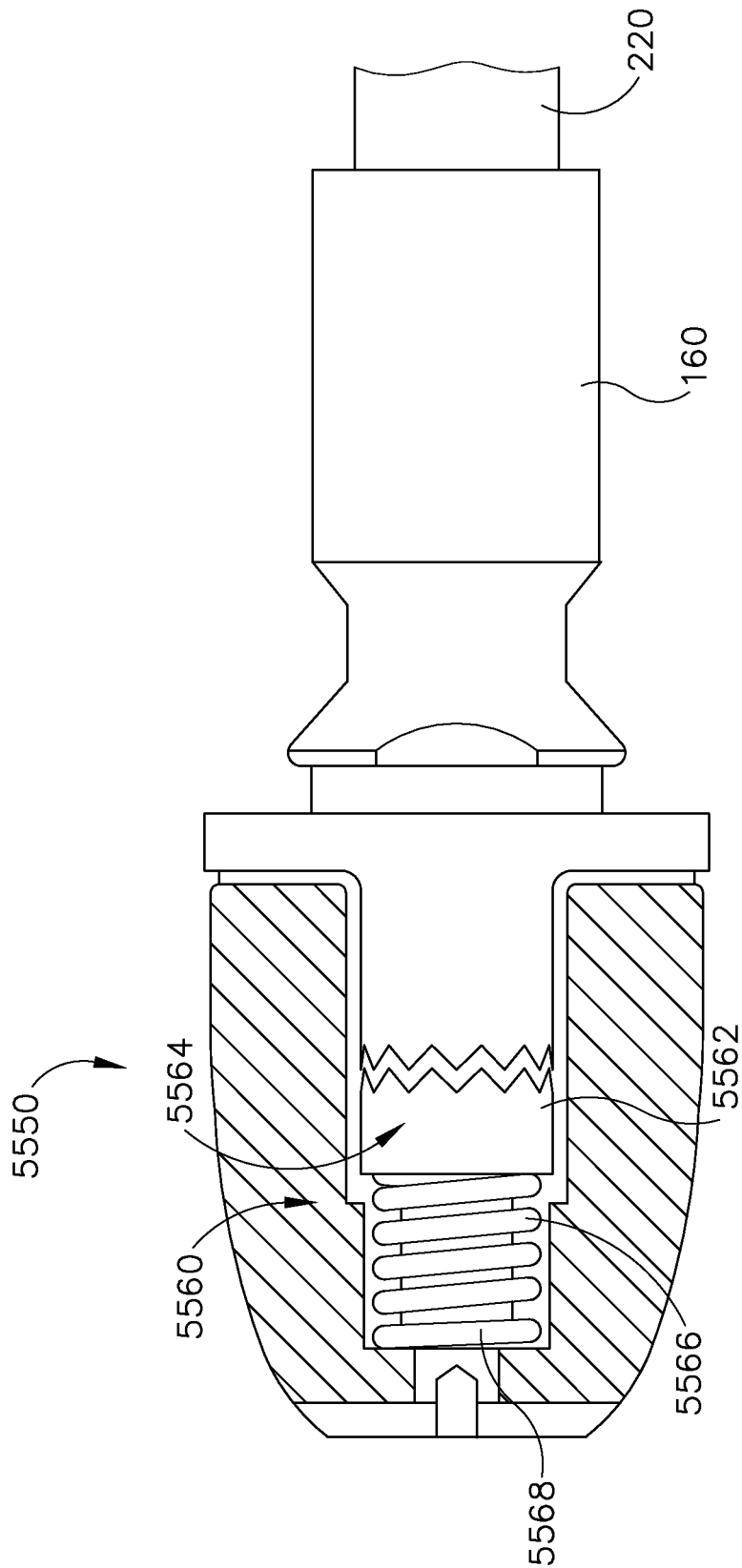
FIG. 32B depicts a cross-sectional side view of the adjustment knob of FIG. 32A, with the clutch of FIG. 32A disengaged with the rod of FIG. 32A.
Figure 33:
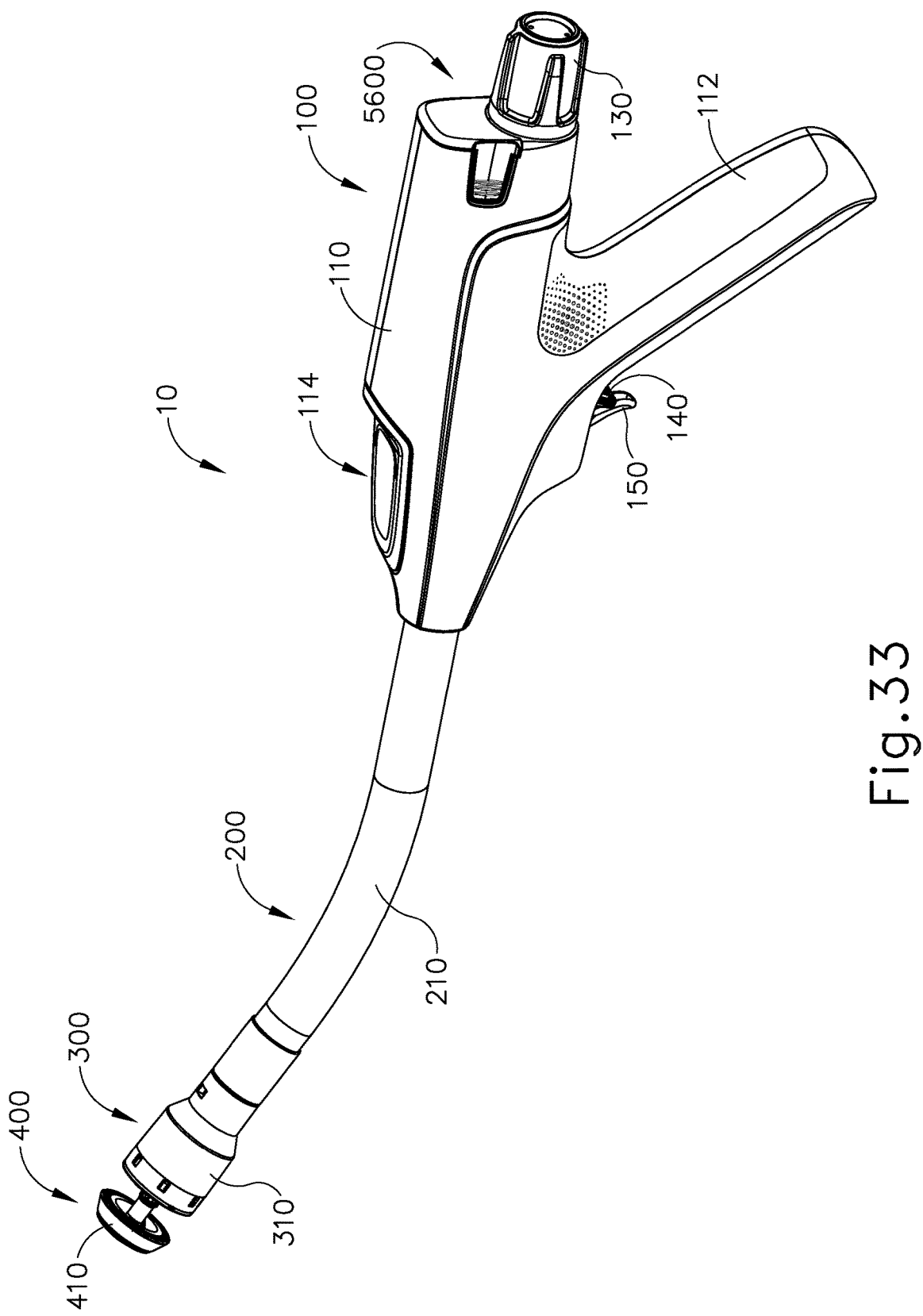
FIG. 33 depicts a perspective view of yet another exemplary alternative circular stapler.
Figure 34:
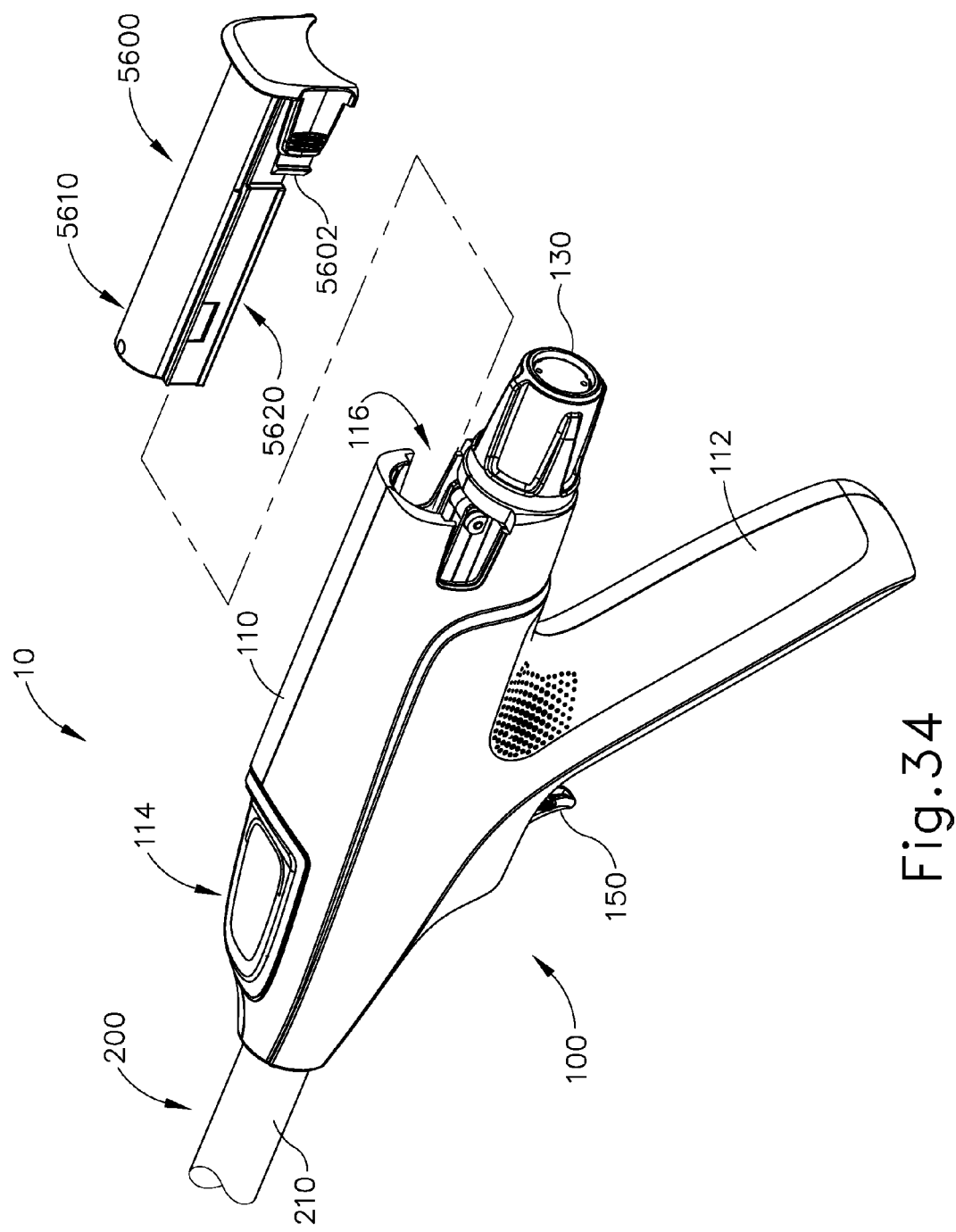
FIG. 34 depicts a perspective view of the circular stapler of FIG. 33, with a battery pack removed from a handle assembly of the circular stapler.

FIGS. 32A and 32B depict an exemplary knob (5550) that is configured to operate substantially similar to knob (130) discussed above except for any difference discussed below. For instance, knob (5550) may be positioned at a proximal end of handle assembly (100) in place of knob (130), and may be rotated relative to casing (110) to provide precise clamping of the tissue between anvil (400) and the stapling head assembly (300) as discussed above with reference to knob (130) of instrument (10).

As discussed above with reference to knob (130), knob (5550) may be used to adjust the gap distance (d) between opposing surfaces (312, 322) of anvil (400) and stapling head assembly (300). Limiting a compressive force applied to the tissue compressed between surfaces (312, 322) may be critical to the success of an anastomosis. For instance, if the compressive force is too great, the internal structure of the tissue compressed between surfaces (312, 322) may be damaged to the point where the structural integrity of the tissue is compromised. This may prevent the tissue from adequately holding the formed staples, which again may result in leakage or other failure of the anastomosis.

Knob (5550) protrudes proximally from casing (110) of handle assembly (100) and is rotatable relative to casing (110). As discussed above with reference to knob (130), knob (5550) is configured to cooperate with nut (160) and trocar actuation rod (220) to thereby translate trocar actuation rod (220) longitudinally relative to casing (110) in response to rotation of nut (160) and knob (5550) relative to casing (110). Also as discussed above, trocar (330) will translate longitudinally relative to outer sheath (210) in response to translation of trocar actuation rod (220) relative to outer sheath (210) and casing (110).

Unlike knob (130) described above, knob (5550) of this example is coupled with nut (160) via a clutch assembly (5560). Clutch assembly (5560) includes a gear (5562). Gear (5562) is slidably disposed about a shaft (5566), which is positioned within an interior of knob (5550) such that gear (5562) is operable to translate along the length of shaft (5566). Gear (5562) is, however, secured to shaft (5566) (e.g., via slot-and-key) such that gear (5562) is unable to rotate about shaft (5566) and such that rotation of knob (5550) is causes rotation of gear (5562). As shown in FIG. 32A, gear (5562) is resiliently biased via a spring (5568) to engage teeth (5564) formed in a proximal end of nut (160) such that rotation of gear (5562) is configured to cause concurrent rotation of nut (160).

As discussed above, knob (5550) may be used to adjust the gap distance (d) between opposing surfaces (312, 322) of anvil (400) and stapling head assembly (300). As knob (5550) is rotated to adjust the gap distance (d) so as to compress tissue between surfaces (312, 322), a compressive force applied to the tissue increases. As this compressive force increases, the torque required to rotate knob (5550) increases. As shown in FIG. 32B, once this torque reaches a predetermined level, gear (5562) will disengage teeth (5564) of nut (160) by overcoming the bias of spring (5568). When gear (5562) disengages teeth (5564), further rotation of gear (5562) will cause gear (5562) to slip relative to nut (160) such that further rotation of knob (5550) is not communicated to nut (160). The slipping of gear (5562) relative to nut (160) in response to the torque exceeding a certain level will prevent further compression of the tissue between surfaces (312, 322). In other words, the torque threshold provided by slipping of gear (5562) will restrict the amount of compression that may be achieved between surfaces (312, 322).

H. Exemplary Self-Draining Battery Pack

FIGS. 33-49 depict instrument (10) including an exemplary battery pack (5600) that is configured to operate substantially similar to battery pack (120) discussed above except for any difference discussed below. For instance, battery pack (5600) is operable to provide electrical power to a motor (160) in pistol grip (112) as discussed above with reference to battery pack (120). Battery pack (5600) is removable from handle assembly (100). In particular, as shown in FIGS. 33-34 and 37A-37B, battery pack (5600) may be inserted into socket (116) defined by casing (110). Once battery pack (5600) is fully inserted in socket (116), latches (5602) of battery pack (5600) may resiliently engage interior features of casing (110) to provide a snap fit. To remove battery pack (5600), the operator may press latches (5602) inwardly to disengage latches (5602) from the interior features of casing (110) then pull battery pack (5600) proximally from socket (116). It should be understood that battery pack (5600) and handle assembly (100) may have complementary electrical contacts, pins and sockets, and/or other features that provide paths for electrical communication from battery pack (5600) to electrically powered components in handle assembly (100) when battery pack (5600) is inserted in socket (116).

Figure 35:
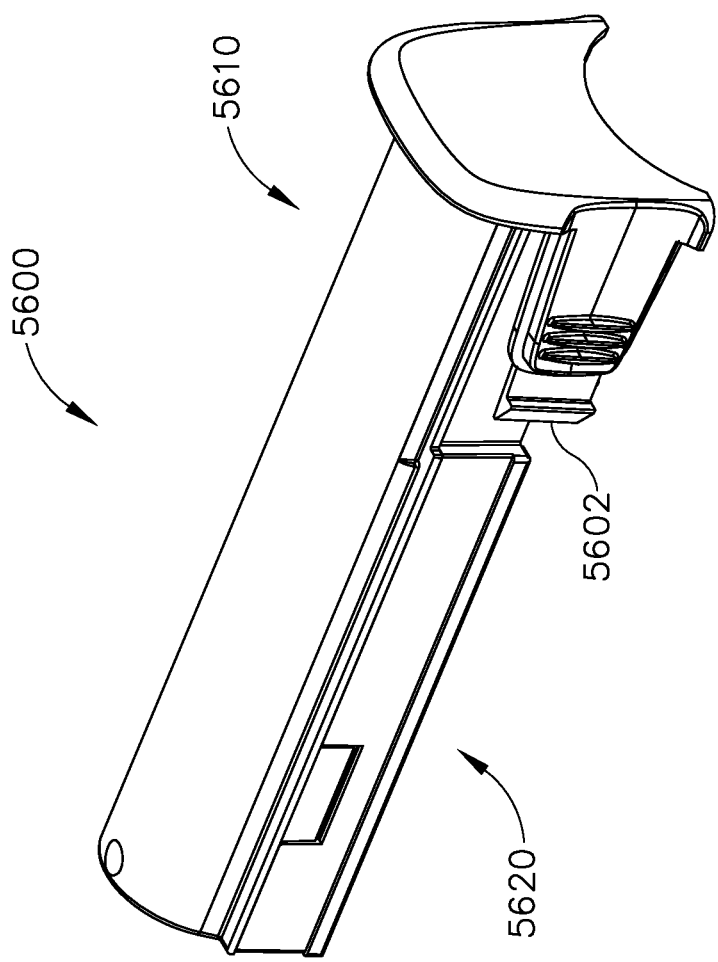
FIG. 35 depicts a perspective view of the battery pack of FIG. 34.
Figure 37A:
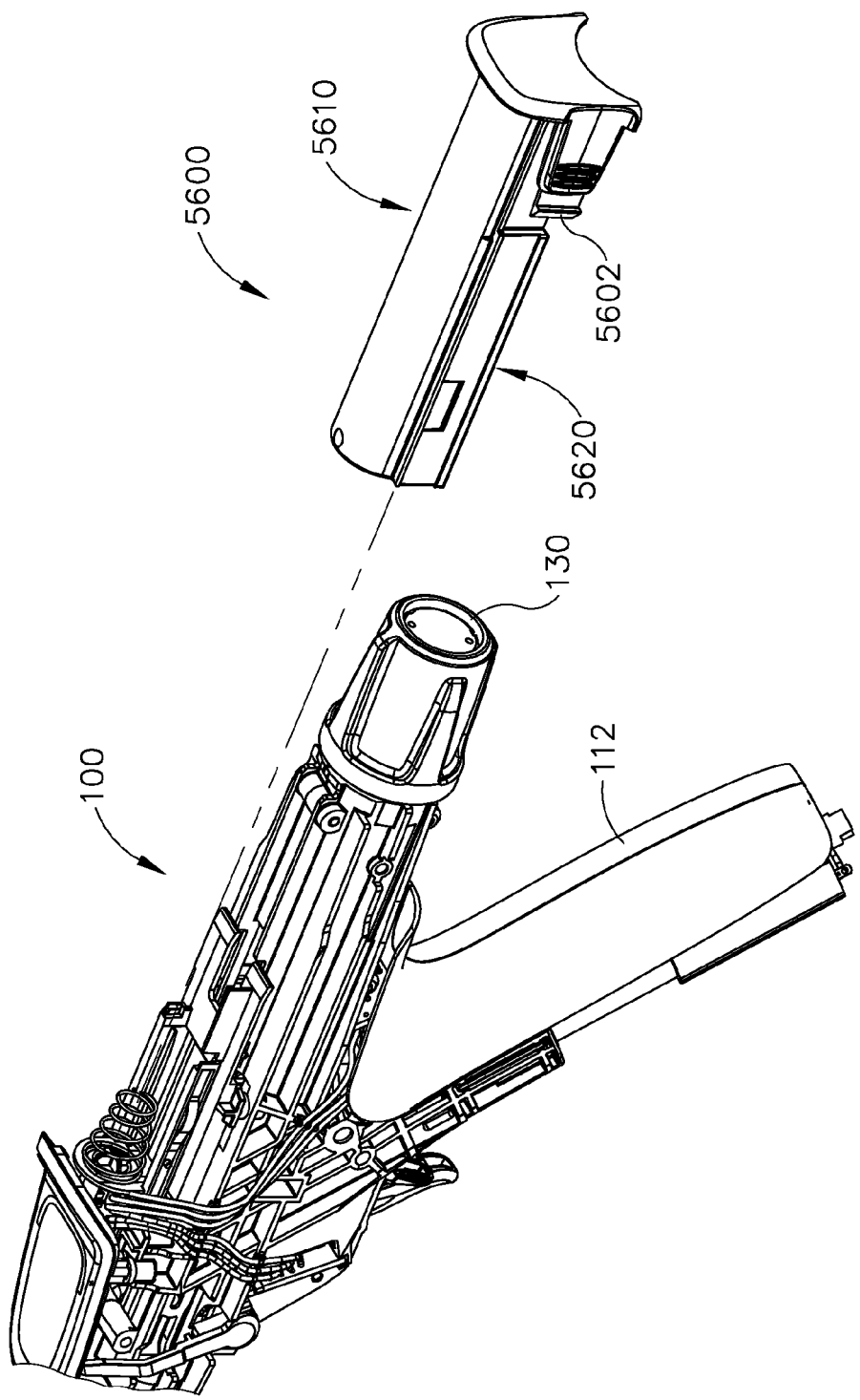
FIG. 37A depicts a perspective view of the handle assembly of FIG. 34, with a casing removed from the handle assembly, and with the battery pack of FIG. 34 spaced apart from the handle assembly.
Figure 37B:
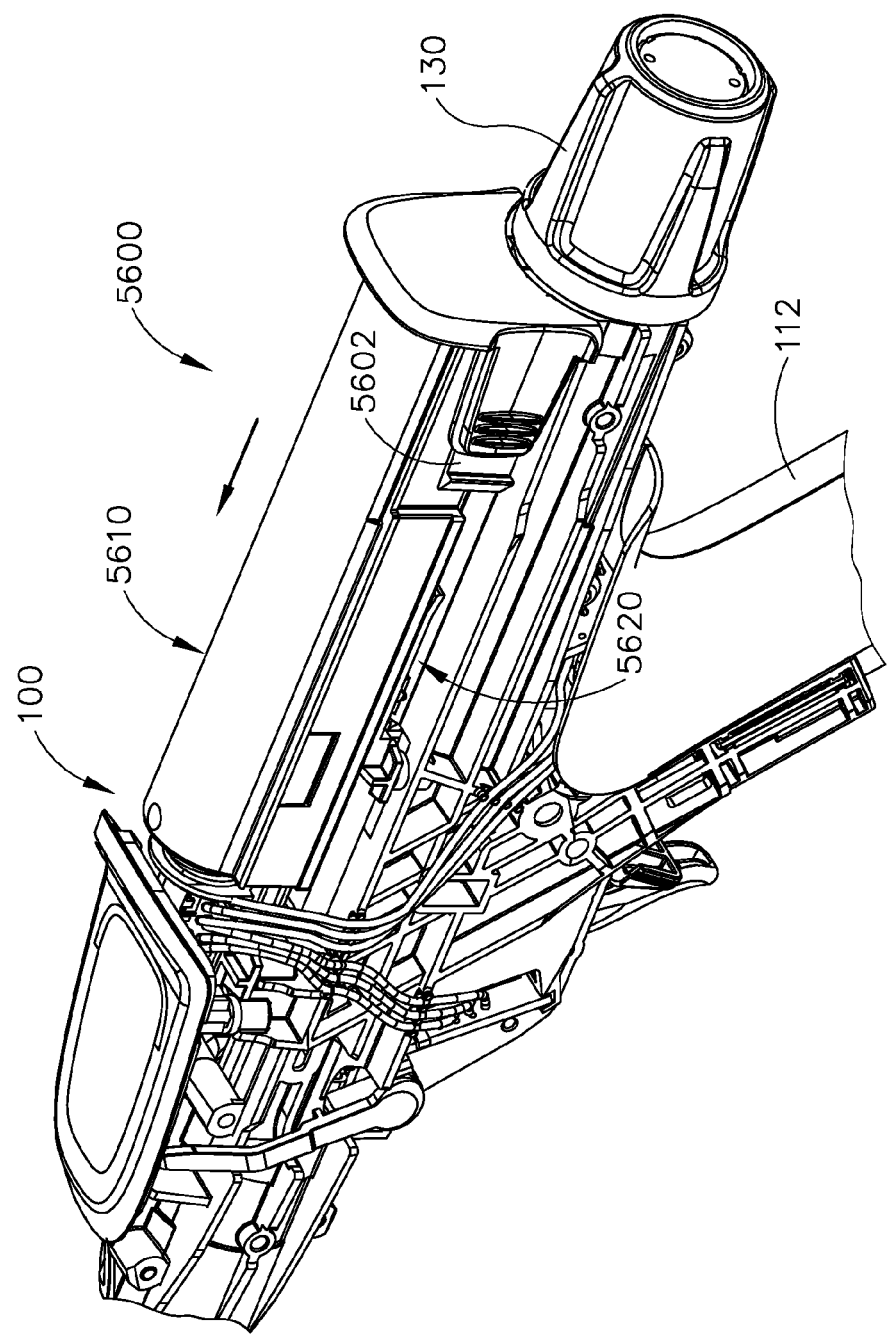
FIG. 37B depicts a perspective view of the handle assembly of FIG. 34, with a casing removed from the handle assembly, and with the battery pack of FIG. 34 coupled with the handle assembly.

As best seen in FIGS. 35 and 36, battery pack (5600) includes an upper housing (5610) and a lower housing (5620). Upper housing (5610) and lower housing (5620) are configured to be secured to one another in a snap-fit manner so as to provide a rigid casing that encloses a plurality of batteries (5630). Lower housing (5620) includes a positive battery contact (5622) configured to connect with a positive terminal of batteries (5630) and a negative battery contact (5624) configured to connect with a negative terminal of batteries (5630). Lower housing (5620) further includes a drain contact (5626). A proximal end of positive battery contact (5622) is biased toward drain contact (5626). As will be discussed in more detail below, contact between positive battery contact (5622) and drain contact (5626) is configured to drain batteries (5630) of power. It should be understood that housing (110) of instrument (10) and upper housing (5610) and batteries (5630) of battery pack (5630) have been omitted from FIGS. 38-49 to assist in understanding operation of battery pack (5600).

Figure 38:
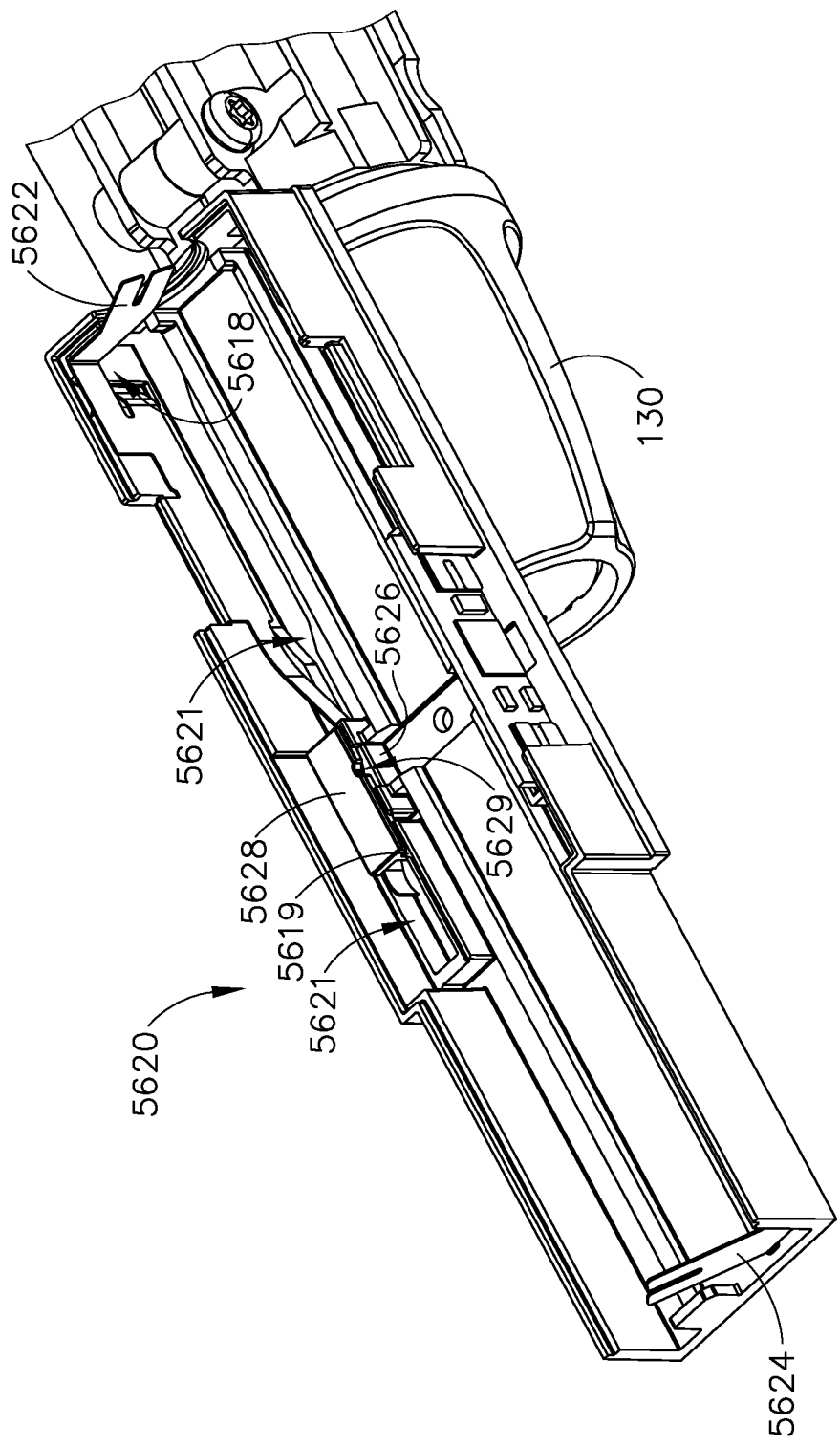
FIG. 38 depicts a perspective view of the handle assembly of FIG. 34, with a casing removed from the handle assembly, and with a lower housing of the battery pack of FIG. 34 in a first position relative to the handle assembly.
Figure 39:
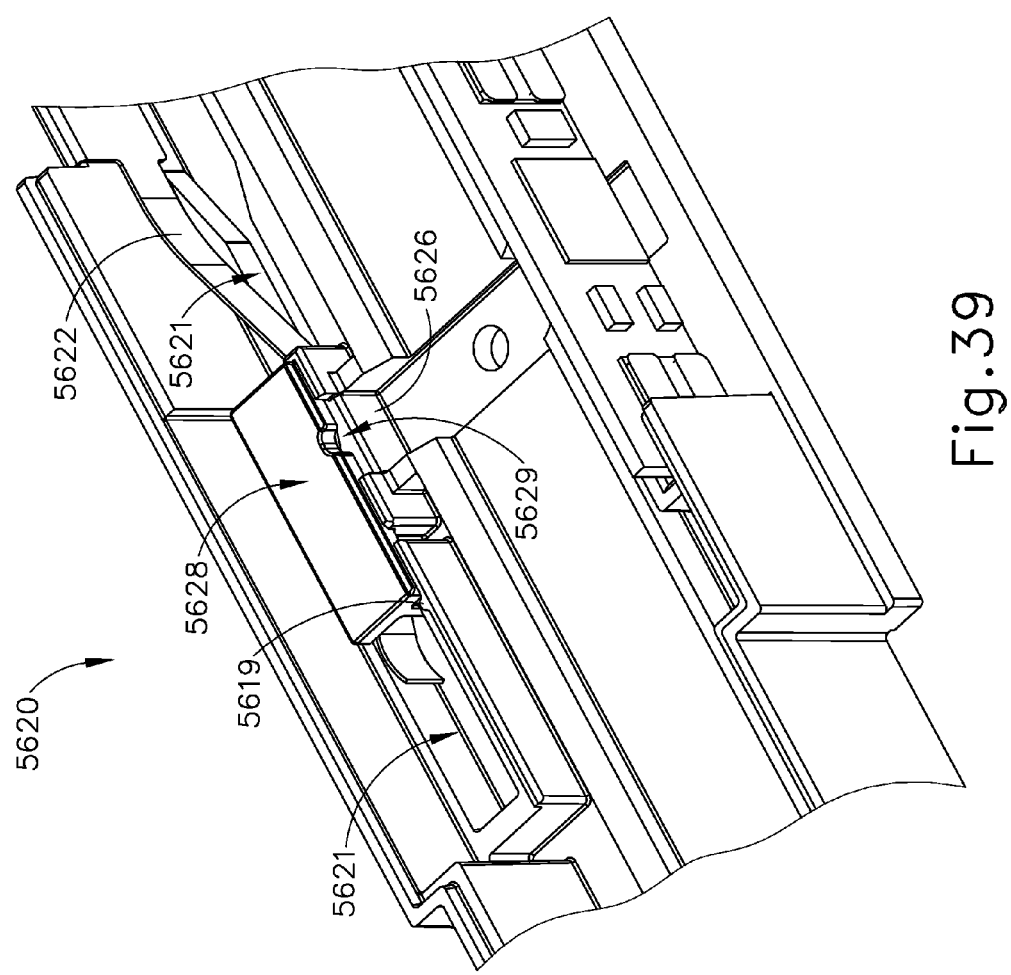
FIG. 39 depicts a detailed perspective view of the lower housing of FIG. 38 in the first position of FIG. 38, with a lockout sled of the lower housing in a first position relative to a body of the lower housing.
Figure 40:
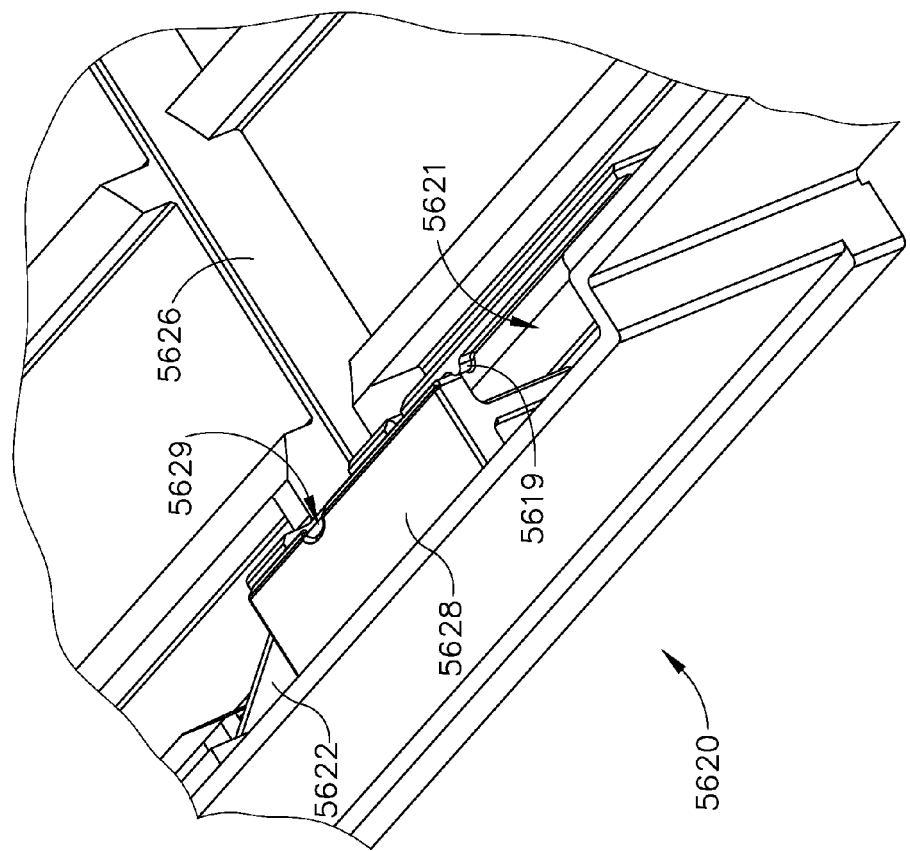
FIG. 40 depicts another detailed perspective view of the lower housing of FIG. 38, with the lockout sled of FIG. 39 in the first position of FIG. 39.

Lower housing (5620) includes a lockout sled (5628) that is slidably disposed within a channel (5621) formed within lower housing (5620) such that lockout sled (5628) is configured to translate longitudinally within channel (5621) relative to lower housing (5620). As shown in FIGS. 38-40, in an initial position, lockout sled (5628) positioned within channel (5621) between drain contact (5626) and the proximal end of positive battery contact (5622) so as to prevent contact between drain contact (5626) and positive battery contact (5622).

Figure 41:
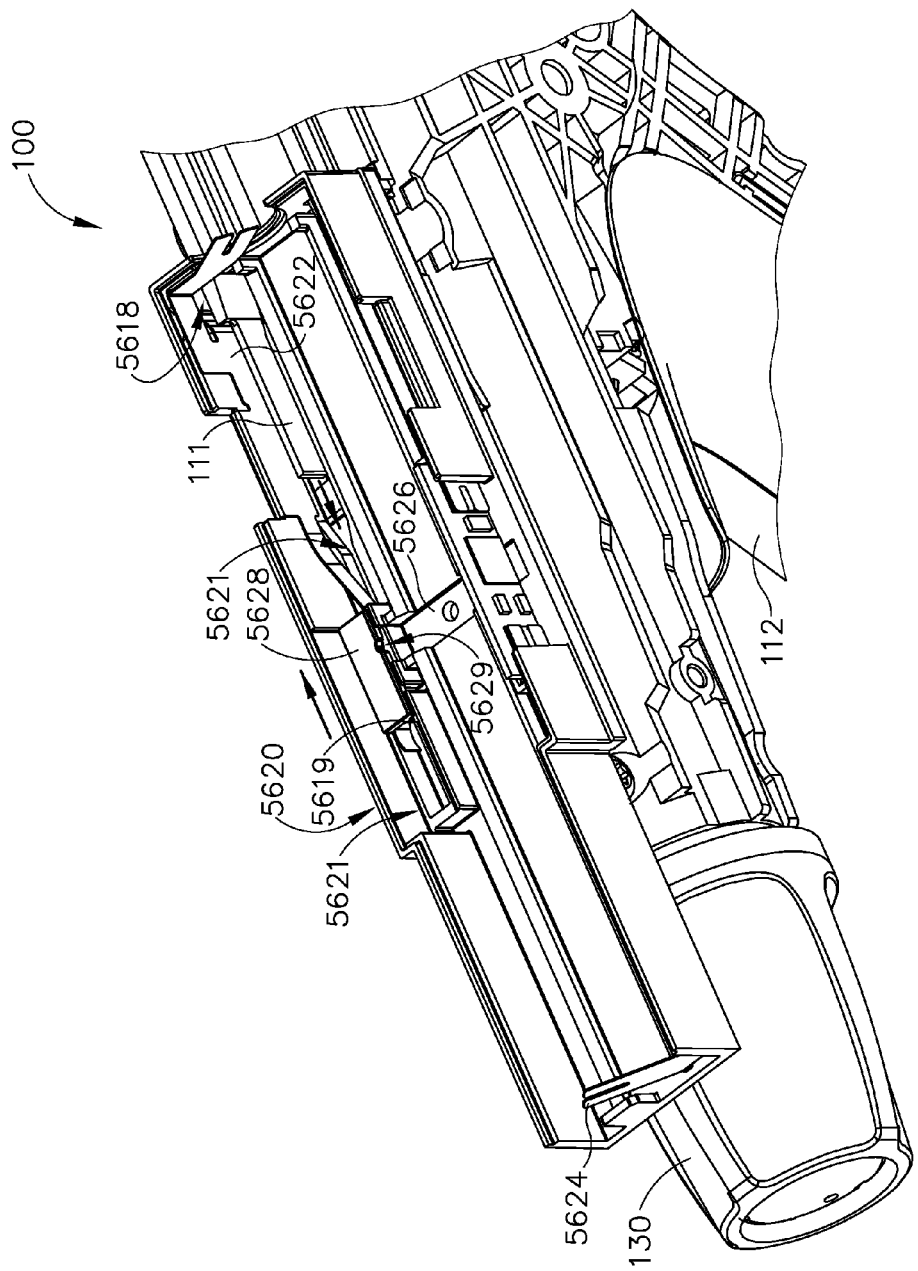
FIG. 41 depicts a perspective view of the handle assembly of FIG. 34, with a casing removed from the handle assembly, and with the lower housing of FIG. 38 moved distally to a second position relative to the handle assembly, and with a lockout flange of the handle assembly received within the lower housing in a first position.
Figure 42:
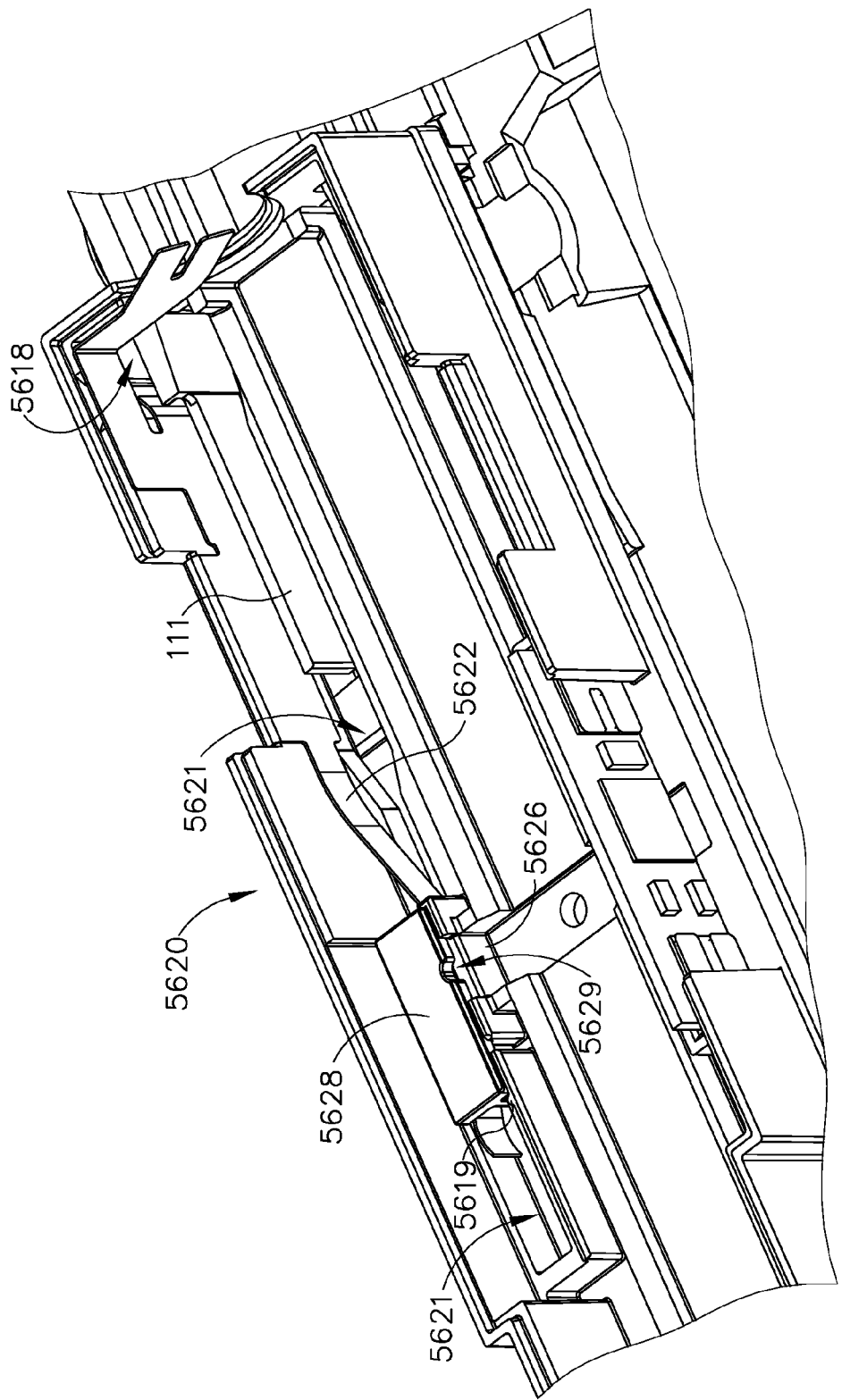
FIG. 42 depicts a detailed perspective view of the lower housing of FIG. 38 in the second position of FIG. 41, with the lockout sled of FIG. 39 remaining in the first position of FIG. 39, and with the lockout flange of FIG. 41 received within the lower housing in the first position of FIG. 41.

As shown in FIGS. 41-42, as battery pack (5600) is inserted into socket (116) of housing (110), a flange (111) of housing (110) passes through an opening (5618) formed in a distal end of lower housing (5620) toward channel (5621) of lower housing (5620).

Figure 43:
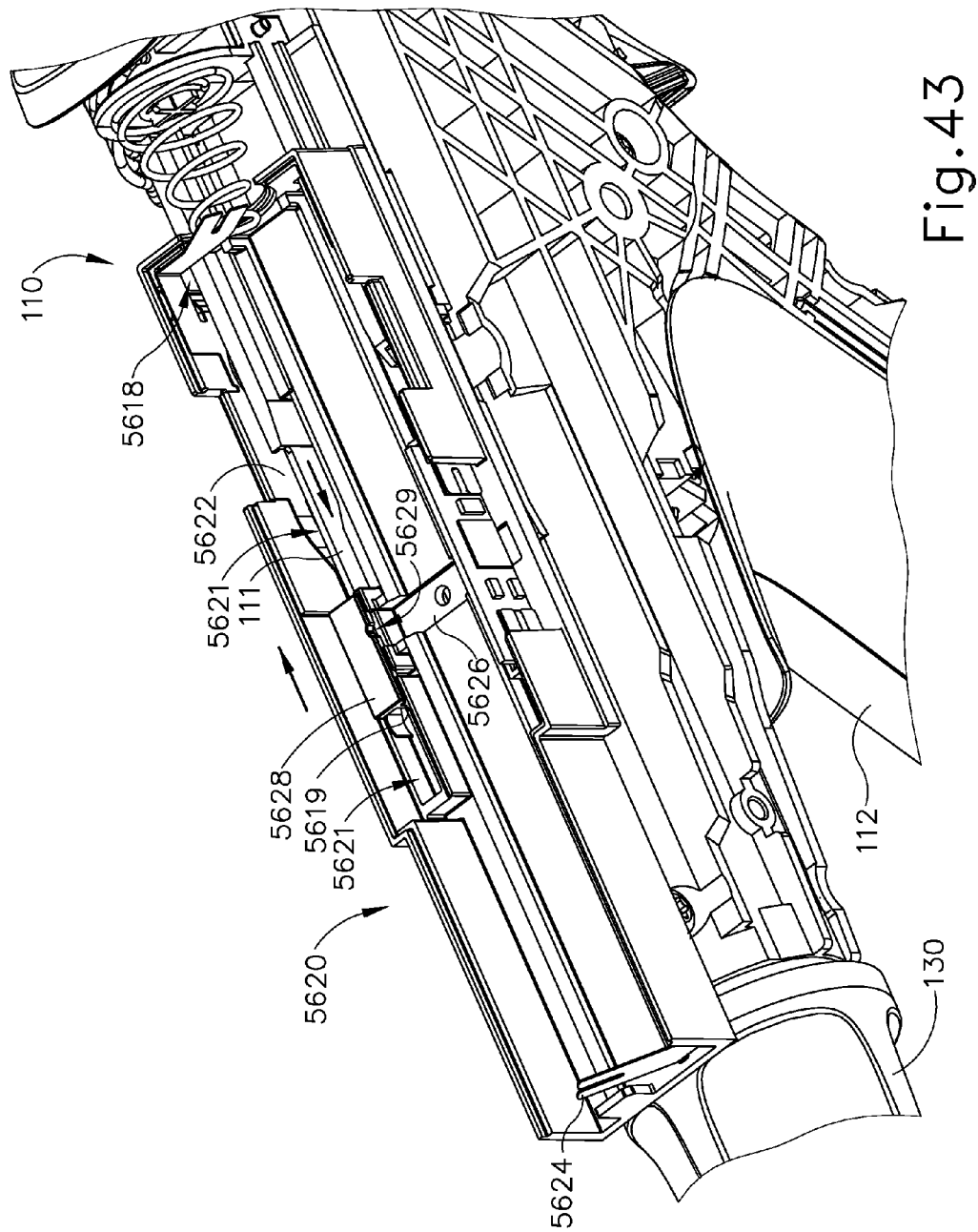
FIG. 43 depicts a perspective view of the handle assembly of FIG. 34, with a casing removed from the handle assembly, with the lower housing of FIG. 38 moved distally to a third position relative to the handle assembly such that the lockout flange of FIG. 42 is moved to a second position such that the lockout flange engages the lockout sled of FIG. 39.
Figure 44:
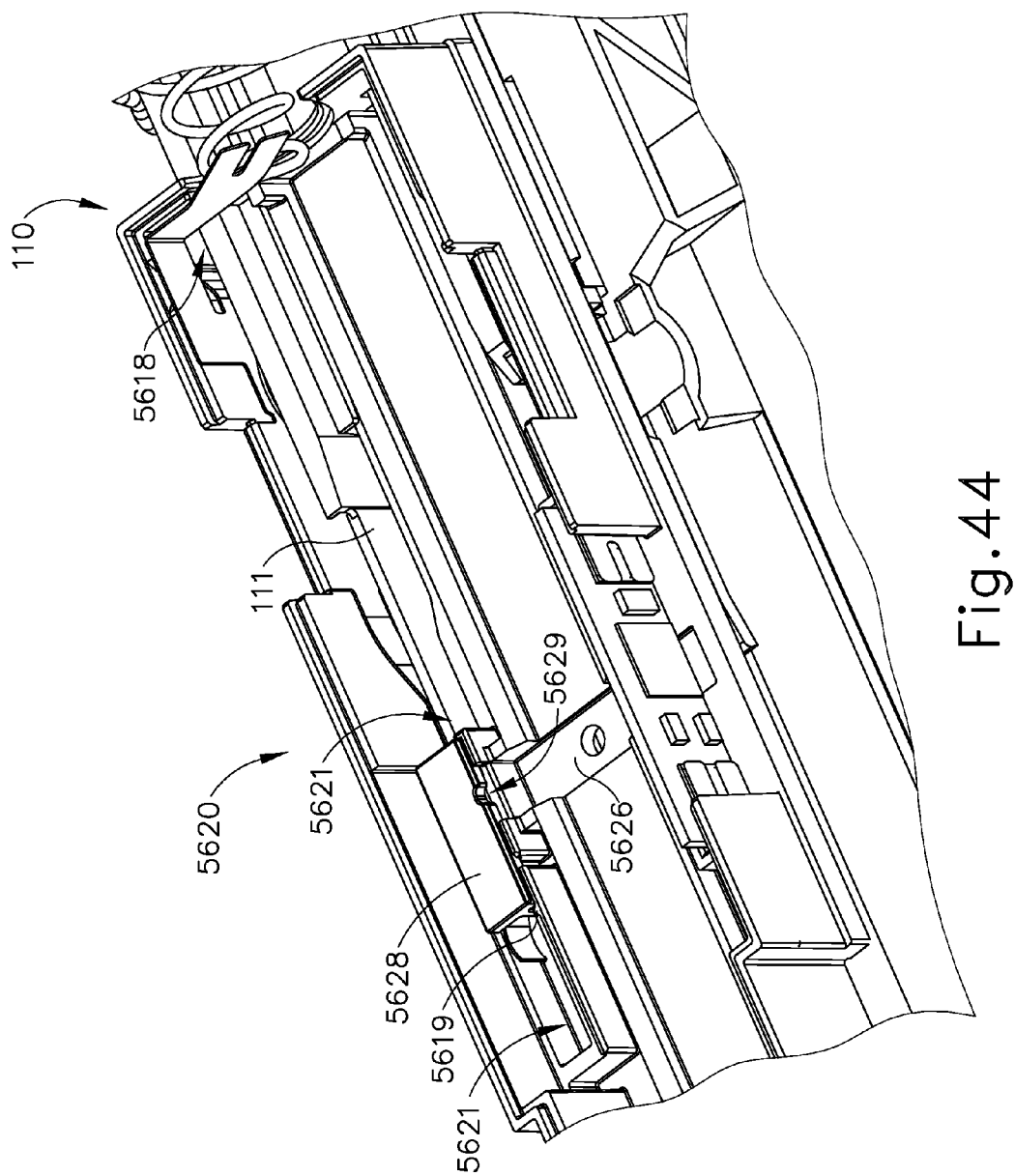
FIG. 44 depicts a detailed perspective view of the lower housing of FIG. 38 in the third position of FIG. 43, with the lockout sled of FIG. 39 remaining in the first position of FIG. 39, and with the lockout flange of FIG. 41 received within the lower housing in the second position of FIG. 43 such that the lockout flange engages the lockout sled.

As shown in FIGS. 43-44, as battery pack (5600) is further inserted into socket (116) of housing (110), flange (111) passes further through opening (5618) and into channel (5621) such that a proximal end of flange (111) comes into contact with a distal end of lockout sled (5628).

Figure 45:
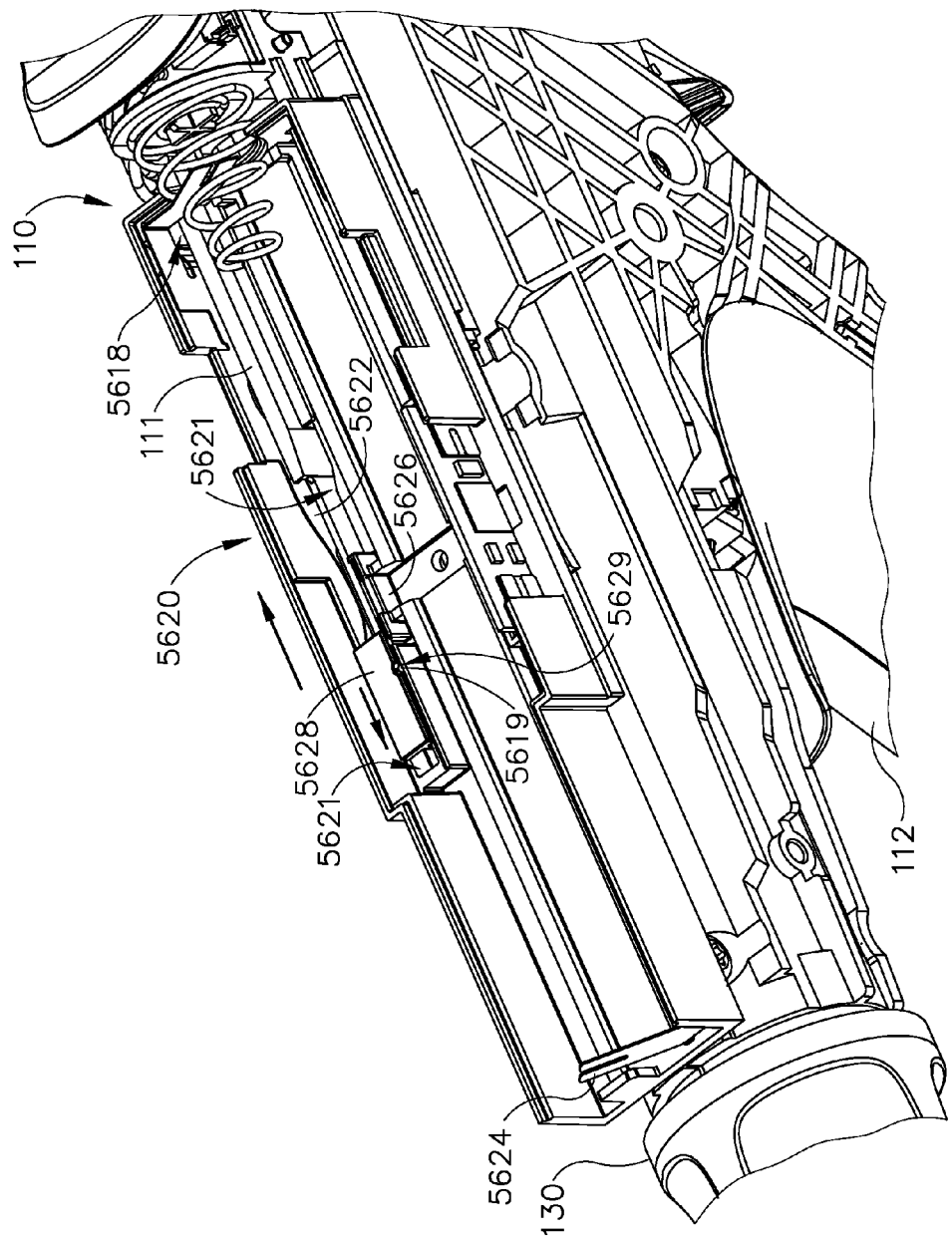
FIG. 45 depicts a perspective view of the handle assembly of FIG. 34, with a casing removed from the handle assembly, with the lower housing of FIG. 38 moved distally to a fourth position relative to the handle assembly such that the lockout flange of FIG. 42 is moved to a third position such that the lockout flange drives the lockout sled of FIG. 39 proximally to a second position.
Figure 46:
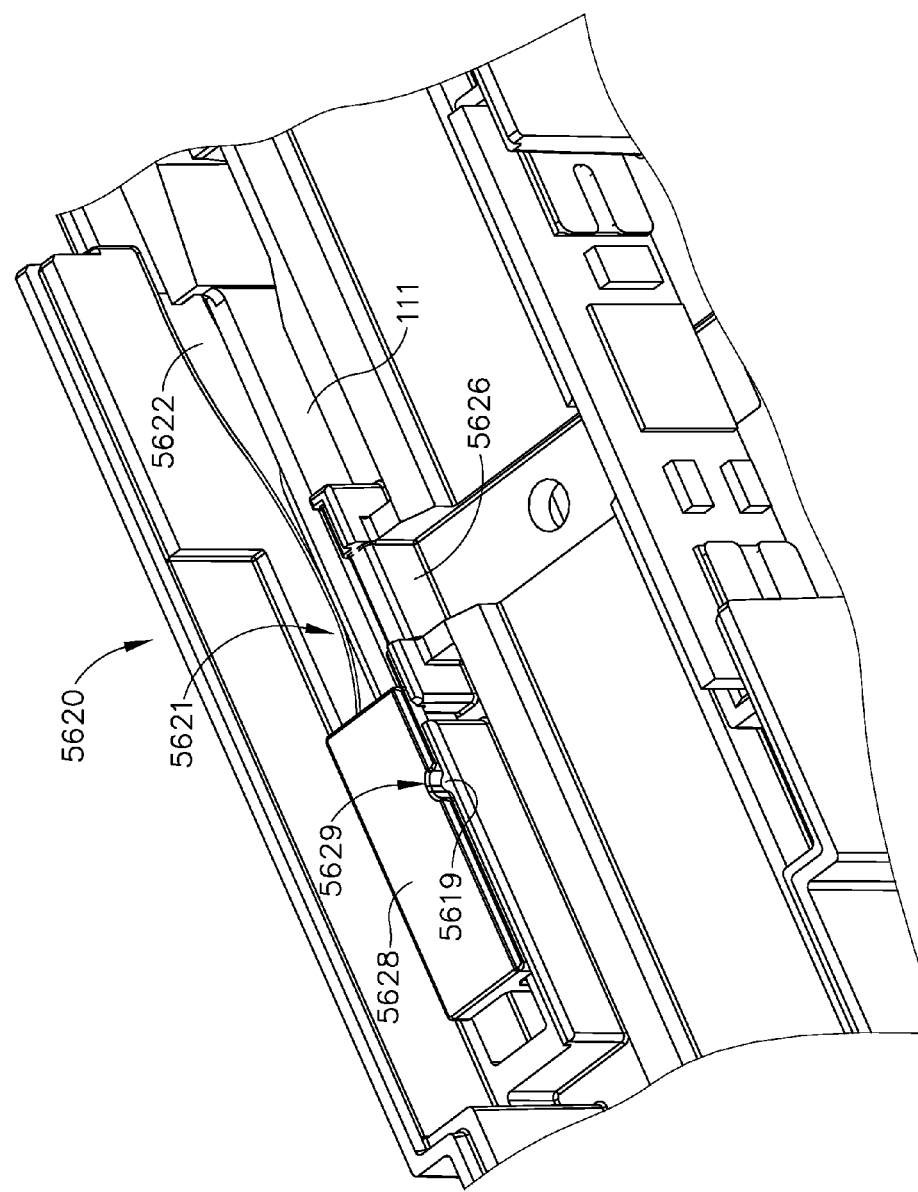
FIG. 46 depicts a detailed perspective view of the lower housing of FIG. 38 in the fourth position of FIG. 45, with the lockout flange of FIG. 41 received within the lower housing in the third position of FIG. 45 such that the lockout flange drives the lockout sled of FIG. 39 moved into the second position of FIG. 45.

As shown in FIGS. 45-46, as battery pack (5600) is further inserted into socket (116) of housing (110) to a point where battery pack (5600) is fully seated within socket (116), flange (111) passes further through opening (5618) and into channel (5621) such that flange (111) drives lockout sled (5628) proximally within channel (5621). In this position, lockout sled (5628) is no longer between positive battery contact (5622) and drain contact (5626). However, flange (111) is now positioned between positive battery contact (5622) and drain contact (5626). Thus, it should be understood that as battery pack (5600) is passed into socket (116), lockout sled (5628) and flange (111) cooperate to prevent contact between positive battery contact (5622) and drain contact (5626).

Figure 47:
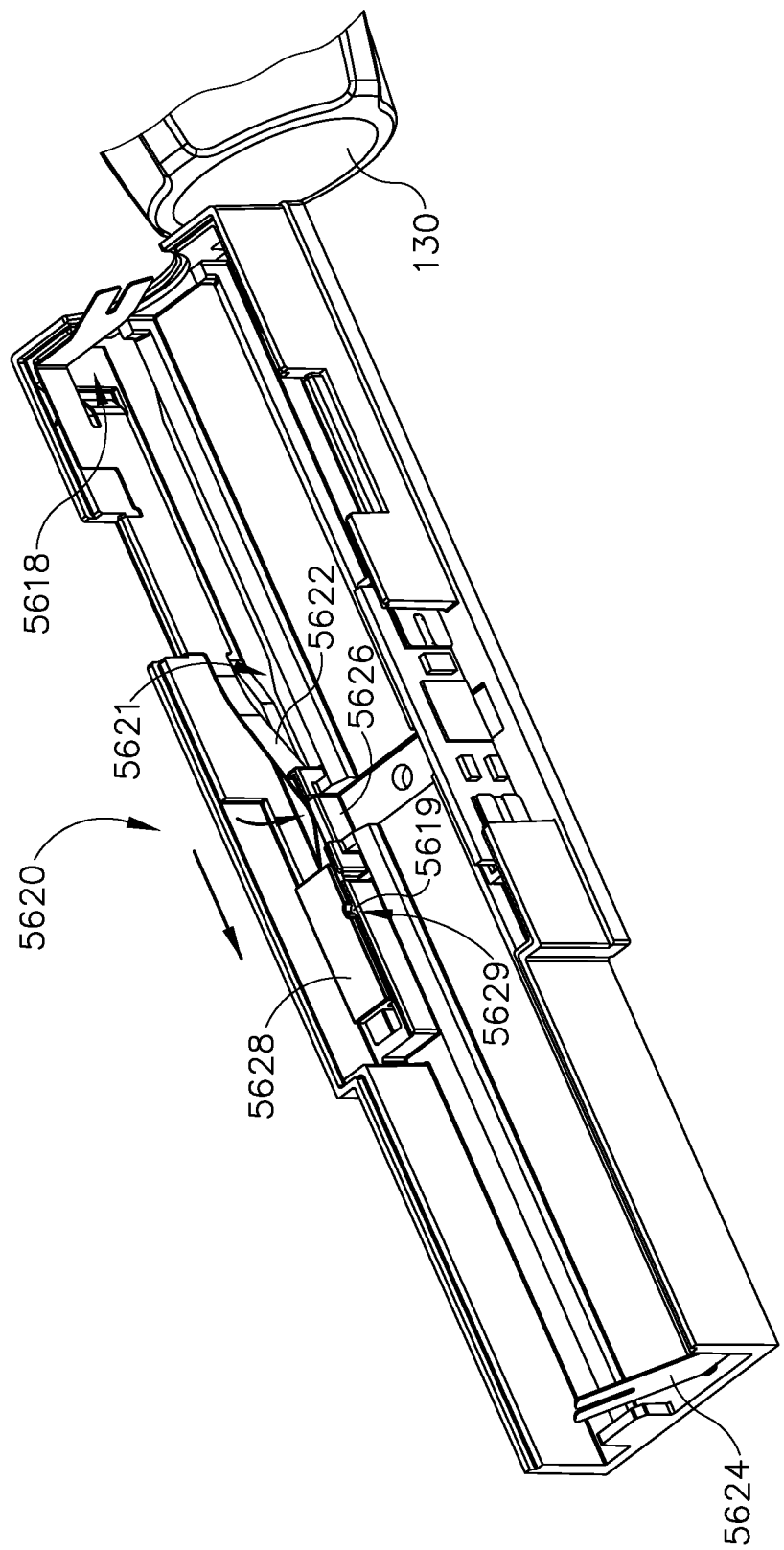
FIG. 47 depicts a perspective view of the handle assembly of FIG. 34, with a casing removed from the handle assembly, with the lower housing of FIG. 38 removed from the handle assembly such that the lockout flange of FIG. 42 is removed from the lower housing, and with the lockout sled of FIG. 39 remaining in the second position of FIG. 45 such that a drain contact of the battery pack of FIG. 34 is biased toward a positive contact of the battery pack.
Figure 48:
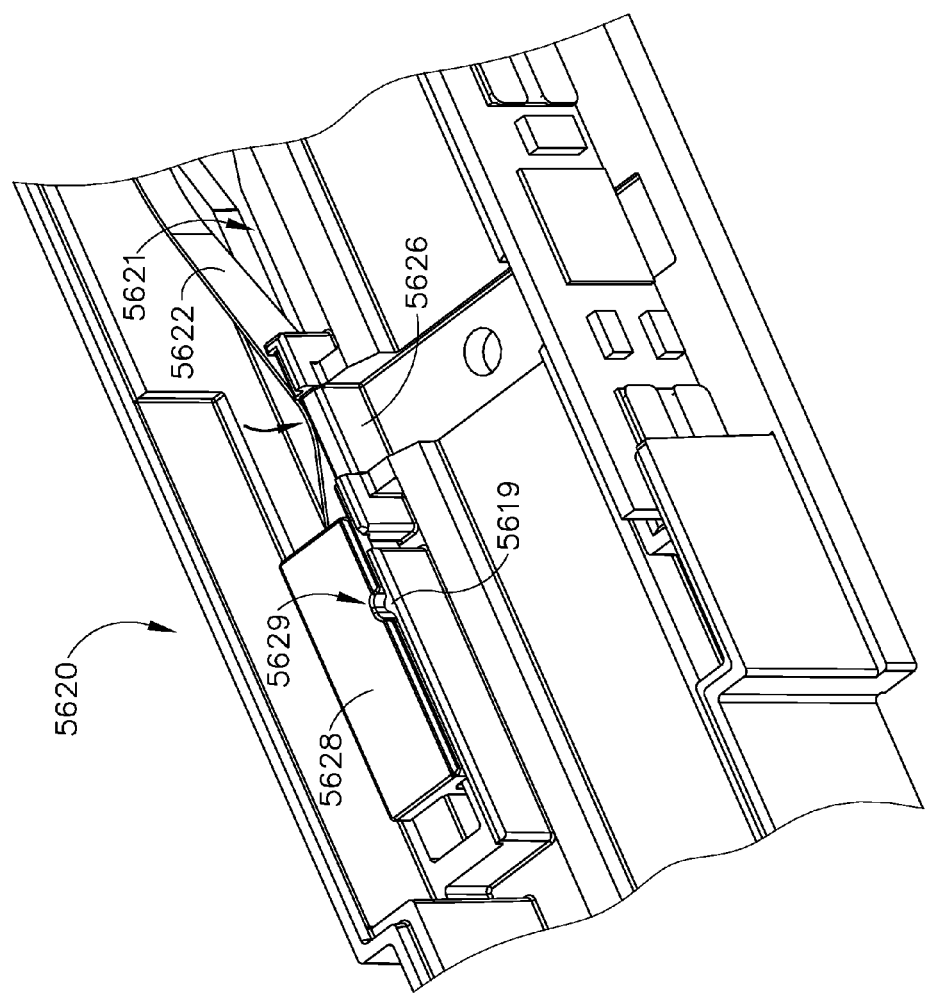
FIG. 48 depicts a detailed perspective view of the handle assembly of FIG. 34, with the lower housing of FIG. 38 removed from the handle assembly, and with the lockout sled of FIG. 39 remaining in the second position of FIG. 45 such that the drain contact of FIG. 47 is biased toward the positive contact of FIG. 47.
Figure 49:
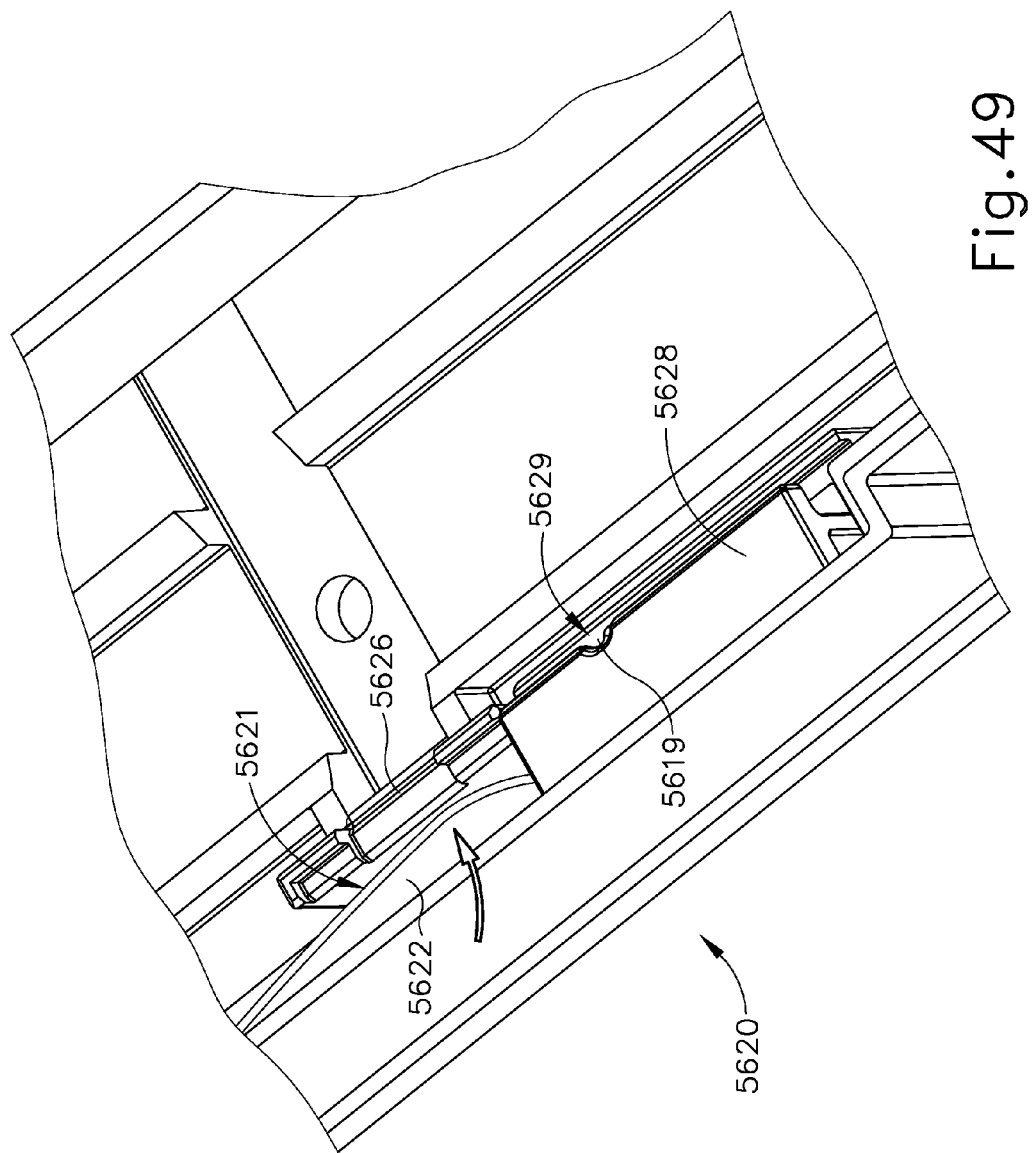
FIG. 49 depicts a detailed perspective view of the handle assembly of FIG. 34, with the lower housing of FIG. 38 removed from the handle assembly, and with the lockout sled of FIG. 39 remaining in the second position of FIG. 45 such that the drain contact of FIG. 47 is biased toward the positive contact of FIG. 47.

As best seen in FIG. 46, as lockout sled (5628) is driven proximally, a detent (5629) of lockout sled (5628) engages a detent (5619) formed in a sidewall of channel (5621) so as to "lock" lockout sled (5628) in the proximal position. As shown in FIGS. 47-49, as battery pack (5600) is removed, flange (111) is removed from lower housing (5620) such that flange (111) is no longer between positive battery contact (5622) and drain contact (5626). Thus, with lockout sled (5628) in the proximal position, the proximal end of positive battery contact (5622) contacts drain contact (5626) so as to drain batteries (5630) of power. Thus, it should be understood that insertion and removal of battery pack (5600) from housing (110) will ultimately drain batteries (5630). In other words, battery pack (5600) will be drained of power after a single use. Such power drainage will further eliminate potential energy available from battery contacts (5622, 5624) so as to limit the chances of battery pack (5600) igniting combustible materials upon disposal.

Figure 50:
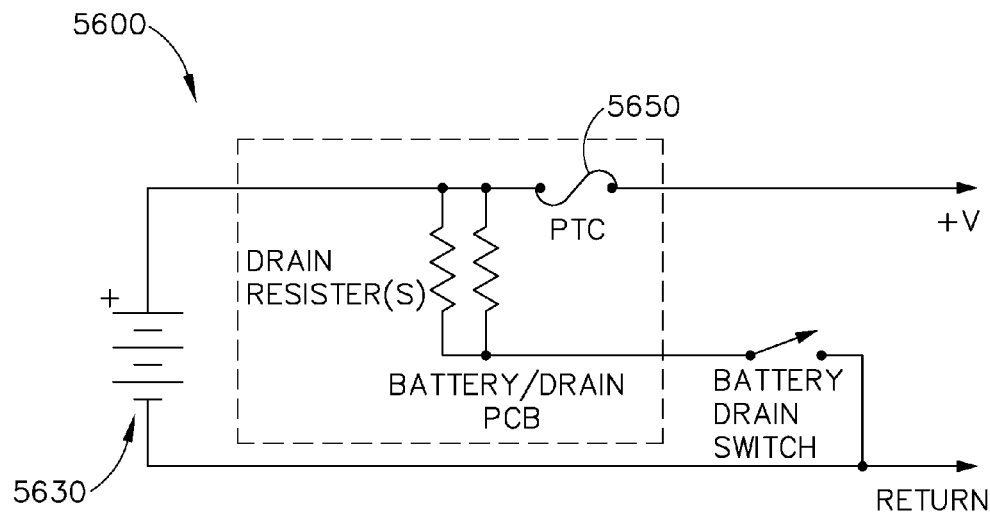
FIG. 50 depicts a schematic view of exemplary circuitry operable for use with any of the circular staplers described herein.
Figure 51:
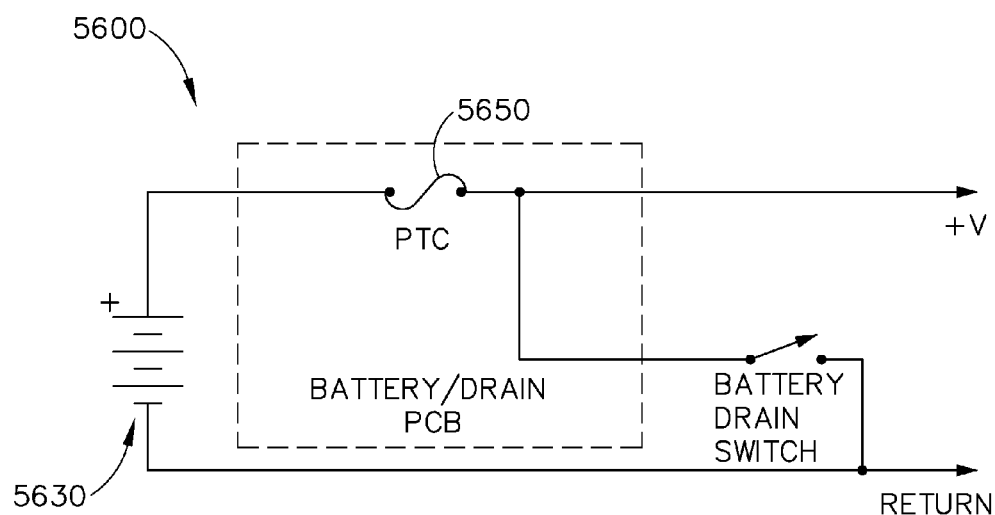
FIG. 51 depicts a schematic view of an exemplary alternative circuitry operable for use with any of the circular staplers described herein.

In addition, as shown in FIGS. 50-51, battery pack (5600) may include a positive temperature coefficient (PTC) current limiting device (5650). PTC limiting device (5650) may comprise materials that experience an increase in electrical resistance upon an increase in temperature. PTC limiting device (5650) is configured to control current during discharge so as to minimize any temperature rise in battery pack (5600) and/or its components. For instance, PTC limiting device (5650) may be configured to limit the temperature of battery pack (5600) and/or its components to below a flash point of common materials encountered during use or upon disposal. Various suitable materials and configurations that may be used to form PTC limiting device (5650) will be apparent to those of ordinary skill in the art in view of the teachings herein.

I. Exemplary Cycling-Complete Indicator

Figure 52A:
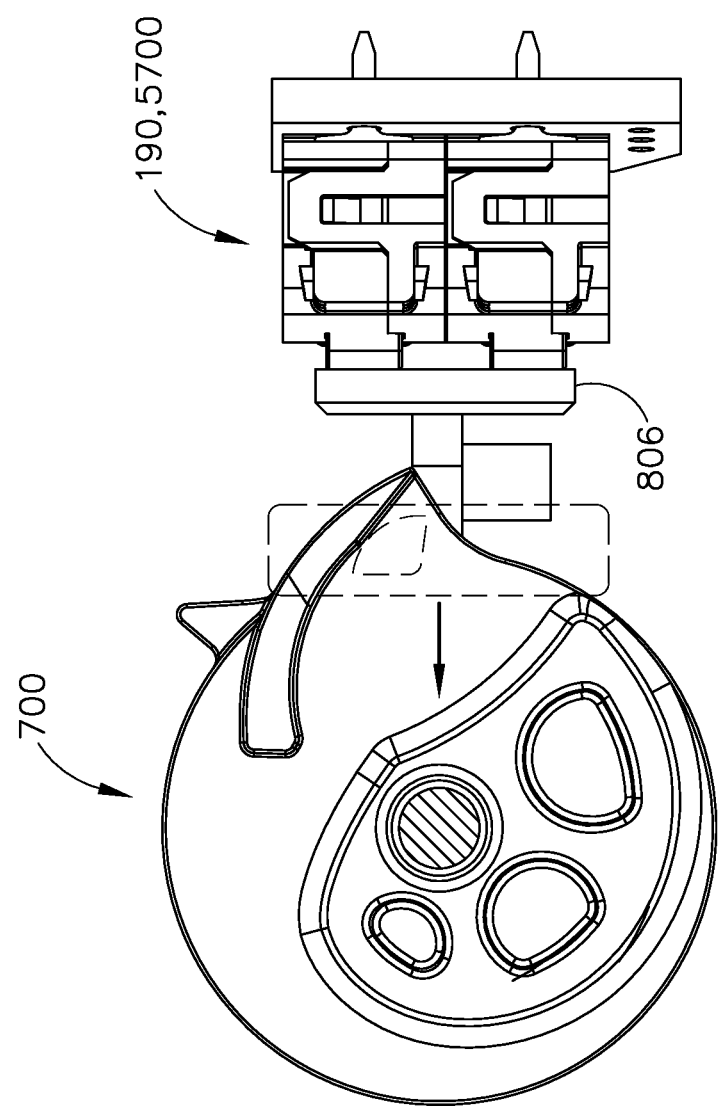
FIG. 52A depicts a side view of an exemplary indicator assembly, with a cam of the indicator assembly in a first rotational position.
Figure 52B:
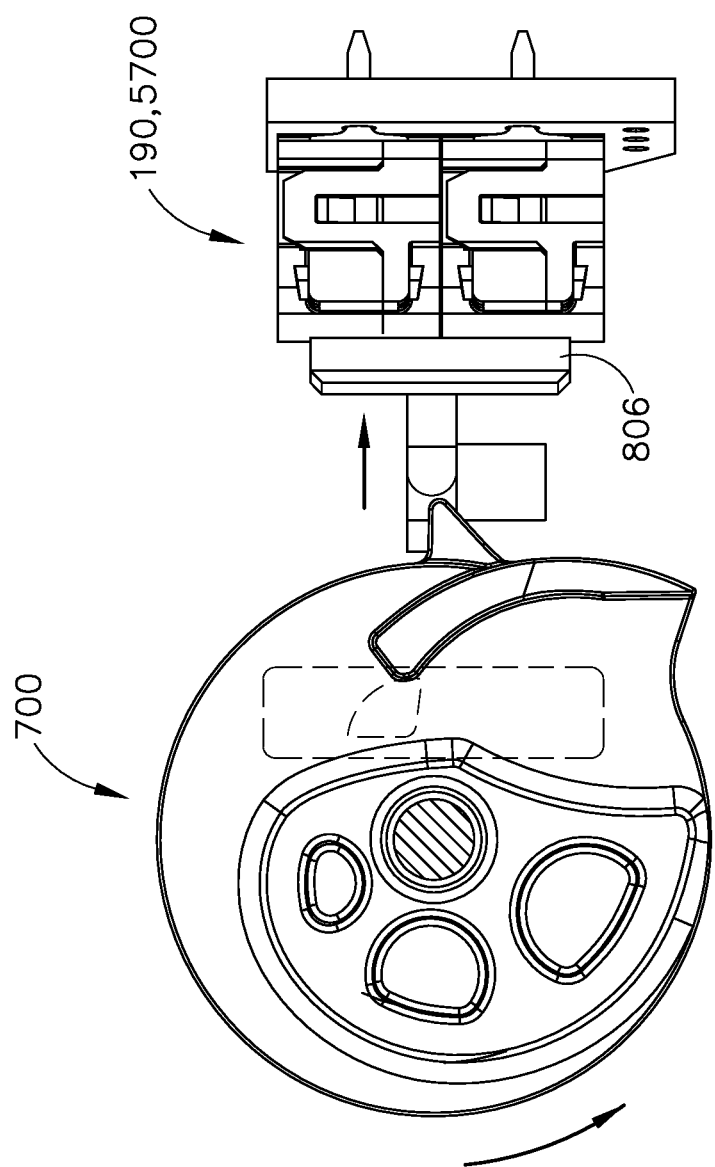
FIG. 52B depicts a side view of the indicator assembly of FIG. 52A, with the cam of FIG. 52A moved to a second rotational position so as to actuate a switch of the indicator assembly.

As discussed above, paddle (806) is configured to actuate a switch button (192) of a short circuit module (190). Short circuit module (190) is configured to prevent motor (160) from further activation when switch button (192) has been actuated. As shown in FIGS. 52A and 52B, paddle (806) may further be configured to actuate a switch (5700). Switch (5700) is operable to actuate an audible, tactile, and/or visible feedback feature (e.g., an LED) (not shown) so as to indicate completion of the firing cycle. Alternatively, switch button (192) may be operable to actuate an audible, tactile, and/or visible feedback feature in addition to actuating short circuit module (190).

J. Exemplary Anvil Position Indicator

Figures 53A, 53B, 53C, 53D, 53E:
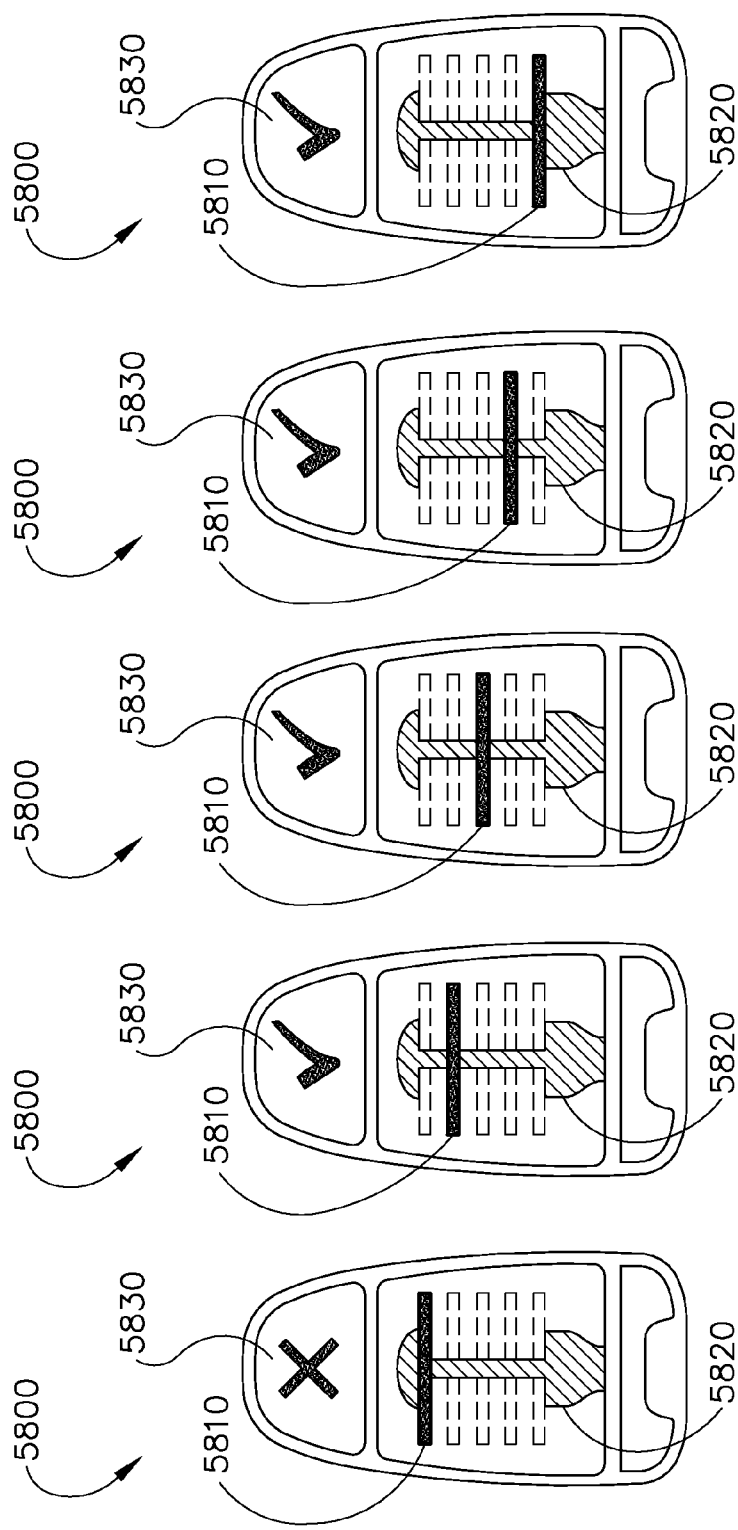
FIG. 53A depicts a top view of a display operable for use within any of the circular staplers described herein, with the display indicating that an anvil is not secured to a trocar.
FIG. 53B depicts a top view of the display of FIG. 53A, with the display indicating that the anvil is secured to a trocar and that the anvil is in a first position.
FIG. 53C depicts a top view of the display of FIG. 53A, with the display indicating that the anvil is secured to a trocar and that the anvil is in a second position.
FIG. 53D depicts a top view of the display of FIG. 53A, with the display indicating that the anvil is secured to a trocar and that the anvil is in a third position.
FIG. 53E depicts a top view of the display of FIG. 53A, with the display indicating that the anvil is secured to a trocar and that the anvil is in a fourth position.

FIGS. 53A-53E depict an exemplary gap distance indicator (5800). Indicator (5800) includes an electronic display (e.g., an LED display) that depicts a position of a visual representation of an anvil (5810) at varying longitudinal positions relative to a visual representation of a stapling head assembly (5820). It should therefore be appreciated that indicator (5800) depicts a gap distance (d) between opposing surfaces of anvil (5810) and stapling head assembly (5820). For instance, as shown in FIG. 53A, indicator (5800) depicts anvil (5810) at a distal longitudinal position relative to stapling head assembly (5820) when gap distance (d) is greatest. FIGS. 53B-53D depict anvil (5810) as anvil (5810) is translated progressively proximally toward stapling head assembly (5820) to a proximal longitudinal position as shown in FIG. 53E when gap distance (d) is smallest. It should be appreciated that the depiction of anvil (5810) and stapling head assembly (5820) may correspond to any anvil or shaft assembly described herein. By way of example only, the position of the depiction of anvil (5810) in relation to the depiction of stapling head assembly (5820) is based on signals from Hall Effect sensor (5532) as described above. Other suitable ways in which indicator (5800) may be driven to visually depict the gap distance (d) will be apparent to those of ordinary skill in the art in view of the teachings herein.

In some versions, indicator (5800) comprises an array of LEDs or other illuminating features. A circuit may selectively illuminate those illuminating features to indicate the gap distance (d).

Indicator (5800) further includes an anvil attachment indicator (5830) that is configured to indicate when any of the anvils described above have been appropriately attached to the trocars described above. For instance, in FIG. 53A, indicator (5830) indicates that anvil (5810) is not attached to stapling head assembly (5820); whereas in FIGS. 58B-58E, indicator (5830) indicates that anvil (5810) is appropriately attached to stapling head assembly (5820). By way of example only, the state of indicator (5830) may be based on the presence, absence, or character of a signal (5390) emitted from transmitter (5384) as described above. Other suitable ways in which indicator (5830) may be driven to visually indicate whether the anvil has been appropriately attached to the trocar will be apparent to those of ordinary skill in the art in view of the teachings herein.

In addition to or in lieu of the foregoing, indicator (5800) may provide visual, audible, and/or tactile feedback indicating proper insertion of a battery pack (120, 5120, 5600) into handle assembly (100, 5100). For instance, when battery pack (120, 5120, 5600) is fully inserted into handle assembly (100, 5100), a circuit in handle assembly (100, 5100) may automatically illuminate a backlight in indicator (5800). Other suitable ways in which a feature of handle assembly (100, 5100) may provide feedback indicating proper insertion of a battery pack (120, 5120, 5600) into handle assembly (100, 5100) will be apparent to those of ordinary skill in the art in view of the teachings herein.

In some variations of instrument (10), a circuit may monitor the voltage of battery pack (120) while battery pack (120) is under an electrical load. Such a circuit may further prevent activation of motor (160), and thereby prevent actuation of stapling head assembly (300), if the voltage of battery pack (120) is below a certain predetermined level while battery pack (120) is under an electrical load. In other words, motor (160) and stapling head assembly (300) may be rendered inoperable if battery pack (120) lacks a predetermined minimal voltage under an electrical load. In addition to or as an alternative to rendering motor (160) and stapling head assembly (300) inoperable, the circuit may provide a visual indication of the voltage level of battery pack (120) through indicator (5800) or otherwise.

Similarly, some variations of instrument (10) may include one or more features (e.g., a sensor, etc.) that is/are configured to authenticate battery pack (120). In the event that an operator attempts to couple a non-authentic battery pack (120) with handle assembly (100), instrument (10) may provide visual, audible, and/or tactile feedback indicating that the battery pack (120) is non-authentic. For instance, indicator (5800) may include a feature that provides visual indication that battery pack (120) is non-authentic. In addition or in the alternative, indicator (5800) may include a feature that provides visual indication that battery pack (120) is authentic. Various suitable ways in which a battery pack (120) may be authenticated, as well as various ways in which the instrument (10) may provide an operator with feedback indicating whether battery pack (120) is authentic, will be apparent to those of ordinary skill in the art in view of the teachings herein.

In addition to or in lieu of the foregoing features, indicator (5800) may also be operable to indicate whether stapling head assembly (300) is in a non-actuated state, when safety trigger (140) has been actuated such that stapling head assembly (300) Is ready to fire, when stapling head assembly (300) is engaged in a firing stroke, when stapling head assembly (300) has completed a firing stroke, and/or any other suitable information. Various suitable ways in which circuitry may drive indicator (5800) to provide such feedback in response to such conditions will be apparent to those of ordinary skill in the art in view of the teachings herein. Similarly, other kinds of conditions that may be conveyed through indicator (5800) and variations thereof will be apparent to those of ordinary skill in the art in view of the teachings herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical instrument comprising: (a) a body assembly, wherein the body assembly comprises a proximal end and a distal end; (b) a shaft assembly, wherein the shaft assembly extends distally from the distal end of the body assembly, wherein the shaft assembly comprises a proximal end and a distal end; (c) a stapling assembly, wherein the stapling assembly is disposed at the distal end of the shaft assembly, wherein the stapling assembly is operable to drive a plurality of staples into tissue, wherein the stapling assembly comprises: (i) a trocar, wherein the trocar is configured to selectively move between a distal position to a proximal position within the shaft assembly, and (ii) an anvil, wherein the anvil is selectively coupleable with the trocar, wherein the anvil is configured to move between the distal position and the proximal position when coupled with the trocar; (d) a firing assembly, wherein the firing assembly is coupled with the stapling assembly, wherein the firing assembly is configured to drive movement of the stapling assembly; (e) a sensor; (f) a circuit in communication with the sensor, wherein the circuit is configured to provide a response to a signal from the sensor indicating whether the firing assembly is ready to fire.

EXAMPLE 2

The surgical instrument of Example 1, further comprising a battery, wherein the battery is configured to provide electrical power to the firing assembly.

EXAMPLE 3

The surgical instrument of Example 2, wherein the sensor is configured to authenticate the battery, wherein the circuit is configured to indicate whether the firing assembly is ready to fire based on authentication of the battery by the sensor.

EXAMPLE 4

The surgical instrument of any one or more of Examples 2 through 3, wherein the sensor is configured to sense a voltage of the battery, wherein the circuit is configured to indicate whether the firing assembly is ready to fire based on the sensed voltage of the battery.

EXAMPLE 5

The surgical instrument of any one or more of Examples 2 through 4, wherein the battery is removable from the body assembly, wherein the sensor is configured to detect whether the battery is fully coupled with the body assembly, wherein the circuit is configured to indicate whether the firing assembly is ready to fire based on whether the battery is fully coupled with the body assembly as sensed by the sensor.

EXAMPLE 6

The surgical instrument of any one or more of Examples 1 through 5, wherein the sensor is configured to detect whether the anvil is fully secured to the trocar, wherein the circuit is configured to indicate whether the firing assembly is ready to fire based on whether the anvil is fully secured to the trocar as sensed by the sensor.

EXAMPLE 7

The surgical instrument of Example 6, wherein the sensor comprises a pair of electrical contacts in the anvil, wherein the trocar is configured to provide electrical continuity between the pair of electrical contacts when the anvil is fully secured to the trocar, wherein the circuit is configured to indicate whether the firing assembly is ready to fire based on whether the trocar is providing electrical continuity between the pair of electrical contacts.

EXAMPLE 8

The surgical instrument of any one or more of Examples 1 through 7, wherein the stapling assembly further comprises a staple deck, wherein the sensor is configured to detect whether the anvil is within a predefined spatial range relative to the staple deck, wherein the circuit is configured to indicate whether the firing assembly is ready to fire based on whether the anvil is within a predefined spatial range relative to the staple deck.

EXAMPLE 9

The surgical instrument of Example 8, wherein the anvil includes a magnet, wherein the trocar includes a Hall Effect sensor, wherein the Hall Effect sensor is configured to generate a voltage based on a distance of the magnet from the Hall Effect sensor, wherein the circuit is configured to indicate whether the firing assembly is ready to fire based on the voltage generated by the Hall Effect sensor.

EXAMPLE 10

The surgical instrument of any one or more of Examples 1 through 9, wherein the circuit includes a feedback feature positioned on the body assembly, wherein the feedback feature is operable to provide one or more of audio, visual, or tactile feedback indicating whether the firing assembly is ready to fire.

EXAMPLE 11

The surgical instrument of Example 10, wherein the feedback feature comprises a visual representation of the anvil, wherein the feedback feature is configured to change positioning of the visual representation of the anvil based on positioning of the anvil as sensed by the sensor.

EXAMPLE 12

The surgical instrument of any one or more of Examples 10 through 11, wherein the feedback feature comprises an array of illuminating features, wherein the circuit is operable to selectively illuminate the illuminating features based on positioning of the anvil as sensed by the sensor.

EXAMPLE 13

The surgical instrument of any one or more of Examples 10 through 12, wherein the feedback feature is operable to visually indicate whether the anvil is fully secured to the trocar, based on a signal from the sensor.

EXAMPLE 14

The surgical instrument of any one or more of Examples 1 through 13, wherein the circuit is further operable to disable the firing assembly in response to a signal from the sensor indicating that the firing assembly is not ready to fire.

EXAMPLE 15

The surgical instrument of any one or more of Examples 1 through 14, further comprising a battery pack, wherein the battery pack is configured to provide power to the firing assembly, wherein the battery pack is selectively insertable into and removable from the body assembly, wherein battery pack includes a feature operable to initiate draining of power from the battery pack in response to a combination of both of the following conditions occurring: (i) insertion of the battery pack in the body assembly, and (ii) removal of the battery pack from the body assembly.

EXAMPLE 16

The surgical instrument of any one or more of Examples 1 through 15, wherein the trocar comprises a marker region visible via a pinhole formed in the anvil when the anvil is coupled to the trocar.

EXAMPLE 17

The surgical instrument of any one or more of Examples 1 through 17, wherein the anvil comprises at least one latch member configured to couple the anvil with the trocar, wherein the at least one latch member comprises a marker region.

EXAMPLE 18

The surgical instrument of any one or more of Examples 1 through 17, further comprising a battery pack, wherein the battery pack is configured to provide power to the firing assembly, wherein the battery pack is selectively insertable into and removable from the body assembly, wherein the body assembly comprises a lockout assembly configured to limit movement of the trocar when the battery pack is not inserted within the body assembly

EXAMPLE 19

A surgical instrument comprising: (a) a body assembly, wherein the body assembly comprises a proximal end and a distal end; (b) a shaft assembly, wherein the shaft assembly extends distally from the distal end of the body assembly, wherein the shaft assembly comprises a proximal end and a distal end; (c) a stapling assembly, wherein the stapling assembly is disposed at the distal end of the shaft assembly, wherein the stapling assembly is operable to drive a plurality of staples into tissue, wherein the stapling assembly comprises: (i) a trocar, wherein the trocar is configured to selectively move between a distal position to a proximal position within the shaft assembly, and an (ii) anvil, wherein the anvil is selectively coupleable with the trocar, wherein the anvil is configured to move between the distal position and the proximal position when coupled with the trocar; (d) a firing assembly, wherein the firing assembly is coupled with the stapling assembly, wherein the firing assembly is configured to drive movement of the stapling assembly; and (e) a position sensing assembly, wherein the position sensing assembly is configured to sense a position of the anvil relative to the distal end of the shaft assembly

EXAMPLE 20

A surgical instrument comprising: (a) a body assembly, wherein the body assembly comprises a proximal end and a distal end, wherein the body assembly comprises a lockout assembly; (b) a shaft assembly, wherein the shaft assembly extends distally from the distal end of the body assembly, wherein the shaft assembly comprises a proximal end and a distal end; (c) a stapling assembly, wherein the stapling assembly is disposed at the distal end of the shaft assembly, wherein the stapling assembly is operable to drive a plurality of staples into tissue, wherein the stapling assembly comprises: (i) a trocar, wherein the trocar is configured to selectively move between a distal position to a proximal position within the shaft assembly, and (ii) an anvil, wherein the anvil is selectively coupleable with the trocar, wherein the anvil is configured to move between the distal position and the proximal position when coupled with the trocar; (d) a firing assembly, wherein the firing assembly is coupled with the stapling assembly, wherein the firing assembly is configured to drive movement of the stapling assembly; (e) a battery pack, wherein the battery pack is configured to provide power to the firing assembly, wherein the battery pack is selectively insertable into and removable from the body assembly; and a knob, wherein the knob is configured to rotate to thereby cause movement of the trocar, wherein the lockout assembly is configured to restrict rotation of the knob unless the battery pack is fully inserted into the body assembly.

EXAMPLE 21

A surgical instrument comprising: (a) a body assembly, wherein the body assembly comprises a proximal end and a distal end; (b) a shaft assembly, wherein the shaft assembly extends distally from the distal end of the body assembly, wherein the shaft assembly comprises a proximal end and a distal end; (c) a stapling assembly, wherein the stapling assembly is disposed at the distal end of the shaft assembly, wherein the stapling assembly is operable to drive a plurality of staples into tissue, wherein the stapling assembly comprises: (i) a trocar, wherein the trocar is configured to selectively move between a distal position to a proximal position within the shaft assembly, and (ii) an anvil, wherein the anvil is selectively coupleable with the trocar, wherein the anvil is configured to move between the distal position and the proximal position when coupled with the trocar; (d) a firing assembly, wherein the firing assembly is coupled with the stapling assembly, wherein the firing assembly is configured to drive movement of the stapling assembly; and (e) a battery pack, wherein the battery pack is configured to provide power to the firing assembly, wherein the battery pack is selectively insertable into and removable from the body assembly, wherein battery pack includes a feature operable to initiate draining of power from the battery pack in response to a combination of both of the following conditions occurring: (i) insertion of the battery pack in the body assembly, and (ii) removal of the battery pack from the body assembly.

EXAMPLE 22

The instrument of Example 21, wherein the battery pack comprises a positive battery contact and a negative battery contact.

EXAMPLE 23

The instrument of Example 22, wherein the feature operable to initiate draining of power from the battery pack comprises a drain contact, wherein the positive battery contact is configured to contact the drain contact to thereby drain power from the battery pack.

EXAMPLE 24

The instrument of Example 23, wherein the battery pack comprises a lockout sled slidably secured within the battery pack, wherein the lockout sled is translatable between a distal position and a proximal position.

EXAMPLE 25

The instrument of Example 24, wherein the lockout sled is configured to prevent contact between the positive battery contact and the drain contact when the lockout sled is in the distal position.

EXAMPLE 26

The instrument of any one or more of Examples 24 through 25, wherein the lockout sled is configured to permit contact between the positive battery contact and the drain contact when the lockout sled is in the proximal position.

EXAMPLE 27

The instrument of any one or more of Examples 24 through 26, wherein the body assembly comprises a flange.

EXAMPLE 28

The instrument of Example 27, wherein the flange is configured to drive the lockout sled from the distal position to the proximal position upon insertion of the battery pack into the body assembly.

EXAMPLE 29

The instrument of any one or more of Examples 27 through 28, wherein the flange is configured to prevent contact between the positive battery contact and the drain contact when the battery pack is inserted into the body assembly.

EXAMPLE 30

The instrument of any one or more of Examples 24 through 29, wherein the lockout sled is configured to remain in the proximal position.

EXAMPLE 31

The instrument of Example 30, wherein a detent of the lockout sled is configured to engage a detent of the body assembly to thereby lock the lockout sled in the proximal position.

EXAMPLE 32

The instrument of any one or more of Examples 21 through 31, wherein the battery pack comprises at least one latch configured to selectively lock the battery pack within the body assembly.

EXAMPLE 33

The instrument of any one or more of Examples 21 through 32, wherein the battery pack comprises a positive temperature coefficient current limiting device.

EXAMPLE 34

The instrument of any one or more of Examples 21 through 33, wherein the trocar comprises a marker region visible via a pinhole formed in the anvil when the anvil is coupled to the trocar.

EXAMPLE 35

The instrument of any one or more of Examples 21 through 34, wherein the anvil comprises at least one latch member configured to couple the anvil with the trocar, wherein the at least one latch member comprises a marker region.

EXAMPLE 36

The instrument of any one or more of Examples 21 through 35, wherein the body assembly comprises a lockout assembly configured to limit movement of the trocar when the battery pack is not inserted within the body assembly.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. Pub. No. 2014/0151429, entitled "Trans-Oral Circular Anvil Introduction System with Dilation Feature," published Jun. 5, 2014, now U.S. Pat. No. 9,572,573, issued Feb. 21, 2017, the disclosure of which is incorporated by reference herein; U.S. Pub. No. 2014/0144968, entitled "Surgical Staple with Integral Pledget for Tip Deflection," published May 29, 2014, now U.S. Pat. No. 9,289,207, issued Mar. 22, 2016, the disclosure of which is incorporated by reference herein; U.S. Pub. No. 2014/0158747, entitled "Surgical Stapler with Varying Staple Widths along Different Circumferences," published Jun. 12, 2014, the disclosure of which is incorporated by reference herein; U.S. Pub. No. 2014/0144969, entitled "Pivoting Anvil for Surgical Circular Stapler," published May 29, 2014, now U.S. Pat. No. 9,498,222, issued Nov. 22, 2016, the disclosure of which is incorporated by reference herein; U.S. Pub. No. 2014/0151430, entitled "Circular Anvil Introduction System with Alignment Feature," published Jun. 5, 2014, now U.S. Pat. 9,724,100, issued Aug. 8, 2017, the disclosure of which is incorporated by reference herein; U.S. Pub. No. 2014/0166717, entitled "Circular Stapler with Selectable Motorized and Manual Control, Including a Control Ring," published Jun. 19, 2014, now U.S. Pat. No. 9,532,783, issued Jan. 3, 2017, the disclosure of which is incorporated by reference herein; U.S. Pub. No. 2014/0166728, entitled "Motor Driven Rotary Input Circular Stapler with Modular End Effector," published Jun. 19, 2014, now U.S. Pat. No. 9,597,081, issued Mar. 31, 2017, the disclosure of which is incorporated by reference herein; and/or U.S. Pub. No. 2014/0166718, entitled "Motor Driven Rotary Input Circular Stapler with Lockable Flexible Shaft," published Jun. 19, 2014, now U.S. Pat. No. 9,463,022, issued Oct. 11, 2016, the disclosure of which is incorporated by reference herein. Various suitable ways in which such teachings may be combined will be apparent to those of ordinary skill in the art.

While the examples herein have been provided in the context of a circular stapling instrument, it should be understood that the various teachings herein may be readily applied to various other kinds of surgical instruments. By way of example only, the various teachings herein may be readily applied to linear stapling devices (e.g., endocutters). For instance, various teachings herein may be readily combined with various teachings of U.S. Pub. No. 2012/0239012, entitled "Motor-Driven Surgical Cutting Instrument with Electric Actuator Directional Control Assembly," published Sep. 20, 2012, now U.S. Pat. No. 8,453,914, issued Jun. 4, 2013, the disclosure of which is incorporated by reference herein, and/or U.S. Pub. No. 2010/0264193, entitled "Surgical Stapling Instrument with An Articulatable End Effector," published Oct. 21, 2010, now U.S. Pat. No. 8,408,439, issued Apr. 2, 2013, the disclosure of which is incorporated by reference herein, as will be apparent to those of ordinary skill in the art. As another merely illustrative example, the various teachings herein may be readily applied to a motorized electrosurgical device. For instance, various teachings herein may be readily combined with various teachings of U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein, as will be apparent to those of ordinary skill in the art. Other suitable kinds of instruments in which the teachings herein may be applied, and various ways in which the teachings herein may be applied to such instruments, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a body assembly, wherein the body assembly comprises a proximal end and a distal end;
   (b) a shaft assembly, wherein the shaft assembly extends distally from the distal end of the body assembly, wherein the shaft assembly comprises a proximal end and a distal end;
   (c) a stapling assembly, wherein the stapling assembly is disposed at the distal end of the shaft assembly, wherein the stapling assembly is operable to drive a plurality of staples into tissue, wherein the stapling assembly comprises:
      (i) a trocar, wherein the trocar is configured to selectively move between a distal position to a proximal position within the shaft assembly, and
      (ii) an anvil, wherein the anvil is selectively coupleable with the trocar, wherein the anvil is configured to move between the distal position and the proximal position when coupled with the trocar;
   (d) a firing assembly, wherein the firing assembly is coupled with the stapling assembly, wherein the firing assembly is configured to drive movement of the stapling assembly;
   (e) a sensor;
   (f) a circuit in communication with the sensor, wherein the circuit is configured to provide a response to a signal from the sensor indicating whether the firing assembly is ready to fire; and
   (g) a battery pack, wherein the battery pack is configured to provide power to the firing assembly, wherein the battery pack is selectively insertable into and removable from the body assembly, wherein the battery pack includes a feature operable to initiate draining of power from the battery pack after a combination of both of the following conditions occurring:
      (i) insertion of the battery pack in the body assembly, and
      (ii) removal of the inserted battery pack from the body assembly.

2. The surgical instrument of claim 1, wherein the sensor is configured to authenticate the battery pack, wherein the circuit is configured to indicate whether the firing assembly is ready to fire based on authentication of the battery pack by the sensor.

3. The surgical instrument of claim 1, wherein the sensor is configured to sense a voltage of the battery pack, wherein the circuit is configured to indicate whether the firing assembly is ready to fire based on the sensed voltage of the battery pack.

4. The surgical instrument of claim 1, wherein the battery pack is removable from the body assembly, wherein the sensor is configured to detect whether the battery pack is fully coupled with the body assembly, wherein the circuit is configured to indicate whether the firing assembly is ready to fire based on whether the battery pack is fully coupled with the body assembly as sensed by the sensor.

5. The surgical instrument of claim 1, wherein the sensor is configured to detect whether the anvil is fully secured to the trocar, wherein the circuit is configured to indicate whether the firing assembly is ready to fire based on whether the anvil is fully secured to the trocar as sensed by the sensor.

6. The surgical instrument of claim 5, wherein the sensor comprises a pair of electrical contacts in the anvil, wherein the trocar is configured to provide electrical continuity between the pair of electrical contacts when the anvil is fully secured to the trocar, wherein the circuit is configured to indicate whether the firing assembly is ready to fire based on whether the trocar is providing electrical continuity between the pair of electrical contacts.

7. The surgical instrument of claim 1, wherein the stapling assembly further comprises a staple deck, wherein the sensor is configured to detect whether the anvil is within a predefined spatial range relative to the staple deck, wherein the circuit is configured to indicate whether the firing assembly is ready to fire based on whether the anvil is within a predefined spatial range relative to the staple deck.

8. The surgical instrument of claim 7, wherein the anvil includes a magnet, wherein the trocar includes a Hall Effect sensor, wherein the Hall Effect sensor is configured to generate a voltage based on a distance of the magnet from the Hall Effect sensor, wherein the circuit is configured to indicate whether the firing assembly is ready to fire based on the voltage generated by the Hall Effect sensor.

9. The surgical instrument of claim 1, wherein the circuit includes a feedback feature positioned on the body assembly, wherein the feedback feature is operable to provide one or more of audio, visual, or tactile feedback indicating whether the firing assembly is ready to fire.

10. The surgical instrument of claim 9, wherein the feedback feature comprises a visual representation of the anvil, wherein the feedback feature is configured to change positioning of the visual representation of the anvil based on positioning of the anvil as sensed by the sensor.

11. The surgical instrument of claim 9, wherein the feedback feature comprises an array of illuminating features, wherein the circuit is operable to selectively illuminate the illuminating features based on positioning of the anvil as sensed by the sensor.

12. The surgical instrument of claim 9, wherein the feedback feature is operable to visually indicate whether the anvil is fully secured to the trocar, based on a signal from the sensor.

13. The surgical instrument of claim 1, wherein the circuit is further operable to disable the firing assembly in response to a signal from the sensor indicating that the firing assembly is not ready to fire.

14. The surgical instrument of claim 1, wherein the trocar comprises a marker region visible via a pinhole formed in the anvil when the anvil is coupled to the trocar.

15. The surgical instrument of claim 1, wherein the anvil comprises at least one latch member configured to couple the anvil with the trocar, wherein the at least one latch member comprises a marker region.

16. The surgical instrument of claim 1, wherein the body assembly comprises a lockout assembly configured to limit movement of the trocar when the battery pack is not inserted within the body assembly.

17. A surgical instrument comprising:
(a) a body assembly comprising a lockout assembly, wherein the body assembly comprises a proximal end a distal end, and a flange;
(b) a shaft assembly, wherein the shaft assembly extends distally from the distal end of the body assembly, wherein the shaft assembly comprises a proximal end and a distal end;
(c) a stapling assembly, wherein the stapling assembly is disposed at the distal end of the shaft assembly, wherein the stapling assembly is operable to drive a plurality of staples into tissue, wherein the stapling assembly comprises:
  (i) a trocar, wherein the trocar is configured to selectively move between a distal position to a proximal position within the shaft assembly, and
  (ii) an anvil, wherein the anvil is selectively coupleable with the trocar, wherein the anvil is configured to move between the distal position and the proximal position when coupled with the trocar;
(d) a firing assembly, wherein the tiring assembly is coupled with the stapling assembly, wherein the firing assembly is configured to drive movement of the stapling assembly; and
(e) a battery pack, wherein the battery pack is configured to provide power to the firing assembly, wherein the battery pack is selectively insertable into and removable from the body assembly, wherein the lockout assembly of the body assembly is configured to limit movement of the trocar when the battery pack is not inserted into the body assembly.

18. A surgical instrument comprising:
(a) a body assembly, wherein the body assembly comprises a proximal end and a distal end, wherein the body assembly comprises a lockout assembly;
(b) a shaft assembly, wherein the shaft assembly extends distally from the distal end of the body assembly, wherein the shaft assembly comprises a proximal end and a distal end;
(c) a stapling assembly, wherein the stapling assembly is disposed at the distal end of the shaft assembly, wherein the stapling assembly is operable to drive a plurality of staples into tissue, wherein the stapling assembly comprises:
  (i) a trocar, wherein the trocar is configured to selectively move between a distal position to a proximal position within the shaft assembly, and
  (ii) an anvil, wherein the anvil is selectively coupleable with the trocar, wherein the anvil is configured to move between the distal position and the proximal position when coupled with the trocar;
(d) a firing assembly, wherein the firing assembly is coupled with the stapling assembly, wherein the firing assembly is configured to drive movement of the stapling assembly;
(e) a battery pack, wherein the battery pack is configured to provide power to the firing assembly, wherein the battery pack is selectively insertable into and removable from the body assembly; and
(f) a knob, wherein the knob is configured to rotate to thereby cause movement of the trocar, wherein the lockout assembly is configured to restrict rotation of the knob unless the battery pack is fully inserted into the body assembly.

* * * * *